(12) United States Patent
Mullinax et al.

(10) Patent No.: US 8,314,220 B2
(45) Date of Patent: Nov. 20, 2012

(54) METHODS COMPOSITIONS, AND KITS FOR DETECTION OF MICRORNA

(75) Inventors: Rebecca L. Mullinax, San Diego, CA (US); Joseph A. Sorge, Wilson, WY (US)

(73) Assignee: Agilent Technologies, Inc., Santa Clara, CA (US)

( * ) Notice: Subject to any disclaimer, the term of this patent is extended or adjusted under 35 U.S.C. 154(b) by 1464 days.

(21) Appl. No.: 11/627,926

(22) Filed: Jan. 26, 2007

(65) Prior Publication Data

US 2008/0182239 A1 Jul. 31, 2008

(51) Int. Cl.
C07H 21/02 (2006.01)
C12Q 1/68 (2006.01)
C07H 21/04 (2006.01)
(52) U.S. Cl. .................... 536/22.1; 435/6; 536/24.33
(58) Field of Classification Search .................. 536/22.1; 435/6
See application file for complete search history.

(56) References Cited

U.S. PATENT DOCUMENTS

| | | | |
|---|---|---|---|
| 5,595,890 A * | 1/1997 | Newton et al. ............... | 435/91.2 |
| 5,962,271 A | 10/1999 | Chenchik et al. | |
| 5,962,272 A | 10/1999 | Chenchik et al. | |
| 2005/0272075 A1 | 12/2005 | Jacobsen et al. | |
| 2006/0019258 A1 | 1/2006 | Yeakley | |
| 2006/0051771 A1 | 3/2006 | Murphy et al. | |
| 2006/0078906 A1 | 4/2006 | Chen et al. | |
| 2006/0211000 A1 | 9/2006 | Sorge et al. | |
| 2009/0142752 A1 * | 6/2009 | Hall et al. ............... | 435/6 |

FOREIGN PATENT DOCUMENTS
WO WO 2006/081824 8/2006

OTHER PUBLICATIONS

Shi, R. et al. Facile means for quantifying microRNA by real-time PCR. Biotechniques, vol. 39, pp. 519-525, 2005.*
Abbott, A.L. et al. 2005. The let-7 MicroRNA family members mir-48, mir-84, and mir-241 function together to regulate developmental timing in *Caenorhabditis elegans*. Dev. Cell 9:403-414.
Brennecke, J. et al. 2005. Principles of microRNA-target recognition. PloS Biol. 3(3):e85.
Castoldi, M. et al. 2006. A sensitive array for microRNA expression profiling (miChip) based on locked nucleic acids (LNA). RNA. 12(5):913-920.
Chen, C. et al. 2005. Real time quantification of micro RNAs by Stem-Loop RT-PCR. NAR 33(20) e179.
Feng, Y. et al. 200. Unpaired terminal nucleotides and 5' monphosphorylation govern 3' polyadenylation by *E. coli* poly(A) polymerase I. PNAS 97(12):6415-6420.
Fire, A. et al. 1998. Potent and specific genetic interference by double-stranded RNA in *Caenorhabditis elegans*. Nature. 391:806-811.
Higuchi, R. et al. 1993. Kinetic PCR Analysis: Real-time Monitoring of DNA Amplification Reactions. Bio/Technology 11:1026-1030.
Holland, P.M. et al. 1991. Detection of Specific Polymerase Chain Reaction Product by Utilizing the 5' to 3' Exonuclease Activity of *Thermus aquaticus* DNA Polymerase. PNAS 88:7276-7280.
Hu W-S et al. 1990. Retroviral recombination and reverse transcription. Science. 250:1227-1233.
Leaman, D. et al. 2005. Antisense mediated depletion reveals essential and specific functions of microRNAs in *Drosophila* development. Cell 121:1097-1108.
Lewis, B. P. et al. 2003. Prediction of Mammalian MicroRNA Targets. Cell. 115:787-798.
Lu J. et al. 2005. MicroRNA expression profiles classify human cancers. Nature 435:834-838.
Lu, R. et al. 2005. Facile means for quantifying microRNA expression by real-time PCR. 2005. BioTechniques. 39(4):519-25.
Maher, C. et al. 2006. Evolution of *Arabidopsis* microRNA families through duplication events. Genome Res. 16:510-519.
Mathews, D. H. et al. 1999. Expanded Sequence Dependence of Thermodynamic Parameters Improves Prediction of RNA Secondary Structure. J. Mol. Biol. 288, 911-940.
Matz, M. et al. 1999. Amplification of cDNA ends based on template-switching effect and step-out PCR. Nucleic Acids Res. 15:27(6):1558-1560.
Petersen, M. et al. 2003. LNA: A versatile tool for therapeutics and genomics. Trends Biotechnol. 21:74-81.
Raymond, C. K. et al. 2005. Simple- quantitative primer-extension PCR assay for direct monitoring of microRNAs and short-interfering RNAs. RNA. 11:1737-1744.
Shanfa, L. et al. 2005. Novel and Mechanical Stress—Responsive MicroRNAs in *Populus trichocarpa* that Are Absent from *Arabidopsis*. Plant Cell. 17(8): 2186-2203.
Shi, R. et al. 2005. Facile Means for Quantifying microRNA Expression by Real-Time PCR. BioTechniques 39:519-525.
Volinia, S. et al. 2006. A microRNA expression signature of human solid tumors defines cancer gene targets. Proc. Natl. Acad. Sci. USA 103;2257-2261.
Yeakley, J. M. Methods and Compositions for Detection of Small Interfering RNA and Micro-RNA.
Zhang J. et al. 1993. Rate and mechanism of non-homologous recombination during a single cycle of retroviral replication. Science. 259:234-238.
Zuker, M. 2003. Mfold web server for nucleic acid folding and hybridization prediction. Nucleic Acids Res. 31(13): 3406-3415.
Chen,C., et al. "Real-time quantification of microRNAs by stem-loop RT-PCR", Nucleic Acids Research, Nov. 2005, vol. 33, No. 20, pp. e179(1-9).
Lu,S., et al. "Novel and Mechanical Stress-Responsive MicroRNAs in *Populus trichocarpa* That Are Absent from *Arabidopsis*", Plant Cell, Aug. 2005, vol. 17, No. 8, pp. 2186-2203.

(Continued)

*Primary Examiner* — Prabha Chunduru

(57) ABSTRACT

The present invention provides methods, nucleic acids, compositions, and kits for detecting microRNA (miRNA) in samples. The methods comprise designing mRNA-specific primers, adding a polyA tail to the miRNA, and using reverse transcription and amplification to detect the miRNA. The nucleic acids, compositions, and kits typically comprise some or all of the components necessary to practice the methods of the invention.

13 Claims, 22 Drawing Sheets

OTHER PUBLICATIONS

Wang,Y. et al. "MicroRNA: Past and Present", Front. Biosci. Jan. 1, 2007, vol. 12, pp. 2316-2329.

PCT International Search Report and Written Opinion received in Application No. PCT/US2008/051932, mailed Aug. 4, 2008, pp. 1-12.

* cited by examiner

| miRNA | Nucleotide sequence (5' to 3') | SEQ ID NO: |
|---|---|---|
| let-7a | UGAGGUAGUAGGUUGUAUAGUU | 1 |
| let-7b | ----------------G----- | 2 |
| let-7c | ------------------G--- | 3 |
| let-7d | A--------------C---- | 4 |
| let-7e | --------G------------ | 5 |
| let-7f | ----------A---------- | 6 |
| miR-98 | ----------A-------U--- | 27 |
| let-7g | ----------U-----C--- | 7 |
| let-7i | ----------U----GCU-- | 8 |

Figure 7.

no non-templated nucleotide addition let-7aFwt; SEQ ID NO: 66

```
5'-TGAGGTAGTAGGTTGTATAGTT-3'
   |||||||||||||||||||||
3'-ACTCCATCATCCAACATATCAAT₁₂GGATATCACTCAGCATAATTAAGACACGAGCGTTCCAGC-5'
``` let-7a cDNA template non-templated addition of C let-7aF3Gwt; SEQ ID NO: 67

```
5'-GGGTGAGGTAGTAGGTTGTATAGTT-3'
      |||||||||||||||||||||
3'-CCCACTCCATCATCCAACATATCAAT₁₂GGATATCACTCAGCATAATTAAGACACGAGCGTTCCAGC-5'
``` let-7a cDNA template non-templated addition of T let-7aF3Awt; SEQ ID NO: 181

```
5'-AAATGAGGTAGTAGGTTGTATAGTT-3'
      |||||||||||||||||||||
3'-TTTACTCCATCATCCAACATATCAAT₁₂GGATATCACTCAGCATAATTAAGACACGAGCGTTCCAGC-5'
``` let-7a cDNA template

Figure 8B.

non-templated addition of A let-7aF3Twt; SEQ ID NO: 182

```
5'-TTTTGAGGTAGTAGGTTGTATAGTT-3'
   ||||||||||||||||||||||||
3'-AAAACTCCATCATCCAACATATCAAT₁₂GGATATCACTCAGCATAATTAAGACACGAGCGTTCCAGC-5'
``` let-7a cDNA template non-templated addition of G let-7aF3Cwt; SEQ ID NO: 183

```
5'-CCCTGAGGTAGTAGGTTGTATAGTT-3'
   ||||||||||||||||||||||||
3'-GGGTCTCCATCATCCAACGTATCAAT₁₂GGATATCACTCAGCATAATTAAGACACGAGCGTTCCAGC-5'
``` let-7a cDNA template

Figure 8C.

| miRNA | Nucleotide sequence (5' to 3') | SEQ ID NO: |
|---|---|---|
| let-7a | U--------------U-----U | 1 |
| let-7b | U--------------UG-G--U | 2 |
| let-7c | U--------------U--G--U | 3 |
| let-7d | AGAGGUAGUAGGUUGCAUAGU | 4 |
| let-7e | U-------G------U----- | 5 |
| let-7f | U---------A----U-----U | 6 |
| miR-98 | U---------A----U----- | 28 |
| let-7g | U----------U---U-C--- | 7 |
| let-7i | U----------U---UGCU-- | 8 |

Figure 10.

|  | miRNA-Specific Primer | | |
| --- | --- | --- | --- |
| Template | let-7aF3G-3 | let-7cF3G-3 | let-7dF3G-5 |
|  | % Relative Detection | | |
| let-7a miRNA | 100.00 | 6.09 | 0.03 |
| let-7b miRNA | 0.24 | 11.73 | 0.04 |
| let-7c miRNA | 58.37 | 100.00 | 0.24 |
| let-7d miRNA | 253.55 | 0.52 | 100.00 |
| let-7e miRNA | 49.98 | 0.97 | 0.05 |
| let-7f miRNA | 71.48 | 1.60 | 0.01 |
| let-7g miRNA | 0.06 | 0.04 | 0.01 |
| miR-98 miRNA | 12.96 | 0.02 | 0.00 |
| let-7i miRNA | 0.05 | 0.01 | 0.01 |

Figure 14.

| | SEQ ID NO: | % Relative detection | | Nucleotide sequence (5' to 3') | Mismatch |
|---|---|---|---|---|---|
| | | Perfect Match (U/reaction) | | | |
| | | 0.0 | 0.00008 | | |
| let-7cF3G-3 primer | 80 | | | GGGTGAGGTAGTAGGTTGTATG | |
| let-7a miRNA | 1 | 7.3 | 0.3 | ------------------A--- | G:T |
| let-7b miRNA | 2 | 13.5 | 1.5 | ----------------G----- | A:C |
| let-7c miRNA | 3 | 100 | 100.0 | ---------------------- | none |
| let-7d miRNA | 4 | 0.7 | nd | A--------------C---- | T:T,T:G |
| let-7e miRNA | 5 | 1.3 | nd | --------G---------A-- | T:C,G:T |
| let-7f miRNA | 6 | 2.1 | nd | -----------A------A--- | G:T,G:T |
| miR-98 miRNA | 27 | 0.1 | nd | ----------A-------U--- | G:T,G:A |
| let-7g miRNA | 7 | 0.0 | nd | -----------U-----CA-- | G:A,T:G, G:T |
| let-7i miRNA | 8 | 0.0 | nd | -----------U----GCU-- | G:A,A:C, T:G,G:A |

Figure 16.

nd: not done

SEQUENCE LISTING

```
<160> NUMBER OF SEQ ID NOS: 189

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
ugagguagua gguuguauag uu                                              22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
ugagguagua gguugugugg uu                                              22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ugagguagua gguuguaugg uu                                              22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
```

```
agagguagua gguugcauag u                                    21

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ugagguagga gguuguauag u                                    21

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
ugagguagua gauuguauag uu                                   22

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugagguagua guuguacag u                                     21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
ugagguagua guuugugcug u                                    21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
uagcagcaca uaaugguuug ug                                   22

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
uagcagcaca ucaugguuua ca                                   22
```

```
<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
uagcagcacg uaaauauugg cg                                           22

<210> SEQ ID NO 12
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
acugcaguga aggcacuugu                                              20

<210> SEQ ID NO 13
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
caaagugcuu acagugcagg uagu                                         24

<210> SEQ ID NO 14
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugugcaaauc uaugcaaaac uga                                          23

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
aaaagugcuu acagugcagg uagc                                         24

<210> SEQ ID NO 16
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
uagcuuauca gacugauguu ga                                           22
```

```
<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
aucacauugc cagggauuuc c                                                   21

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
aucacauugc cagggauuac c                                                   21

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
uggcucaguu cagcaggaac ag                                                  22

<210> SEQ ID NO 20
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 20
cauugcacuu gucucggucu ga                                                  22

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uagcaccauc ugaaaucggu u                                                   21

<210> SEQ ID NO 22
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
uagcaccauu ugaaaucagu guu                                                 23

<210> SEQ ID NO 23
<211> LENGTH: 20
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
uagcaccauu ugaaaucggu                                                    20

<210> SEQ ID NO 24
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
uguaaacauc cuacacucuc agc                                                23

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
uauugcacau uacuaaguug c                                                  21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
uauugcacuu gucccggccu g                                                  21

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
ugagguagua aguuguauug uu                                                 22

<210> SEQ ID NO 28
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
aaaagugcuu acagugcagg uagc                                               24

<210> SEQ ID NO 29
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 29
agcagcauug uacagggcua uca                                              23

<210> SEQ ID NO 30
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
uggaguguga caauguguu ugu                                               23

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ucguaccgug aguaauaaug c                                                21

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
ucacagugaa ccggucucuu uc                                               22

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
agugguuuua cccuauggua g                                                21

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
ugagaugaag cacuguagcu ca                                               22

<210> SEQ ID NO 35
<211> LENGTH: 24
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 35
guccaguuuu cccaggaauc ccuu                                           24

<210> SEQ ID NO 36
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
ugagaacuga auuccauggg uu                                             22

<210> SEQ ID NO 37
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ugagaacuga auuccauagg cu                                             22

<210> SEQ ID NO 38
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
uuaaugcuaa ucgugauagg gg                                             22

<210> SEQ ID NO 39
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
accaucgacc guugauugua cc                                             22

<210> SEQ ID NO 40
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
aacauucauu gcugucggug gg                                             22

<210> SEQ ID NO 41
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 41
caucccuugc augguggagg gu                                              22

<210> SEQ ID NO 42
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
caacggaauc ccaaaagcag cu                                              22

<210> SEQ ID NO 43
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
cccaguguuc agacuaccug uuc                                             23

<210> SEQ ID NO 44
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
uaauacugcc ugguaaugau gac                                             23

<210> SEQ ID NO 45
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cugugcgugu gacagcggcu ga                                              22

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
acagcaggca cagacaggca g                                               21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
```
uugugcuuga ucuaaccaug u     21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
ugauugucca aacgcaauuc u     21

<210> SEQ ID NO 49
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
agcuacauug ucugcugggu uuc     23

<210> SEQ ID NO 50
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugucaguuug ucaaauaccc c     21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gccccugggc cuauccuaga a     21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ucgaucacac aaucaguagc a     21

<210> SEQ ID NO 53
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(46)
<223> OTHER INFORMATION: a, c, g, t, unknown or other

```
<400> SEQUENCE: 53
gcgagcacag aattaatacg actcactata ggttttttttt ttttvn               46

<210> SEQ ID NO 54
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (53)..(53)
<223> OTHER INFORMATION: a, c, g, t, unknown or other

<400> SEQUENCE: 54
cgaccttgcg agcacagaat taatacgact cactataggt tttttttttt tvn        53

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (48)..(48)
<223> OTHER INFORMATION: a, c, g, t, unknown or other

<400> SEQUENCE: 55
gacagctcat gacgcacaga cacgactaga gttctttttt tttttvn               48

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (45)..(45)
<223> OTHER INFORMATION: a, c, g, t, unknown or other

<400> SEQUENCE: 56
gacgagctgc ctcagtcgca tagcttgatc gatttttttt tttvn                 45

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
gacgagctgc ctcagtcgca tagcttgatc gatttttttt ttttt                 45

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gcgagcacag aattaatacg ac                                          22
```

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
cgaccttgcg agcacagaat taatacgac                                    29

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gacgtctcat gaggtagtag gttgcatagt t                                 31

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gacgagctgc ctcagtcgca tag                                          23

<210> SEQ ID NO 62
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
ugagguagua gguuguauag uuaaaaaaaa aaaaaa                            36

<210> SEQ ID NO 63
<211> LENGTH: 36
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
ugagguagua gguuguaugg uuaaaaaaaa aaaaaa                            36

<210> SEQ ID NO 64
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 64
agagguagua gguugcauag uaaaaaaaaa aaaaa                             35

-continued

<210> SEQ ID NO 65
<211> LENGTH: 35
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 65
ucgaucacac aaucaguagc aaaaaaaaaa aaaaa                              35

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggtgaggtag taggttgtat agtt                                         24

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gggtgaggta gtaggttgta tagtt                                        25

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gggtgaggta gtaggttgta ta                                           22

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
tgaggtagta ggttgtata                                               19

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ggtgaggtag taggttgtat agtt                                         24

<210> SEQ ID NO 71
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gggtgaggta gtaggttgta ta                                              22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
gggtgaggta gtaggttgta ta                                              22

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tgaggtagta ggttgtgtgg tt                                              22

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gggtgaggta gtaggttgtg                                                 20

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gggtgaggta gtaggttgtg tg                                              22

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
tgaggtagta ggttgtatgg tt                                              22

<210> SEQ ID NO 77
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 77
gtgaggtagt aggttgtatg gtt                                            23

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tgaggtagta ggttgtatg                                                 19

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gggtgaggta gtaggttgta tggtt                                          25

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gggtgaggta gtaggttgta tg                                             22

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gtgaggtagt aggttgtatg                                                20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ggtgaggtag taggttgtat g                                              21

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 83
gtgaggtagt aggttgta                                                    18

<210> SEQ ID NO 84
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ggtgaggtag taggttgta                                                   19

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
agaggtagta ggttgcatag t                                                21

<210> SEQ ID NO 86
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
gggagaggta gtaggttgca tagt                                             24

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
aaaagaggta gtaggttgca tagt                                             24

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
tttagaggta gtaggttgca tagt                                             24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 89
cccagaggta gtaggttgca tagt                                          24

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
gggagaggta gtaggttgca t                                             21

<210> SEQ ID NO 91
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
aaaagaggta gtaggttgca t                                             21

<210> SEQ ID NO 92
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tttagaggta gtaggttgca t                                             21

<210> SEQ ID NO 93
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
cccagaggta gtaggttgca t                                             21

<210> SEQ ID NO 94
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
gggagaggta gtaggttgca tagt                                          24

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
```
gggagaggta gtaggttgca ta 22

<210> SEQ ID NO 96
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 96
agaggtagta ggttgcata 19

<210> SEQ ID NO 97
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 97
gggagaggta gtaggttgc 19

<210> SEQ ID NO 98
<211> LENGTH: 16
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 98
agaggtagta ggttgc 16

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 99
gtgaggtagg aggttgtata gt 22

<210> SEQ ID NO 100
<211> LENGTH: 12
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 100
gggtgaggta gg 12

<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 101
gggtgaggta ggaggttgta ta 22

```
<210> SEQ ID NO 102
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
tgaggtagga ggttgtatag t                                              21

<210> SEQ ID NO 103
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gtgctgaggt agtagattgt atagtt                                         26

<210> SEQ ID NO 104
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gggtgaggta gtaga                                                     15

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gggtgaggta gtagattgta ta                                             22

<210> SEQ ID NO 106
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
tgaggtagta gattgtatag tt                                             22

<210> SEQ ID NO 107
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggtgaggtag tagtttgtac agt                                            23

<210> SEQ ID NO 108
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgaggtagta gtttgtacag t                                              21

<210> SEQ ID NO 109
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ggggtagtag tttgta                                                    16

<210> SEQ ID NO 110
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
ggggtagtag tttgtac                                                   17

<210> SEQ ID NO 111
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
ggggtagtag tttgtaca                                                  18

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
tgaggtagta gtttgtgctg t                                              21

<210> SEQ ID NO 113
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggggtagtag tttgtg                                                    16

<210> SEQ ID NO 114
<211> LENGTH: 17
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 114
ggggtagtag tttgtgc                                                    17

<210> SEQ ID NO 115
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggggtagtag tttgtgct                                                   18

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
tagcagcaca taatggtttg tg                                              22

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gggtagcagc acataa                                                     16

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
tagcagcaca tcatgggttta ca                                             22

<210> SEQ ID NO 119
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
tagcagcacg taaatattgg cgaa                                            24

<210> SEQ ID NO 120
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 120
tagcagcacg taaatattgg cg                                            22

<210> SEQ ID NO 121
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
ggactgcagt gaaggca                                                  17

<210> SEQ ID NO 122
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
ggactgcagt gaaggcac                                                 18

<210> SEQ ID NO 123
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
caaagtgctt acagtgcagg tagt                                          24

<210> SEQ ID NO 124
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
ggtgtgcaaa tctatgcaaa actga                                         25

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
gggtgtgcaa atctatgcaa                                               20

<210> SEQ ID NO 126
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
gggtgtgcaa atctatgc                                                    18

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
gtaaagtgct tatagtgcag g                                                21

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
gggtaaagtg cttatagtgc agg                                              23

<210> SEQ ID NO 129
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
gggtagctta tcagactgat gttga                                            25

<210> SEQ ID NO 130
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
ggtagcttat cagactgatg tt                                               22

<210> SEQ ID NO 131
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
gggtagctta tcagactgat gtt                                              23

<210> SEQ ID NO 132
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132

```
gggtagctta tcagactgat gttga                                            25

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 133
gggatcacat tgccagggat tt                                               22

<210> SEQ ID NO 134
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 134
gggatcacat tgccagggat ttc                                              23

<210> SEQ ID NO 135
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 135
gggatcacat tgccagggat tac                                              23

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 136
gggatcacat tgccagggat ta                                               22

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 137
gggatcacat tgccagggat tacc                                             24

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 138
cattgcactt gtctcggtct ga                                               22
```

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 139
gggtagcacc atctgaaatc g                                         21

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140
gggtagcacc atttgaaatc a                                         21

<210> SEQ ID NO 141
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
tagcaccatt tgaaatcagt gtt                                       23

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
gggtagcacc atttgaaatc a                                         21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
gggtagcacc atttgaaatc g                                         21

<210> SEQ ID NO 144
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
ggtgtaaaca tcctacactc tcag                                      24

```
<210> SEQ ID NO 145
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 145
gggtgtaaac atcctacact ctc                                           23

<210> SEQ ID NO 146
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 146
gggtattgca cattactaag ttgc                                          24

<210> SEQ ID NO 147
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 147
gggtattgca cattacta                                                 18

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 148
tattgcactt gtcccggcct g                                             21

<210> SEQ ID NO 149
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 149
gtgtgaggta gtaagttgta ttgtt                                         25

<210> SEQ ID NO 150
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 150
gggtgaggta gtaa                                                     14

<210> SEQ ID NO 151
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 151
gggtgaggta gtaagttgta tt                                               22

<210> SEQ ID NO 152
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 152
tgaggtagta agttgtattg tt                                               22

<210> SEQ ID NO 153
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 153
aaagtgctta cagtgcaggt agc                                              23

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 154
agtgcttaca gtgcaggtag c                                                21

<210> SEQ ID NO 155
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gagcagcatt gtacagggct atc                                              23

<210> SEQ ID NO 156
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 156
gggtggagtg tgacaatggt gtt                                              23

<210> SEQ ID NO 157
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 157
gggtcgtacc gtgagtaata atg                                            23

<210> SEQ ID NO 158
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gtcacagtga accggtctct ttc                                            23

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
gggtcacagt gaacc                                                     15

<210> SEQ ID NO 160
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 160
gggagtggtt ttaccctatg gtag                                           24

<210> SEQ ID NO 161
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 161
gggtgagatg aagcactgta gctca                                          25

<210> SEQ ID NO 162
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 162
gggtccagtt ttcccaggaa tc                                             22

<210> SEQ ID NO 163
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 163
gggtgagaac tgaattccat gggt                                              24

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 164
gggtgagaac tgaattccat g                                                 21

<210> SEQ ID NO 165
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 165
gggtgagaac tgaattccat aggc                                              24

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 166
gggtgagaac tgaattccat a                                                 21

<210> SEQ ID NO 167
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 167
gggttaatgc taatcgtgat aggg                                              24

<210> SEQ ID NO 168
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 168
gggttaatgc taatcgtg                                                     18

<210> SEQ ID NO 169
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 169
gggttaatgc taatcgt                                                    17

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 170
gggcatccct tgcatggt                                                   18

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 171
cccagtgttc agactacctg ttc                                             23

<210> SEQ ID NO 172
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 172
cccagtgttc agactacctg tt                                              22

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 173
ccagtgttca gactacctgt t                                               21

<210> SEQ ID NO 174
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 174
ggcccagtgt tcagactacc tgttc                                           25

<210> SEQ ID NO 175
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175

```
gggtaatact gcctggtaat gatgac                                              26
```

<210> SEQ ID NO 176
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176

```
gggtgattgt ccaaacgcaa ttct                                                24
```

<210> SEQ ID NO 177
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177

```
ggaccctgag cctatcctag aa                                                  22
```

<210> SEQ ID NO 178
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178

```
gggtcgatca cacaatcagt agca                                                24
```

<210> SEQ ID NO 179
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179

```
gggagaggta gtaggttgca tagtaaaaaa aaaaatcgat caagctatgc gactgaggca         60
gctcgtc                                                                   67
```

<210> SEQ ID NO 180
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180

```
gggtcgatca cacaatcagt agcaaaaaaa aaaaatcgat caagctatgc gactgaggca         60
gctcgtc                                                                   67
```

<210> SEQ ID NO 181
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 181
aaatgaggta gtaggttgta tagtt                                            25

<210> SEQ ID NO 182
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 182
ttttgaggta gtaggttgta tagtt                                            25

<210> SEQ ID NO 183
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 183
ccctgaggta gtaggttgta tagtt                                            25

<210> SEQ ID NO 184
<211> LENGTH: 73
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cgaccttgcg agcacagaat taatacgact cactataggt tttttttttt taactataca     60
acctactacc tca                                                         73

<210> SEQ ID NO 185
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 185
tgaggtagta ggttgtatag tt                                               22

<210> SEQ ID NO 186
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
cgaccttgcg agcacagaat taatacgact cactataggt tttttttttt taactataca     60
acctactacc tcattt                                                      76

<210> SEQ ID NO 187
<211> LENGTH: 76
<212> TYPE: DNA
<213> ORGANISM: Artificial Sequence
<220> FEATURE:
<223> OTHER INFORMATION: Description of Artificial Sequence: Synthetic
```

```
                              -continued
         oligonucleotide

<400> SEQUENCE: 187
cgaccttgcg agcacagaat taatacgact cactataggt tttttttttt taactataca      60
acctactacc tcaaaa                                                      76

<210> SEQ ID NO 188
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cgaccttgcg agcacagaat taatacgact cactataggt tttttttttt taactatgca      60
acctactacc tctggg                                                      76

<210> SEQ ID NO 189
<211> LENGTH: 76
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cgaccttgcg agcacagaat taatacgact cactataggt tttttttttt taactataca      60
acctactacc tcaccc                                                      76
```

METHODS COMPOSITIONS, AND KITS FOR DETECTION OF MICRORNA

BACKGROUND OF THE INVENTION

1. Field of the Invention

The present invention relates to the field of molecular biology. More particularly, the present invention relates to detection of microRNA (miRNA) molecules using homopolymeric tailing, reverse transcription and amplification.

2. Description of Related Art

MicroRNA (miRNA) are small non-protein coding RNA molecules that are endogenously expressed in eukaryotic organisms from fission yeasts to higher organisms. They regulate expression of up to 30% of all genes and play roles in cell differentiation, proliferation, apoptosis, anti-viral defense, and cancer. miRNA have tissue-specific and developmental-specific expression patterns. Thus, these small RNA molecules are of great interest in elucidation of biological processes, disease states, and development.

miRNA are expressed as pol II transcripts as relatively long RNA molecules called pri-miRNA. These pri-miRNA have a 5' cap and a poly-A tail, like other RNA transcripts. The pri-miRNA form hairpin-loop structures in the nucleus, then the hairpin structure is cleaved at the base of the stem by nuclease RNA III Drosha to form double-stranded molecules referred to as pre-miRNA. The pre-miRNA are exported to the cytoplasm by exportin 5, where they are processed by cleavage by Dicer into short (17-25 nucleotide) double-stranded RNA molecules. The strand of the pre-miRNA with less 5' stability then can become bound to the RNA interference silencing complex (RISC) and effect mRNA regulation by binding at the 3' untranslated region (3' UTR) of mRNA having homology to the miRNA (target mRNA) or by directing transport of the mRNA into bodies. Binding results in either cleavage of the target mRNA if there is 100% complementarity between the miRNA and the target RNA (RNA interference) or down-regulation of expression (without cleavage) by binding to the target mRNA and blocking translation or directing mRNA decay that is initiated by miRNA-guided rapid deadenylation if there is less than 100% complementarity between the miRNA and the target RNA. A useful resource for miRNA information is available from the Sanger Institute, which maintains a registry of miRNA at http:/microrna.sanger.ac.uk/sequences/. The miRBase Sequence database includes the nucleotide sequences and annotations of published miRNA from a variety of sources. The miRBase Registry provides unique names for novel miRNA genes that comply with conventional naming nomenclature for new miRNA prior to publication. The miRBase Targets is a resource for predicated miRNA targets in animals. The databases are updated frequently and thus provide a comprehensive source of useful miRNA nucleotide sequences.

miRNA have been found in both coding and non-coding sequences within the genome. They have also been found oriented in both the sense or anti-sense direction with regard to the particular gene in which they are located. Additionally, miRNA may be polycistronic wherein more than one miRNA is in a single mRNA transcript. Expression of miRNA in various cells has been estimated at less than 1,000 copies to more than 500,000 copies.

miRNA family gene expression is regulated spatially and temporally. To assist in the understanding of this regulation, many studies have examined rapidly-evolving *Arabidopsis thaliana* miRNA genes. These miRNA genes arose from a process of genome-wide duplication, tandem duplication, and segmental duplication followed by dispersal and diversification, in processes similar to those that drive the evolution of protein gene families. Multiple expression data sets were examined to study the transcription patterns of different members of the miRNA families. Changes in spatial and temporal expression patterns accompanied the sequence diversification of duplicated miRNA genes suggesting that duplicated copies acquire new functionality as they evolve (Maher, C., L. Stein, D. Ware. 2006. Evolution of *Arabidopsis* microRNA families through duplication events. Genome Res. 16:510-519).

Additional studies in *Caenorhabditis elegans* demonstrated that different miRNA family members may be involved in different physiological functions (Abbott, A. L., E. Alvarez-Saavedra, E. A. Miska, N. C. Lau, D. P. Bartel, H. R. Horvitz, V. Ambros. 2005. The let-7 MicroRNA family members mir-48, mir-84, and mir-241 function together to regulate developmental timing in *Caenorhabditis elegans*, Dev. Cell 9:403-414 and Leaman, D., P. Y. Chen, J. Fak, A. Yalcin, M. Pearce, U. Unnerstall, D. S. Marks, C. Sander, T. Tuschl, U. Gaul. 2005. Antisense mediated depletion reveals essential and specific functions of microRNAs in *Drosophila* development. Cell 121:1097-1108), further emphasizing the importance of discriminating between related miRNA family members.

A systematic evaluation determined the minimal requirements for functional miRNA-target duplexes in vivo (Brennecke, J., A. Start, R. B. Russell, S. M. Cohen. 2005. Principles of microRNA-target recognition. PloS Biol. 3(3):e85). In this study, target sites were grouped into two broad categories. In one category, the mRNA binding site has sufficient complementarity to the miRNA 5' end to function with little or no support from pairing to the miRNA 3' end. In the second category, strong 3' pairing is required for function with inadequate 5' pairing. Both sites are present in biologically relevant genes. Additionally, evidence is presented that an average miRNA has approximately 100 target sites, indicating that miRNAs regulate a large fraction of protein-coding genes and that miRNA 3' ends are key determinants of target specificity within miRNA families. Thus, the differences in nucleotide sequence between the different miRNA family members may be critical to their biological function and the ability to distinguish between highly homologous plant, mammalian, and worm miRNA may be crucial to an accurate understanding of the biological processes regulated by these miRNA.

Studies have shown that differential miRNA expression occurs in cancerous and non-cancerous tissues. miRNA represent 1% of the mammalian genome but more than 50% of miRNA genes are located within regions associated with amplification, deletion and translocation in cancer. It is likely that miRNA present in regions where genomic DNA has been deleted or amplified will not be expressed or be expressed at higher than normal levels, respectively. The expression of miRNA present in regions that are translocated will be governed by the nucleotide sequences in the area that the sequences were translocated to rather than where they were derived.

Differential expression of miRNA in cancerous and normal cells in various solid tumors has been well established. (Lu J., G. Getz, E. A. Miska, E. Alvarez-Saavedra, J. Lamb, D. Peck, A. Sweet-Cordero, B. L. Ebert, R. H. Mak, A. A. Ferrando, J. R. Downing, T. Jacks, H. R. Horvitz, T. R. Golub. 2005. MicroRNA expression profiles classify human cancers. Nature 435:834-838 and Volinia, S., G. A. Calin, C-G. Liu, S. Ambs, A. Cimmino, F. Petrocca, R. Visone, M. Torio, C. Roldo, M. Ferracin, R. L. Prueitt, N. Yanaihara, G. Lanza, A. Scarpa, A. Vecchione, M. Negrini, C. C. Harris, C. M. Croce.

2006. A microRNA expression signature of human solid tumors defines cancer gene targets. Proc. Natl. Acad. Sci. USA 103; 2257-2261). Thus, detection of miRNA expression might be useful in diagnostics, including diagnosis of cancerous conditions. Additionally, miRNA expression might be useful in cancer prognosis and in determining the metastatic potential of tumors and thereby assist in identifying suitable adjuvant treatment.

As an example of highly homologous RNA, many miRNA are grouped into families based upon high sequence homology. In particular, nucleotide positions 2 through 7 from the 5' end are generally 100% homologous. (Lewis, B. P., I-H. Shih, M. W. Jones-Rhoades, D. P. Bartel, C. B. Burge, 2003. Prediction of Mammalian MicroRNA Targets. Cell. 115:787-798). The remaining nucleotides may differ by as few as a single nucleotide. This nucleotide difference may occur at any other position in the miRNA.

The let-7 miRNA family has nine different members with highly homologous nucleotide sequences that may or may not have the same biological function. If they always have the same biological function, it may not be important to have an assay that is able to distinguish between them. While the study of the biological function of miRNA is just beginning, studies suggest that there are likely to be different biological functions associated with highly homologous miRNA.

It is widely known that cells constitutively express housekeeping or infrastructural RNAs. In addition, a wide variety of RNA participating in mechanisms involved in regulation of gene expression at all levels of transmission of genetic information from DNA to proteins are also expressed. The functional roles of noncoding RNA include chromatin structure remodeling, transcriptional and translational regulation of gene expression, regulation of protein function and subcellular distribution of RNA and proteins.

Noncoding transcripts have been identified in organisms belonging to all domains of life. These transcripts include microRNA, snoRNA, housekeeping (infrastructural) RNA (e.g. rRNA, tRNA, snRNA, SRP RNA), and tmRNA, Noncoding RNA include imprinted transcripts (e.g. H19 and Air), dosage compensation transcripts (e.g. Xist mammalian X-inactive specific transcript), stress response transcripts, pal III transcripts, and disease-associated transcripts. Many of the disease-associated transcripts are over expressed in cancers. A database of information on noncoding transcripts can be found at http:(doubleslash)ncrna(dot)rna(dot)net(dot)pl/Browser(dot)html.

RNA interference (RNAi) is an evolutionarily conserved process that functions to inhibit gene expression by means of 21-25 nucleotides of double-stranded RNA (dsRNA) known as small interfering RNA (siRNA) (Fire, A., S. Xu, M. K. Montgomery, S. A. Kostas, S. Driver, C. C. Mello. 1998. Potent and specific genetic interference by double-stranded RNA in *Caenorhabditis elegans*. Nature. 391:806-811). siRNA molecules have potential as therapeutic agents by specific inhibition of expression of preselected proteins and as targets for drugs that affect the activity of siRNA molecules that regulate proteins involved in a disease state. Thus, the ability to accurately quantitate siRNA molecules with high specificity is desirable in monitoring their presence in different cell types in an organism, in particular in response to a defined stimulus or disease state. siRNA are similar to miRNA in their length and composition.

While the methods herein describe the quantitation of miRNA, also contemplated is the application of these methods to the detection of any RNA that lacks a polyA tail or whose detection benefits from the primer design described herein (e.g., siRNA).

A number of techniques have been developed over the last 30 years to detect nucleic acids of interest. Such techniques include everything from basic hybridization of a labeled probe to a target sequence (e.g., Southern blotting) to quantitative polymerase chain reaction (QPCR) to detect two or more target sequences with detection probes or multiple amplification primers, respectively. The polymerase chain reaction (PCR) or more specifically QPCR, is now commonly used in techniques designed to identify small quantities of a target nucleic acid in a sample.

Various techniques have been developed to discover new miRNA and to attempt to quantitate known miRNA in samples or tissues. Many of the studies performed to date have focused on determining the relative levels of miRNA expression. In a common technique, inserts from miRNA are ligated into a vector or to adapter sequences and then the nucleotide sequence is determined. In other techniques, Northern blotting is used to identify expression of miRNA. In general, Northern blotting techniques for studies of miRNA include lysing a cell sample, enriching for low molecular weight RNA, generating a typical Northern blot, hybridizing to a labeled probe which is complementary to a miRNA of interest, and determining the relative molecular weights of detected species to gain a general understanding of the relative amounts of pri-miRNA, pre-miRNA, and miRNA in the original sample.

Studies using Northern blotting typically focus on detection and confirmation of expression of predicted miRNA, and often attempt to quantitate miRNA expression in samples, particularly to determine tissue and time point specific miRNA expression. Studies using Northern blotting have also been performed in attempts to determine ratios of pri-miRNA, pre-miRNA, and miRNA in samples.

In silico predictions are widely used to discover novel miRNA that may be expressed. Computer algorithms have been developed and implemented to identify new miRNA. These in silico methods generally include scanning an organism's genome for sequences that have the potential to form hairpins. Sequences that are identified are then scanned for complementarity to 3' UTR and compared to known homologs. Potential targets are then confirmed by bench experiments, such as through Northern blot experiments.

Microarrays have also been used to detect and measure the relative expression levels of miRNA. In general, microarray methods include spotting oligonucleotides that are complementary to known miRNA sequences on an array, generating fluorescence-labeled miRNA, and exposing the labeled miRNA to the array to determine if any miRNA of interest are present. Microarrays have been used to validate predicted miRNA, to discover homologs of known miRNA, to identify and monitor expression of a given miRNA in a tissue and/or over a time course, and to study miRNA processing.

The detection of miRNA presents unique challenges because of the short template length (19-24 nucleotides), varying G:C content between different miRNA and within the same miRNA nucleotide sequence, and high sequence homology between closely-related family members.

An ideal method of RNA quantitation comprises the following characteristics: high specificity to discriminate between RNA of high nucleotide sequence homology, high sensitivity to detect RNA of varying abundance, linear detection over a broad range of RNA copy numbers, compatible with RNA from a variety of sources (cell lysates, total RNA, samples enriched for small RNA, RNA isolated from FFPE tissue samples), uses the same reaction conditions to detect all RNA to allow for high-throughput and ease of use, and allows for the detection of various classes of RNA in the same sample.

To overcome the short length of miRNA, several methods exist to add additional sequence to a miRNA to facilitate priming and detection. In particular, many add a common sequence to every miRNA to allow for use of a single universal extension primer. In particular, QPCR-based miRNA detection methods add additional sequence to the miRNA to increase its length prior to or during reverse transcription. These methods include the use of a linker primer (Chen, C., D. Ridzon, Z. Zhou, K. Q. Lao, and N. A. Strauss. Methods, Compositions, and Kits Comprising Linker Probes for Quantifying Polynucleotides. U.S. patent application publication number 2006/0078906), use of a RT adapter (Raymond, C. K., B. S. Roberts. P. Garrrett-Engele, L. P. Lim, J. M Johnson. 2005. Simple-quantitative primer-extension PCR assay for direct monitoring of microRNAs and short-interfering RNAs. RNA. 11:1737-1744 and Raymond, C. K. Methods for Quantitating Small RNA Molecules. WIPO patent application PCT/US2006/002591 and direct ligation of an RNA molecule to the 3' end of miRNA (Jacobsen, N., L. Kongsbak, S. Kauppinen, S. M. Echwald, Mouritzen, P. S. Nielsen, D. Norholm. U.S. patent application publication number 2005/0272075). In Sorge, J. A. and R. L. Mullinax (U.S. patent application publication number 2006/0211000), Yeakley, J. M. (Methods and Compositions for Detection of Small Interfering RNA and Micro-RNA), and U.S. patent application publication number 2006/0019258, additional sequence is added by annealing two DNA molecules that exceed the length of the miRNA to a preselected miRNA and ligating to form a long DNA template. In addition, Yeakley generates a labeled miRNA by the use of a phosphate reactive reagent having a label moiety.

In similar methods, additional sequence is added by polyadenylation of the miRNA using *Escherichia coli* polyA polymerase (Shanfa, L., Y.-H. Sun, R. Shi, C. Clark, L. Li, V. L. Chiang. 2005. Novel and Mechanical Stress-Responsive MicroRNAs in *Populus trichocarpa* that Are Absent from *Arabidopsis*. Plant Cell. 17(8): 2186-2203; and Lu, R., V. L. Chiang. 2005. Facile means for quantifying microRNA expression by real-time PCR. 2005. BioTechniques. 39(4): 519-25). An anchored oligo dT primer is annealed to the polyA tail and extended in reverse transcription reaction.

Thus, a short RNA template can be increased in length by the addition of sequence in reverse transcription, ligation, or polyadenylation reactions. While these methods provides a means of increasing the length of the template for QPCR and providing a universal priming site for the reverse primer in QPCR, this addition does not improve the efficiency or specificity of priming in the region of the miRNA.

PCR primer design is critical for the sensitive and specific detection of a target molecule. To this end, many rules have been established and many computer programs which employ these rules are available. These basic rules include ensuring that the melting temperature (Tm) of the PCR primers is above that of the temperature employed in the annealing reaction of the PCR and below that of the temperature employed in the extension reaction of the PCR. While Tm calculations which employ the nearest neighbor rules (Zuker, M. 2003. Mfold web server for nucleic acid folding and hybridization prediction. Nucleic Acids Res. 31(13): 3406-3415 and Mathews, D. H., J. Sabina, M. Zuker and D. H. Turner. 1999. Expanded Sequence Dependence of Thermodynamic Parameters Improves Prediction of RNA Secondary Structure. J. Mol. Biol. 288, 911-940) are generally more accurate in predicting the actual Tm, empirical testing is still recommended in initial testing to identify optimal reaction conditions.

Specifically, Shanfa, L. and Lu, R. (above) teach designing primers for the detection of miRNA by designing a forward primer based on the entire miRNA sequence being detected. The guideline given is if the forward primers contains more than three G/C within the five 3'-end nucleotides, one or two adenines are added to the 3' end of these primers to ensure their binding to the target site encompassing the miRNA sequence and thymines in the poly(T) adapter (Lu, R., above). According to Lu, the true melting temperature (Tm) of potential primers was then determined experimentally by annealing the primer to its complement and generating a thermal dissociation curve between 45° C. and 95° C. Lu, R. (above) used this primer design method to distinguish between miRNAs differing by two or more nucleotide sequences using a standard protocol and by one or more nucleotides using a high-stringency amplification. This amplification protocol was developed by annealing templates with no mismatch or one or more mismatches to the PCR primer and identifying a temperature at which all primers with mismatches have a Tm that is lower and the perfectly matched primer has a Tm that is 5° C. higher. While this method may have high specificity, it requires excessive experimentation to evaluate every primer to determine its optimal Tm and results in protocols that require separate amplifications to detect miRNA of different Tms. In addition, the mismatches that were tested did not include G:T or T:T mismatches, which are known to be more difficult to discriminate. Thus, varying annealing and/or extension temperatures alone may not result in single nucleotide discrimination in all cases.

Alternatively, modified nucleotides have been used to develop reagents to detect miRNA in microarray-(Castoldi, M., S. Schmidt, V. Benes, M. Noerholm, A. E. Kulozik, M. W. Hentze, M. U. Muckenthaler. 2006. A sensitive array for microRNA expression profiling (miChip) based on locked nucleic acids (LNA). RNA. 12(5):913-920) and QPCR-based (Raymond, C. K., B. S. Roberts. P. Garrrett-Engele, L. P. Lim, J. M. Johnson. 2005. Simple-quantitative primer-extension PCR assay for direct monitoring of microRNAs and short-interfering RNAs. RNA. 11:1737-1744 and Raymond, C. K. Methods for Quantitating Small RNA Molecules. WIPO patent application PCT/US2006/002591) assays. In these methods, a modified nucleotide, such as locked nucleic acid (LNA) that possess a 2'-O,4'-C methylene bridge in the ribose moiety of the nucleotide (Petersen, M., J. Wengel. 2003. LNA: A versatile tool for therapeutics and genomics. Trends Biotechnol. 21:74-81) is incorporated into a detection molecule. The use of an LNA increases the hybridization affinity of the oligonucleotides that contain LNA bases and are therefore included in the miRNA-specific detection reagents. In Castoldi, et al, the capture molecules on the microarray include one or more LNA bases and in Raymond, et al, the miRNA-specific QPCR primers include one or more LNA-bases. While the microarray-based method was sensitive, the method was unable to distinguish between several of the closely-related let-7 family members with as high as 20% and 30% relative signal between labeled let-7e and let-7b miRNA and a let-7a capture probe, respectively (http://www.exiqon-.com/SEEEMS/26.asp). In addition, while the QPCR-based method had high sensitivity and specificity, high background signal in the absence of template was also observed. This background signal was attributed to primer-dimer formation between the gene specific primer used in reverse transcription and the miRNA-specific primer which included the LNA.

Thus, a method with higher specificity and lower background that more accurately quantitates the amount of miRNA in a test sample is desirable.

Non-templated nucleotide sequences are commonly added to a template during PCR in order to add nucleotide sequences for cloning (e.g., restriction endonuclease recognition sites), add nucleotides encoding a protein used in purification of the protein (e.g., a HIS tag), increase the Tm of the primer to improve priming efficiency in subsequent extension reactions, and to serve as a priming site in subsequent extension reactions.

An example of non-templated addition of nucleotide sequences includes those that occur during natural processes. In particular, retroviruses, for example Moloney Murine Leukemia Virus (MMLV), perform template switches during the synthesis of retroviral DNA. In this process, the MMLV RT begins DNA synthesis on one viral RNA and then switches to a different viral RNA template in a process called intermolecular template switching. Template switching occurs far more frequently between regions of high sequence homology than between non-homologous sequences (Hu W-S, H. M. Temin. 1990. Retroviral recombination and reverse transcription. Science. 250:1227-1233 and Zhang J., H. M. Temin. 1993. Rate and mechanism of non-homologous recombination during a single cycle of retroviral replication. Science. 259:234-238).

Similarly, a template switching mechanism utilizing a 7-methylguanosine CAP structure present on the 5' ends of all eukaryotic mRNAs (U.S. Pat. Nos. 5,962,271 and 5,962,272) forms the basis of a method designed to clone full-length cDNA. In this method, a template switching oligonucleotide having one or more ribonucleotides, wherein at least one of which is GMP, at the 3' end is used to generate full-length cDNA. In this method, an RNA sample is combined with a cDNA synthesis primer to allow annealing of the cDNA synthesis primer to mRNA to produce a primer-mRNA complex; the primer-mRNA complex is incubated under conditions that permit template-dependent extension of the primer to generate an mRNA-cDNA hybrid; and the mRNA-cDNA hybrid and template switching oligonucleotide are contacted under conditions that permit template-dependent extension of the cDNA of the hybrid, such that a 3' end of the cDNA sequence comprises a sequence that is complementary to the template switching oligonucleotide. The added sequence most commonly served as a primer binding site in subsequent extension reactions. Thus, the non-template addition of Cs is used in the addition of the nucleotide sequence of the template switching oligonucleotide to the 3' end of a newly synthesized cDNA during the reverse transcription reaction.

In later research, it was later found that MMLV RT adds a few non-templated nucleotides (primarily C) to the 3' end of a newly synthesized cDNA strand upon reaching the 5' end of the RNA template and was therefore not dependent upon the presence of a 7-methylguanosine CAP structure (Matz, M. D. Shagin, E. Bogdanova, O. Britanova, S. Lukyanov, L. Diatchenko, A. Chenchik. 1999. Amplification of cDNA ends based on template-switching effect and step-out PCR. Nucleic Acids Res. 15:27(6):1558-1560).

U.S. patent application publication number 2006/0051771 discloses a method for tailing and amplifying RNA. More specifically, it discloses a method for increasing the efficiency of tailing a targeted RNA in a sample, where the method comprises altering the secondary structure of the targeted RNA and incubating the targeted RNA in the presence of a tailing enzyme and a nucleotide under conditions that allow tailing of the targeted RNA. Exemplary methods for altering the secondary structure of the targeted RNA include denaturing the targeted RNA, such as by heating or adding a single strand binding protein.

While numerous techniques and reagents are available for detection and analysis of miRNAs, there still exists a need in the art for methods of miRNA detection that have high specificity and sensitivity, have low or no background signal in the absence of template, allow for the detection of hundreds of different miRNA from a single reverse transcription reaction, use the same reaction conditions to detect all RNA to allow for high-throughput and ease of use, and allow for the detection of various classes of RNA in the same sample.

SUMMARY OF THE INVENTION

The present invention provides a system for detecting nucleic acids in a sample. The system has multiple aspects, including methods, nucleic acids, compositions, and kits. In general, the nucleic acids, compositions, and kits comprise materials that are useful in carrying out the methods of the invention or are produced by the methods, and that can be used to detect nucleic acids of interest that are present in samples.

In a first aspect, the invention provides a method of designing primers for amplification of a miRNA of interest, where the miRNA has a specific, known sequence. As used herein, miRNA are those molecules that meet the criteria of the Sanger Institute miRNA Registry (and precursors to those molecules). In general, the method comprises: selecting one or more miRNA with high sequence identity to the miRNA of interest; identifying nucleotide positions where mismatches occur between the sequence of the miRNA interest and one or more other selected miRNA sequences; designing a primer having a 3' end at or within ten bases of a mismatch, where the designed primer avoids ending in a G:T and/or T:T mismatch at the 3' end of the primer; and, if necessary, adjusting the primer sequence to have a Tm of 55-60° C. by adding one or more nucleotides to the 5' end of the primer sequence. Preferably, the 3' end of the primer is at the base where a mismatch occurs, and particularly where the highest level of mismatches (heterogeneity) occurs when multiple or all relevant sequences are aligned. The additional nucleotides added to the 5' end may be any nucleotides, but are preferably guanine nucleotides. It is also preferably that up to three nucleotides are added to the 5' end. The method can further comprise designing and testing up to three or more primers per miRNA to identify the best sequence for specific and sensitive amplification.

In another aspect, the invention provides a method of detecting microRNA (miRNA) molecules, including their precursor miRNAs (pri-miRNA and pre-miRNA), that are present in a sample. Thus, this aspect of the invention provides methods for determining the presence or absence of miRNA molecules in a sample. The method generally comprises using polyadenylation to add a polyA tail to one or more miRNA of interest in a sample; using an adapter primer and reverse transcriptase to make a cDNA copy of the miRNA; and using a miRNA-specific primer and a universal reverse primer to amplify the cDNA copy by PCR; and detecting the PCR product. Stated another way, the method comprises polyadenylating a miRNA of interest; making a cDNA copy of the polyadenylated miRNA; amplifying the cDNA copy using a primer that has been designed to specifically amplify the miRNA of interest; and detecting an amplification product.

One example of the method comprises: combining a sample suspected of containing a miRNA of interest with one or more enzymes capable of polyadenylating nucleic acids to make a mixture; providing adequate time and conditions for polyadenylation of the miRNA to occur if the target miRNA is present in the mixture; combining the mixture with at least one adapter primer and at least one reverse transcriptase to form a second mixture; providing adequate time and conditions for at least one cDNA copy of the miRNA to be made; combining the cDNA with a specific primer for the miRNA of interest and another primer that can prime the opposite strand from the specific primer; providing adequate time and conditions to amplify at least one strand of at least one cDNA molecule; and detecting amplification. The method optionally comprises designing the specific primer based on the sequence of the miRNA of interest, as disclosed herein. It also optionally comprises providing the sample containing or suspected of containing the miRNA of interest.

In an additional aspect, nucleic acids are provided. The nucleic acids are generally nucleic acids that are useful in performing at least one embodiment of the method of detection according to the invention, or are created by practicing at least one embodiment of the method of designing primers according to the invention. The nucleic acids thus may be polyA tail molecules, oligonucleotides used as primers in the reverse transcriptase reaction, oligonucleotide products, amplification primers, miRNA (for use as positive controls), and other nucleic acids that can serve as controls for one or more steps of the method.

In a further aspect, compositions are provided. Typically, the compositions comprise one or more component that is useful for practicing at least one embodiment of a method of the invention, or is produced through practice of at least one embodiment of a method of the invention. The compositions thus may comprise two or more primers according to the invention. They may also comprise a product of the primers. They also may comprise two or more amplification primers, at least one reverse transcriptase, at least one polymerase, and/or one or more detectable labels. In some situations, the compositions may comprise the buffers used in a method of the invention.

In yet another aspect, kits are provided. Kits according to the invention provide at least one component that is useful for practicing at least one embodiment of a method of the invention. Thus, a kit according to the invention can provide some or all of the components necessary to practice at least one embodiment of a method of detection according to the invention. In typical embodiments, a kit comprises at least one container that contains a nucleic acid of the invention. In various specific embodiments, the kit comprises all of the nucleic acids needed to perform at least one embodiment of the method of detection according to the invention.

BRIEF DESCRIPTION OF THE DRAWINGS

The accompanying drawings, which are incorporated in and constitute a part of this specification, illustrate several embodiments of the invention, and together with the written description, serve to explain certain principles or details of various embodiments of the invention.

FIG. 7 depicts a comparison of let-7a miRNA nucleotide sequences to remaining let-7 family member nucleotide sequences.

FIGS. 8A-C depict a method of the invention using let-7a miRNA template. FIG. 8A discloses SEQ ID NOS 62, 54, 62, and 184, respectively in order of appearance. FIG. 8B discloses SEQ ID NOS 185, 184, 67, 189, 181, and 186, respectively in order of appearance. FIG. 8C discloses SEQ ID NOS 182, 187, 183, and 188, respectively in order of appearance.

FIG. 10 depicts a comparison of let-7d miRNA nucleotide sequences to remaining let-7 family member nucleotide sequences.

FIG. 14 depicts relative assay sensitivity using synthetic miRNA templates.

FIG. 16 depicts the effect of addition of Perfect Match to the assay.

DETAILED DESCRIPTION OF VARIOUS EMBODIMENTS OF THE INVENTION

Figure 1:
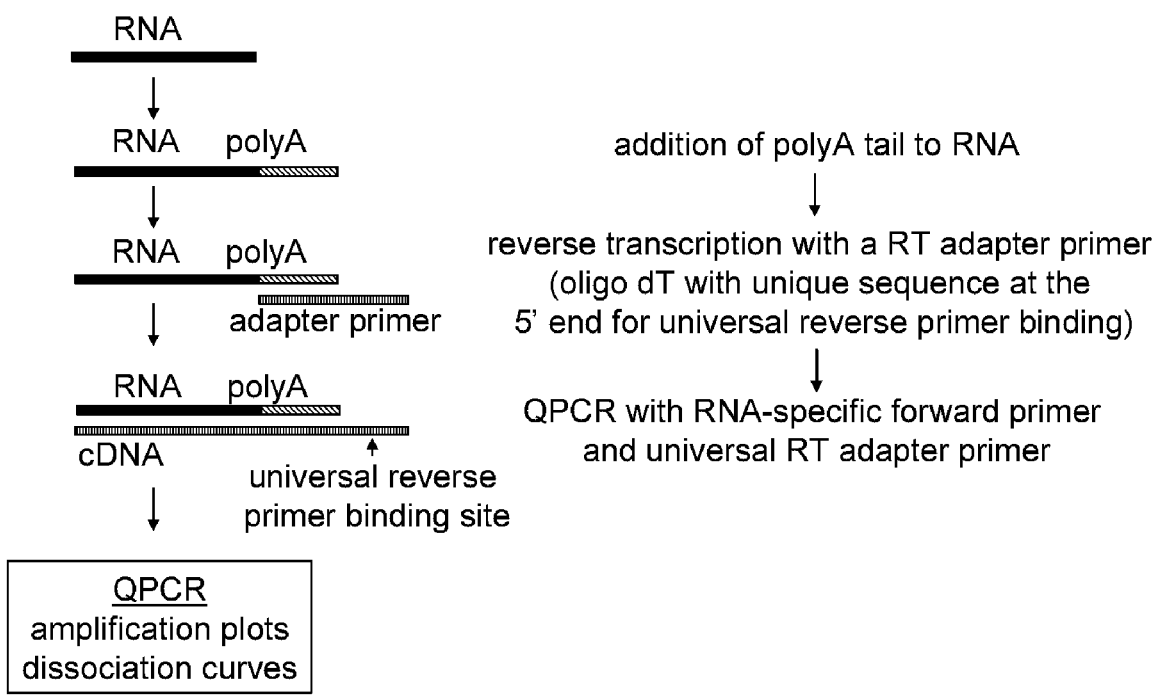
FIG. 1 is a schematic presentation of one method of the invention for detection of miRNA.

Reference will now be made in detail to various exemplary embodiments of the invention, examples of which are illustrated in the accompanying drawings. The following detailed description is provided to give the reader a better understanding of certain features and details of embodiments of the invention, and is not to be understood as a limitation on any aspect or feature of the invention as broadly disclosed herein, depicted in the figures, or claimed.

In recent years, the study of the non-coding class of RNA termed microRNA (miRNA) has grown significantly because of their role in post-transcriptional gene regulation. The identification of novel miRNA sequences has often involved computational approaches, with validation by Northern blot analysis or microarray analysis. Traditional QRT-PCR approaches are difficult to implement for mature miRNA detection because the approximately 22 nucleotide sequences are not of sufficient length for primer extension by the reverse transcriptase followed by detection with QPCR primers of traditional design. Herein we describe an improved polyadenylation, reverse transcription and amplification method for the detection of miRNA sequences. The method utilizes a primer design protocol, the addition of a poly-A tail to miRNA, and reverse transcription using a universal primer that can result in a detectable product or the formation of a template for amplification, such as by QPCR. Potential applications of this technique include, among other things, to quantitate miRNA in a sample de novo or as a method for validation of microarray or Northern blot data.

miRNAs are a class of non-coding RNA sequences that range in length from 17 to 24 nucleotides (nt). There are currently 474 *Homo sapiens* miRNA sequences registered in the Sanger Institute's miRNA Registry Release 9.0. Mature miRNA sequences result from a two-step processing of pri-miRNA transcripts by Drosha to produce the pre-miRNA intermediate, followed by Dicer to form the mature miRNA. In the mature form, the miRNA binds to the 3'-untranslated region (UTR) of mRNA targets to form an RNAi-induced silencing complex (RISC), which can inhibit translation by a number of methods. miRNAs have been linked to several diverse functions, including developmental timing, as well as a number of diseases including cancer.

Several miRNA are only expressed in specific developmental stages or in specific cells. Exemplary embodiments of the present invention relate to a subset of miRNA sequences, whose expression levels are found to vary between normal and cancerous cells, and the development of a system for monitoring their expression. The development of a system for monitoring miRNA expression levels can allow for a better understanding of their biological roles and thereby their potential role in cancer or other diseases or disorders. The correlation between miRNA expression data and its link to disease state in the body may ultimately play a key role in early diagnosis, identifying potential therapeutic targets, development of a treatment plan, monitoring of treatment, and prognosis. While the examples given herein describe a subset of miRNA, detection reagents for any noncoding RNA, including other miRNA is also contemplated.

In one aspect, the invention provides a method of detecting microRNA (miRNA) molecules that are present in a sample. Conversely, the method is a method of determining the absence of a miRNA of interest. The method generally comprises: optionally implementing a primer design protocol; optionally providing a sample containing or suspected of containing a miRNA of interest; adding a polyA tail to the 3' end of the miRNA in the sample if the miRNA is present; combining i) an adapter primer (e.g., a reverse transcription oligonucleotide) that can anneal to the polyA tail, and ii) the sample that might contain the miRNA with an attached polyA tail, resulting in a mixture; exposing the mixture to conditions that permit reverse transcription with a primer to form a cDNA; and detecting the presence or absence of the cDNA, where detection comprises amplification of the cDNA.

Providing, whether it be in reference to primer oligonucleotides, a sample, or any other substance used in the method, can be any act that results in a particular substance being present in a particular environment. Broadly speaking, it can be any action that results in the practitioner obtaining and having in possession the substance of interest in a form suitable for use in the present method (the term "assay" being used herein interchangeable on occasion). Those of skill in the art are aware of numerous actions that can achieve this result. In addition, non-limiting examples are mentioned throughout this disclosure. For example, providing can be adding a substance to another substance to create a composition. It can include mixing two or more substances together to create a composition or mixture. It can also include isolating a substance or composition from its natural environment or the environment from which it came. Providing likewise can include obtaining a substance or composition in a purified or partially purified form from a supplier or vendor. Additionally, providing can include obtaining a sample suspected of containing a miRNA of interest, removing a portion for use in the present method, and maintaining the remaining amount of sample in a separate container from the portion to be used in the present method. Other examples are numerous and will be apparent to those of skill in the art.

Combining substances or compositions in the method means bringing two or more substances, compositions, components, etc. into contact such that a single composition of the two results. Any act that provides such a result is encompassed by this term, and those of skill in the art are aware of numerous ways to achieve the result. A non-limiting example of actions that are considered combining is adding a composition comprising one or more primer oligonucleotides to an aqueous sample containing or suspected of containing a miRNA species. Combining can also include actions that result in the combination being a homogeneous or otherwise mixed composition in which substances of one starting material are interspersed with substances from one or more other starting materials. Thus, combining can include mixing to make a mixture. It can therefore include stirring, repetitive pipetting of the combination, inverting a container containing the combination, shaking the combination, vortexing the combination, or even permitting the combination to stand for a sufficient amount of time for random diffusion to effect partial or complete mixing. Mixing can also include any action that might be required to maintain a homogeneous or nearly homogeneous composition, including, but not limited to performing a new action or repeating one or more actions that resulted in an initial mixture. In a homogeneous assay, poly(A) polymerase, reverse transcription, and QPCR reaction components and RNA sample can be combined in a single tube and incubated under conditions which allows for quantitation of a miRNA. In this method, it may be desirable to prevent alteration of the RT adapter and/or QPCR primers by the poly(A) polymerase. A potential method to prevent this alteration is to use the CleanAmp™ Primers for Improved Hot Start PCR (TriLink Biotechnologies). In these primers, the 3' end is chemically blocked and is not extended until heated at 95° C. for 5-10 minutes.

In situations where the target miRNA is not present in the sample, the polyA tail will not be attached to a target miRNA, the cDNA of the target miRNA will not be made by reverse transcription and no signal or only background signal levels are detected after PCR amplification. Accordingly, in embodiments, the method is a method of determining the absence of a miRNA of interest in a sample. Of course, it is difficult to determine the veracity of a conclusion where the results are negative; however, though use of proper control reactions at one or more points in the assay, a conclusion of lack of miRNA can be drawn with high confidence. As discussed herein, one or more control reactions (positive and/or negative) can be included at each step in the assay to verify proper functioning of reagents and reaction components. Those of skill in the art are well qualified to implement appropriate control reactions without the need for each to be detailed herein.

In embodiments, a cDNA is created by reverse transcription, however, the miRNA-specific primer does not anneal to the cDNA. By does not anneal, it is meant that the amount of annealing that occurs is undetectable or not significantly different than the amount that can be detected in a composition that lacks the miRNA cDNA, but is otherwise identical. The lack of annealing is typically determined by assaying for the presence or absence of an amplification product generated with the miRNA-specific primer. In other embodiments, there is enough complementarity between the miRNA primer and the mRNA target so that annealing occurs between the miRNA-specific primer and the mRNA target during PCR amplification. In this case, signal may be seen. However, the presence of the target miRNA in the sample significantly increases the amount of annealing of the miRNA-specific forward primer to the cDNA above the level that would occur in the absence of the target miRNA. Accordingly, the method of the invention is capable of detecting the presence or absence of a specific miRNA, and can preferably distinguish between miRNA presence and the mere presence of mRNA comprising a similar target sequence.

The method of the invention is also capable of detecting the presence or absence of more than one miRNA species. In other words, although the primers are designed to be specific, the term specific does not imply a one-to-one specificity. Rather, it encompasses binding to all nucleotide sequences that are complementary, at least over a sufficient length to permit hybridization under the conditions used. As the invention is most useful for specific detection of miRNA, typically the hybridization conditions will be set such that complementarity is very high, on the order of 90% or greater over a 10 nucleotide window of contiguous nucleotides. In another example, the complementarity is not as high and can be as low as about 60% over a 10 nucleotide window of contiguous nucleotides. In other embodiments, the complementarity of the primer to the miRNA species may be 60% over less than a 10 nucleotide window, such as a 8 nucleotide window or 60% over more than a 10 nucleotide window.

In embodiments, the method can detect fewer than or about 60 to more than or about 600 different miRNA species in one RNA sample. The high number of different miRNA species that are detected in one RNA sample is because only a small portion of the RT reaction is used as a miRNA template in separate QPCR using different miRNA-specific primers.

The method of the present invention differs from other methods that use a miRNA-specific primer for reverse transcription. For example, in the present invention, a universal primer is used for reverse transcription, which results in cDNA being made from all of the miRNA and mRNA species present. Unlike other methods, one or multiple miRNA-specific primers can then be employed in the PCR amplification step to detect a specific miRNA (or mRNA) or a number of different species of mRNA or miRNA in the sample. The method may also be used to detect the mRNA target and the corresponding miRNA in the same sample.

Those of skill in the art know standard protocols for the addition of polyA tails to RNA molecules. Any suitable technique and set of conditions may be used in practicing the present method. Thus, *Escherichia coli* poly(A) Polymerase I can be employed in this method. For example, the polyA tailing kits which include *E. coli* poly(A) polymerase from Ambion, Epicentre, Invitrogen, and GE Healthcare can be employed to add the adenines to the miRNA. The enzyme used herein may be any enzyme capable of adding a nucleic acid tail to a RNA molecule, including those capable of adding a homopolymeric tail. Various enzymes are capable of synthesizing such tails and include poly(A) polymerases such as *E. coli* poly(A) polymerase I or yeast poly(A) polymerase. Mammalian or viral poly(A) polymerases may also be used. Mutants of poly(A) polymerase with novel properties (Cho, H. D., C. L. Verlinde, A. M. Weiner. 2007. Reengineering CCA-adding enzymes to function as (U,G)- or dCdCdA-adding enzymes or poly(C,A) and poly(U,G) polymerases. Proc. Natl. Acad. Sci. USA 104(1):54-9) are also contemplated. Alternatively, the homopolymeric nucleic acid tail may consist of G, T, or C nucleotides.

Those of skill in the art are also cognizant of numerous techniques for reverse transcription. Any suitable technique and set of conditions may be used in practicing the present method. Thus, any of the following reverse transcriptases, or mutants thereof, may be used (in accordance with conditions known in the art as suitable for reverse transcription activity of the particular reverse transcriptase): avian myeloblastosis virus (AMV); Moloney murine leukemia virus (M-MLV); bovine leukemia virus (BLV-RT); Rouse sarcoma virus (RSV) and human immunodeficiency virus (HIV-RT) and any thermostable DNA Polymerase with reverse transcriptase activity, such as Tth DNA Polymerase. In embodiments, two or more reverse transcriptases may be included in the reaction, each supplying one or more advantageous activities, such as thermostability, specificity for substrate (DNA, RNA, etc.), salt optimum, tolerance for mismatches, and the like.

In embodiments, the reverse transcription reaction includes additional components to increase the efficiency and/or specificity of the reverse transcription. Such additives include, but are not limited to, magnesium chloride, potassium chloride, Triton X-100, single-stranded binding protein and dithiothreitol. Of course, the reverse transcriptase reaction may be performed under different conditions, which result in an increase in reverse transcriptase efficiency and/or specificity. Such conditions comprise variations in annealing temperatures and times prior to and after the addition of the reverse transcriptase.

The method of the invention comprises detecting, often indirectly, the presence of a reverse transcriptase reaction product, such as a cDNA. The cDNA may be one produced from pri-miRNA, miRNA, or mRNA. Detection can be through any technique known in the field of molecular biology for detecting nucleic acids. Thus, it can be through agarose gel electrophoresis and staining with a nucleic acid specific stain. It can be through labeling of one or more of the primers with a detectable moiety, such as a fluorescent or radioactive molecule to produce a labeled product. Likewise, it can be through labeling with a member of a two-component label system, such as the digoxigenin system. Other non-limiting examples include detection based on column chromatography (e.g., size exclusion chromatography), mass spectrometry, and sequencing. Yet other non-limiting techniques include amplification of signal by enzymatic techniques and use of antibodies that are specific to a label attached to one or more nucleotides of the product to be detected. It can also be through real-time monitoring of luminescence/fluorescence as amplification proceeds. Those of skill in the art are well aware of the various techniques for detecting nucleic acids, and the various devices, supplies, and reagents that can be used to do so. Thus, the detection techniques, devices, supplies, and reagents need not be detailed here.

Detection can result in qualitative identification, semi-quantitative identification, or quantitative identification of the target miRNA. Qualitative detection includes detection of the presence or absence of a cDNA or amplification product, without any correlation to an amount of target miRNA in the sample that was tested. Qualitative results enable the practitioner to conclude that the target miRNA was present or absent in the sample, but do not enable him to ascertain the amount. Semi-quantitative detection permits not only detection of a signal, but correlation of the signal to a basal level of target miRNA in the sample that was tested. For example, it may indicate a minimum threshold amount of miRNA was present in the sample. Such a result enables the practitioner to determine if a pre-defined amount of miRNA target is present in the sample, but not to determine if less than that amount is present. Likewise, it does not enable the practitioner to determine the precise concentration or amount of miRNA in the original sample. Quantitative detection permits the practitioner to determine the amount of target miRNA present in the original sample over a wide range of amounts. In general, quantitative detection compares the amount detected to a reference or standard that is either previously generated (e.g., a standard curve) or generated at the time of the assay for the target miRNA using internal controls. Numerous techniques for performing quantitative and semi-quantitative analyses are known to those of skill in the art, and need not be detailed here. For example, those of skill in the art may consult various commercial products for suitable techniques for performing PCR, QPCR, generating standard curves, and quantitating and validating amplification results.

The method may comprise one or more additional optional steps as well. For example, nucleic acids or other substances can be purified to any extent prior to or at any time during the method, including as part of one or more steps, such as the detecting step. Likewise, inhibitors that might be present in one or more compositions can be removed by purification of the nucleic acids of the invention from the inhibitors. Such purification can be performed between two or more other steps of the method, as described herein (although it is to be understood that the steps described herein are not to be understood as limited in practice to the particular order in which they are presented or discussed). In addition, portions of one or more compositions formed during practice of the method may be removed. These can be used for any purpose, including, but not limited to, performing control reactions to ensure that one or more steps in the method are functioning properly, assaying for one or more substances in the composition to ensure that it is present, preferably in the amount expected, and determining any other reaction parameter of interest.

The method comprises amplification of the cDNA or reverse transcriptase product prior to, or at the time of, detection. Amplification of the cDNA can be performed using any suitable amplification technique, including, but not limited to, PCR and all of its variants (e.g., real-time PCR or quantitative PCR). In embodiments, the method comprises providing at least one amplification oligonucleotide primer, exposing the cDNA, if present, to the amplification primer, and exposing the resulting mixture to conditions that permit amplification of the single cDNA, if present. Preferably, oligonucleotides used for amplification comprise a miRNA-specific forward primer and a universal reverse primer. Therefore, in this case, the universal reverse primer comprises part of the sequence found in the reverse transcription primer (or adapter primer). In other embodiments, the adapter primer used for the reverse transcription reaction can also be employed in the amplification reaction.

The meaning of universal reverse primer in this context is any oligonucleotide sequence that can be used for PCR amplification of at least one miRNA and/or mRNA. The meaning of universal reverse primer is not meant to refer to any specific sequence but is meant to refer to a sequence that will be found in most if not all of the cDNA species produced by reverse transcription. Therefore, the sequence can be found universally in the population of cDNA species. Any specific sequence can be used in the universal reverse primer for PCR amplification.

In embodiments, a primer design protocol is used to determine the sequence of the miRNA-specific forward primer used as an amplification primer. The general method for designing such a primer is discussed above. In embodiments, the method comprises the steps of: identifying other miRNA with high sequence identity or homology to the miRNA of interest; identifying nucleotides within the various sequences with the highest heterogeneity when the sequences are aligned; designing a primer such that the 3' end of the primer is as close to a mismatch as possible, and optionally avoiding guanine:thymine and thymine:thymine mismatches; and, if necessary, adding one to ten guanines on the 5' end of the primer to adjust the Tm to about 50 to about 70 degrees Celsius. In exemplary embodiments, zero to three guanines are added to the 5' end of the primer to adjust the Tm to about 45 to about 65 degrees Celsius. In embodiments, nucleotides other than guanine are added to the 5' end; however, guanine is preferred The addition of the bases, such as guanines, to the 5' end of the primer allows an increase in Tm of the primer to a level that is reasonable for PCR amplification. The addition also allows the Tm of the primer to be varied so that the Tm of the miRNA-specific primer can be matched to the Tm of the universal primer used in the PCR reaction. Also, the addition of the bases increases the efficiency of the first cycle of PCR amplification. A critical event in PCR amplification is the first cycle of amplification when the sequence of the primer may not be an exact match to the sequence in the template nucleic acid. The present method of detection, in using miRNA-specific primers of the invention allows improved efficiency of the first cycle in PCR amplification. Additionally, in using miRNA-specific primers of the invention with the addition of one or more guanines that anneal to the cytosines at the 3' end of the miRNA cDNA through non-templated addition by the RT, allows improved efficiency of the first cycle in PCR amplification. The addition of the bases to the 5' end of the primer to adjust Tm also allows the 3' end of the miRNA-specific QPCR primer to be specifically defined, and thus can allow a miRNA-specific primer to end at or within ten nucleotides of a mismatch at the 3' end when compared to other miRNA species in the family. For a primer that would be too short if the 3' end ended at a mismatch, the primer design protocol allows the primer to be extended at the 5' end and be effective while achieving the desired specificity.

The primer design protocol of the invention has high selectivity and allows PCR amplification to discern miRNAs having as few as one nucleotide difference. Of course, the protocol may discern miRNAs having more than one nucleotide difference in their sequences. The protocol also has high sensitivity and can quantify mRNAs with low copy number, such as to about ten copies of a QPCR template.

The primer design method can be used to design any kind of primer that can amplify miRNA where the 5' end of the primer comprises bases, such as guanine nucleotides, that are not part of the target sequence, i.e., not found naturally in the target sequence. In exemplary embodiments, one, two or three guanines not found naturally in the target sequence can be added to the 5' end of the PCR amplification product.

The method of detection may comprise not identifying other miRNA with high sequence homology to the miRNA of interest if they are already known. That is, primers can be designed to be specific for one (or more) miRNA while specifically excluding other miRNA, based on the choice of 3' end. For example, where two or more bases of high heterogeneity exist, a 3' base can be selected that will exclude detection of a particular miRNA, where selection of one or more other possible 3' end would not exclude detection of that miRNA. As mentioned above, selection of primer sequence can be performed to specifically identify a miRNA from a single species, or to specifically identify a particular sequence, which may be shared by two or more species. A corollary to this concept, which is encompassed by this invention, is selection of primer sequence to specifically exclude one or more miRNA species, while detecting one, two, or more other miRNA (the focus of design being to exclude detection of certain miRNA, rather than on specifically detecting one or more miRNA).

Thus, in embodiments, the method comprises providing a primer design protocol for design of a miRNA-specific primer; providing a sample that contains or is suspected of containing the specific miRNA of interest; adding a polyA tail to the 3' end of the miRNA, if present; exposing a mixture comprising an adapter primer or oligonucleotide and the sample containing or suspected of containing a miRNA with an added polyA tail to conditions that permit reverse transcription using the adapter primer to form a cDNA product; and amplifying the cDNA molecule by PCR using a specific forward miRNA primer and a universal reverse primer. Any suitable amount of adapter primer, miRNA-specific forward primer and universal reverse primer may be used. Exemplary concentrations include 0.005 uM, 0.01 uM, 0.1 uM, 0.4 uM, and 0.5 uM. Each primer may be added in a concentration that is independently selected from any other primer. The amount of primer used may also vary depending on the amount of template in the sample. According to the method of the invention, if one or more molecules of a miRNA species of interest (also referred to herein as the "target miRNA") are present in the sample, this exposing results in more than one cDNA product. While theoretically, the method can be practiced with only one copy of each primer, it is envisioned that numerous identical copies of each will be provided each time the method is performed, as is typical for methods performed in the molecular biology field. Thus, reference throughout this disclosure to a certain number of nucleic acids, whether they be adapter primers, reverse transcriptase products, amplification primers, amplification products, or any other nucleic acid, is in reference to the particular identity of the nucleic acid, and encompasses one or multiple exact or essentially exact copies of that nucleic acid.

The amplification primers (universal primer and miRNA-specific primer) may be exposed to the other components of the method at any time during practice of the method. Thus, they may be exposed to the other components before, at the same time as, or after exposure to the reverse transcriptase. Likewise, they may be exposed to the composition after one or more polymerases are exposed to the other components. Accordingly, the method of the invention can be practiced in a single tube format or a multiple tube format (i.e., all reactions can be performed in a single reaction vessel with some or all components being added together, or some reactions can be performed in one reaction vessel and others performed in a second reaction vessel). As with the reverse transcriptase primer, the amplification primers need not be exposed to the other components at the same time, although it is envisioned that they typically will be. The amplification primers may be exposed to the other components of the method after the reverse transcription has occurred. Under certain circumstances, amplification primers can be added multiple times, for example prior to exposing the composition to conditions where amplification may occur, then during the amplification process. Likewise, if a sample is to be removed during practice of the method, amplification primers may be added only to the removed sample, only to the remaining composition, or both. Furthermore, multiple different primers or sets of primers may be added, either to a single composition or to different compositions resulting from removal of one or more portions from the composition. In this way, different amplification efficiencies can be determined based on different amplification primer sequences, or other information can be gathered based on other amplification parameters.

The present invention also provides buffers that comprise a PCR additive, such as one or more selected from the group consisting of: Pfu dUTPase (PEF), PCNA, RPA, ssb, antibodies, DMSO, betaine, 3'-5' exonuclease (e.g., Pfu G387P), Ncp7, recA, and T4gp32, e.g., as described in U.S. patent application publication number 2002/0119467, which is hereby incorporated by reference in its entirety.

In addition, it is expected that general DNA binding proteins will stimulate the processivity of DNA-dependent DNA polymerases, RNA-dependent DNA polymerases, and nucleotidyl transferases. While the methods of the instant invention have been demonstrated with the single-strand DNA binding protein (SSB), other general DNA binding proteins could also be used as stimulators. A non-limiting example of a general DNA binding protein is the gene 32 product of T4 bacteriophage (T4gp32). Hence, it is expected that a number of other general DNA binding proteins will be able to stimulate, for example, RNA-dependent DNA polymerase processivity during reverse transcription when generating cDNA. Non-limiting examples of other general DNA binding proteins, include: ssCRE-BP/Pur.varies. (a protein isolated from rat lung); Hbsu (an essential nucleoid-associated protein from *Bacillus subtilis*); uvs.sup.y (a gene product of bacteriophage T4); replication protein A (a heterotrimeric ss DNA binding protein in eukaryotes); the BALF2 gene product of Epstein-Barr virus; the yeast RAD51 gene product; the SSB of *Bacillus subtilis* phage phi 29; and the SSB of adenovirus (Wei et al., 1998, Ipn. J. Pharmacol. 78: 418-42; Kohler et al., 1998, Mol. Gen. Genet. 260: 487-491; Sweezy et al., 1999, Biochemistry 38: 936-944; Brill et al., 1998, Mol. Cel. Biol. 18: 7225-7234; Tsurumi et al., 1998, J. Gen. Virol, 79: 1257-1264; Namsaraev et al., 1997, Mol. Cell. Biol. 17: 5359-5368; Soengas et al., 1997, J. Biol. Chem. 272: 303-310; and Kanellopoulos et al., 1995, J. Struct. Biol. 115: 113-116).

In addition, non-limiting examples of DNA-dependent DNA polymerases which could benefit from the specificity enhancing methods and compositions of the present invention include *E. coli* DNA polymerase, the klenow fragment of *E. coli* DNA polymerase, Vent polymerase, Pfu polymerase, Bst DNA polymerase, and any other thermophilic DNA polymerase.

In addition, a composition used as a buffer for amplification may also contain additives like antibodies for increased specificity (for hot start PCR, described in Borns et al. (2001) Strategies 14, pages 5-8 and also in manual accompanying commercially available kit, Stratagene Catalogue #600320), DMSO for GC-rich PCR or single stranded DNA binding protein for higher specificity (commercially available, Stratagene Catalog #600201), dUTP and/or uracil N-glycosylase.

One of skill in the art may also employ other PCR parameters to increase the fidelity of synthesis/amplification reaction. It has been reported PCR fidelity may be affected by factors such as changes in dNTP concentration, units of enzyme used per reaction, pH, and the ratio of $Mg^{2+}$ to dNTPs present in the reaction (Mattila et al., 1991, supra). $Mg^{2+}$ concentration affects the annealing of the oligonucleotide primers to the template DNA by stabilizing the primer-template interaction. It also stabilizes the replication complex of polymerase with template-primer. It can therefore also increase non-specific annealing and produce undesirable PCR products (e.g., gives multiple bands in gel or multiple dissociation curves in QPCR). When non-specific amplification occurs, $Mg^{2+}$ might need to be lowered or EDTA can be added to chelate $Mg^{2+}$ to increase the accuracy and specificity of the amplification.

Other divalent cations such as $Mn^{2+}$ or $Co^{2+}$ can also affect DNA polymerization. Suitable cations for each DNA polymerase are known in the art (e.g., in DNA Replication 2nd edition, above). Divalent cation can be supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer can be for $MnCl_2$ from 0.5 to 7 mM, preferably, between 0.5 and 2 mM, and for $MgCl_2$ from 0.5 to 10 mM. Usable cation concentrations in a Bicine/KOAc buffer can be from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration can be, among other things, between 1 and 200 mM, preferably the concentration is between 40 and 100 mM, although the optimum concentration might vary depending on the polymerase used in the reaction.

Deoxyribonucleotide triphosphates (dNTPs) can be added as solutions of the salts of dATP, dCTP, dGTP, dUTP, and dTTP, such as disodium or lithium salts. In the present methods, a final concentration in the range of 1 uM to 2 mM each is suitable, and 100-600 uM is preferable, although the optimal concentration of the nucleotides may vary in the PCR reaction depending on the total dNTP and divalent metal ion concentration, and on the buffer, salts, particular primers, and template.

dNTPs chelate divalent cations, therefore amount of divalent cations used might need to be changed according to the dNTP concentration in the reaction. Excessive amount of dNTPs (e.g., higher than 1.5 mM) can increase the error rate and possibly inhibit DNA polymerases. Lowering the dNTP (e.g., to 10-500 uM) might therefore reduce error rate. PCR reaction for amplifying larger size template might need more dNTPs.

One suitable buffering agent is Tris-HCl, preferably pH 8.3, although the pH may be in the range 8.0-8.8. The Tris-HCl concentration is from 5-250 mM, although 10-100 mM is most preferred. A preferred buffering agent is Bicine-KOH, preferably pH 8.3, although pH may be in the range 7.8-8.7. Bicine acts both as a pH buffer and as a metal buffer. Among other buffers, Tricine may also be used.

PCR is a very powerful tool for DNA amplification and therefore very little template DNA is needed. However, in some embodiments, to reduce the likelihood of error, a higher DNA concentration may be used, though too many templates might increase the amount of contaminants and reduce efficiency.

Usually, up to 3 uM of primers may be used, but high primer to template ratio can result in non-specific amplification and primer-dimer formation. Therefore, it is usually necessary to design primer sequences to avoid primer-dimer formation.

Cycling parameters may vary as well. Denaturation time may be increased if template GC content is high. Higher annealing temperature might be needed for primers with high GC content or longer primers. Gradient PCR is a useful way of determining the annealing temperature. Extension time should be extended for larger PCR product amplifications. However, extension time might need to be reduced whenever possible to limit damage to the enzyme. The number of cycles can be increased if the number of template DNA is very low, and decreased if a high amount of template DNA is used.

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by reference). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, above). Others may also be used. The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and Ppi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reaction. EDTA less than 0.5 mM may be present in the amplification reaction mix. Detergents such as Tween-20™ and Nonidet™ P-40 may also be present in the enzyme dilution buffers. A final concentration of non-ionic detergent approximately 0.1% or less is appropriate; however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. Bovine serum albumin (BSA; up to 0.8 ug/ul) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethylamine N-oxide (TMANO) may also be used. Test PCR reactions may be performed to determine optimum concentration of each additive mentioned above.

The invention provides for additives including, but not limited to antibodies (for hot start PCR) and ssb (higher specificity). An alternative method of hot start PCR is to chemically modify the DNA polymerase such that the polymerase has little or no activity until it is activated by heating. The invention also contemplates mutant archael DNA polymerases in combination with accessory factors, for example as described in U.S. Pat. No. 6,333,158 and WO 01/09347 A2, both of which are hereby incorporated by reference in their entireties.

Various specific PCR amplification applications are available in the art (for reviews, see for example, Erlich, 1999, Rev Immunogenet., 1: 127-34; Prediger 2001, Methods Mol. Biol. 160:49-63; Jurecic et al., 2000, Curr. Opin. Microbiol. 3:316-21; Triglia, 2000, Methods Mol. Biol. 130:79-83; MaClelland et al., 1994, PCR Methods Appl. 4:S66-81;

Abramson and Myers, 1993, Current Opinion in Biotechnology 4:41-47; each of which is incorporated herein by references).

The present invention can be used in PCR applications including, but not limited to, i) hot-start PCR, which reduces non-specific amplification; ii) touch-down PCR, which starts at high annealing temperature, then decreases annealing temperature in steps to reduce non-specific PCR product; iii) nested PCR, which synthesizes more reliable product using an outer set of primers and an inner set of primers. It can also be used with RT-PCR, which uses RNA-directed DNA polymerase (e.g., reverse transcriptase) to synthesize cDNAs, which are then used for PCR. This method is extremely sensitive for detecting the expression of a specific sequence in a tissue or cells. It may also be use to quantify mRNA transcripts. Also, multiplex-PCR can be used, in which two or more unique targets of DNA sequences in the same specimen are amplified simultaneously. One DNA sequence can be use as control to verify the quality of PCR. Likewise, Q/C-PCR (Quantitative comparative), which uses an internal control DNA sequence (but of different size) that compete with the target DNA (competitive PCR) for the same set of primers can be used, as can recursive PCR, which is used to synthesize genes. Other procedures include, but are not limited to, asymmetric PCR and in situ PCR.

The sample can contain a miRNA or mRNA (as mentioned above, included in this term are pri-miRNA and pre-miRNA) of interest or no miRNA or mRNA of interest. The method of the invention is capable of determining whether a miRNA or mRNA of interest or a related miRNA or mRNA having identity at the site of hybridization for the miRNA-specific primer is in the sample or not. Thus, the method can be a method of determining the presence or absence of an miRNA of interest in a sample. As discussed above, if the target miRNA is present in the sample, a cDNA will be made during the reverse transcriptase reaction and an amplification product will be formed during PCR amplification. In the absence of the target miRNA, no cDNA will be produced, and no or an insignificant amount of PCR product will be detected.

Because the method is designed not to detect a miRNA of interest when it is not present in the sample, the practitioner might desire to perform one or more control reactions to ensure that one or more steps of the method are performed properly and/or one or more substance, component, reagent, etc. is functioning as expected. Thus, the method of the invention may optionally comprise one or more control reactions, either performed internally as part of the method in the reverse transcription and/or amplification composition, or as one or more separate reactions performed in addition to the reactions encompassed by the general method of the invention. Thus, for example, the sample may be exposed to a miRNA of known identity (but typically a different species than the target miRNA) and amplification oligonucleotides that are specific for the known miRNA species. Reverse transcription and amplification may be performed with those control nucleic acids present to ensure that the method functioned properly, and that any lack of detectable signal from the target miRNA is due to a lack of that miRNA in the original sample, rather than due to a failure of one or more steps of the method. In a similar fashion, a known miRNA species may be detected by reverse transcription and amplification in a separate reaction vessel that is otherwise treated identically to the reaction vessel containing the sample being tested, to monitor the functioning of the method. Other controls that are known by those of skill in the art as useful in performing reverse transcription and/or amplification reactions may be used as well. Such controls are well known to those of skill in the art, and thus need not be detailed here. Exemplary negative controls can be used to determine the basal level (i.e., background level) of reverse transcription (e.g., in the absence of miRNA target, the absence of any nucleic acids in a sample, the absence of reverse transcriptase, etc.) or basal level of amplification (e.g., in the absence of reverse transcription oligonucleotides to form the cDNA product, the absence of one or more amplification primers, the absence of polymerase, etc.). One may select the positive or negative controls as desired or dictated by the particular embodiment being practiced or sample being tested. Such a selection is well within the skill level of those of skill in the art.

The sample is any sample from any source that contains or is suspected of containing a miRNA of interest. It thus may be a sample from an animal, plant, virus, or fission yeast. It can be an environmental sample, a clinical sample, a laboratory sample, or a sample from an unknown source. Likewise, a sample can be one that derives from two separate sources, which were combined to create a single sample. Combining or pooling of samples may be preferred when the method of the invention is practiced to screen a large number of samples at one time (e.g., high throughput screening). In such situations, pooling permits multiple samples to be assayed in a single reaction vessel. If a positive result is obtained, the individual samples of the pool may later be individually screened by the method to identify the one (or more) samples containing the miRNA of interest.

Additionally, methods resulting in an increase in accessibility of the miRNA for annealing are contemplated by the present invention. In the cell, miRNA might be associated with one or more of the following: one or more proteins, one or more protein complexes, mRNA, target mRNA, small nuclear (snRNA), genomic DNA, cellular membranes, and/or combinations thereof. Such methods to increase miRNA accessibility could include thermal denaturation, protein denaturation and/or removal, and membrane solubilization and/or removal.

The methods of the invention can detect miRNA having a known sequence. They likewise can detect related miRNA, which might or might not have an identical sequence to a known miRNA sequence. Thus, the methods of the invention can be methods of detecting and/or identifying two or more members of a miRNA family or detecting and/or identifying new miRNA species, or detecting and/or identifying miRNA homologs. Typically, when the method is practiced to detect new miRNA species, detection is based on use of amplification oligonucleotides that either have a sequence that is perfectly complementary to a known miRNA species or have a sequence that has high, but not perfect, complementarity to a known miRNA sequence, over a pre-defined region of the miRNA.

Alternatively, the amplification oligonucleotides include one or more positions in which the nucleotide is redundant. By redundant is meant that the nucleotide can be one or more nucleotides comprising G, A, T, or C or any combination thereof. The use of a nucleoside that base pairs with one or more nucleotides, for example inosine, or a modified nucleotide with one or more desired properties are also contemplated. Modified nucleotides having desired properties include those with higher specificity or binding affinity than naturally occurring nucleotides, for example locked nucleic acid (LNA) molecules. LNA refers to a nucleic acid molecule that includes a 2'-O,4'-C-methylene-β-D-ribofuranosyl moiety (Petersen, M., J. Wengel. 2003. LNA: a versatile tool for therapeutics and genomics. Trends in Biotechnol. 21(2):74-81).

miRNA are grouped into family members based upon sequence homology at nucleotide positions 2 to 7 from the 5' end. A method to identify novel miRNA family members therefore contemplates designing a QPCR primer as follows: 1) removing all or most of the nucleotides beginning at the 3' end and ending at position 8 and 2) adding one or more guanines to the 5' end of the QPCR primer. Thus, removing most of the 3' nucleotides that distinguish between the different miRNA family members while retaining the family-specific portion from nucleotide positions 2 to 7 allows for the identification of new miRNA family members. The addition of one or more guanines to the 5' end of the primer allows for increasing priming efficiency in QPCR. Said QPCR primers are then included in a QPCR with cDNA prepared from a RNA sample which may contain novel miRNA family members.

In these cases, detection of the related miRNA can be accomplished by adjusting the amplification reaction conditions to permit hybridization of the amplification oligonucleotides to the cDNA formed by reverse transcription. Accordingly, the methods can detect miRNA having sequences that are 70% or greater identical to a known miRNA sequence at the region of hybridization, such as those having 80% or greater identity, 90% or greater identity 92% or greater identity, or 96% or greater identity (or any whole or fractional percentage within this range). Of course, the amount of identity will be pre-defined based on the sequence of the primer that was designed, and often the amount will be 100% identity over a pre-defined region.

One advantage of the methods of the invention, be they methods of detecting a single miRNA or multiple miRNA having sequence identity, is the ability to monitor expression of certain miRNA across tissue samples or through time. It is known that certain miRNA are expressed in specific tissues or at specific times of development. In some instances, these expression patterns are correlated with disease or disorder states of the individual with which the tissue is associated. By practicing the present invention, progression or status of a disease or disorder may be monitored. Furthermore, monitoring expression of a particular miRNA or multiple miRNAs having a given level of sequence identity can permit the practitioner to identify new tissues that are affected by a certain diseases or disorders. It also can permit the practitioner to determine a new association of a disease or disorder with a miRNA or a miRNA having a certain level of sequence identity. It also can permit the practitioner to identity responses generated by tissues that are present in organisms affected by a disease or disorder. For example, monitoring of apparently healthy tissues along with diseased tissues in a person suffering from a cancer may permit the practitioner to identify cellular responses in both the diseased tissue and the healthy tissue that can be helpful in developing a treatment, or in understanding the response an organism mounts when confronted with a disease state.

In preferred embodiments, the miRNA are isolated from cells, a polyA tail is added to the 3' ends of the miRNA, and the miRNA is detected by the reverse transcription-PCR amplification assay of the invention. The most commonly used method is to co-purify the miRNA with total RNA using a combination of acidified phenol and guanidine isothiocyanate using care not to remove the highly-soluble short RNA (see, for example, Pfeffer, S., Lagos-Quintana, M. & Tuschl, T. Cloning of Small RNA Molecules in Current Protocols in Molecular Biology (eds Ausubel, F. M. B. R. et al.) Ch. 26.4.1-26.4.18 (Wiley Interscience, New York, 2003). This method isolates total RNA, which comprises transfer RNA (tRNA), ribosomal RNA (rRNA), polyA messenger RNA (mRNA), short interfering RNA (siRNA), small nuclear RNA (snRNA), and microRNA (miRNA). If desired, miRNA can be enriched from the total RNA by size selection using gel purification (Pfeffer, S., ibid.).

Alternatively, the miRACLE™ miRNA Isolation Kit (Stratagene), which employs organic extraction followed by purification on a silica-based matrix in a spin-cup format using specialized binding and washing solutions, can be used to enrich for either long RNA or RNA of around less than 200 nucleotides. The resulting RNA preparation (less than 200 nucleotides) is enriched for miRNAs, siRNAs, and/or snRNAs.

In addition, the Absolutely RNA® Miniprep Kit (Stratagene), which employs the traditional guanidine thiocyanate method and a silica-based matrix in a spin-cup format, is used to isolate total RNA comprising miRNA. Following lysis and homogenization of the tissue or cultured cells in lysis buffer, the sample is passed through a pre-filter by centrifugation to remove particulates and most of the DNA contamination. The clarified homogenate is mixed with an organic solvent and applied to the silica-based matrix RNA binding spin cup. After the RNA is washed, any bound DNA is optionally hydrolyzed by DNase digestion. An additional wash removes the DNase, hydrolyzed DNA, and other impurities, and the RNA is eluted from the spin cup with a low ionic strength buffer. The removal of DNA from the total RNA is a beneficial step as the genomic DNA includes the sequences that are transcribed and processed in miRNA. Complete removal of genomic DNA is desirable as its presence in the total RNA could lead to false or misleading results. While this method is not designed to isolate small RNA (<100 nucleotides), it has been found that there is a significant amount of miRNA in the resulting RNA preparation. This is likely due to the interaction between a miRNA and its target mRNA resulting in their co-isolation.

In alternative embodiments, the miRNA are detected in a cell lysate without prior isolation or enrichment for small RNA, including miRNA. Such a method would allow for the polyadenylation, reverse transcription, and PCR amplification assay and not allow for RNA degradation. Suitable methods include lysis and RNA stabilization provided by the use of SideStep™ Lysis and Stabilization Buffer (Stratagene).

In one exemplary embodiment, the method of the invention comprises providing a sample containing or suspected of containing a miRNA, adding a polyA tail to a miRNA species if present to form a miRNA with a polyA tail, providing an adapter primer for reverse transcription that anneals to the polyA tail, providing a reverse transcriptase, combining the adapter primer, the sample that may contain a miRNA species with the polyA tail, and the reverse transcriptase to make a mixture, exposing the mixture to conditions that allow at least a single cDNA product to form, exposing the cDNA, if present, to a universal reverse primer and a miRNA-specific forward primer, exposing the mixture to conditions that permit amplification of the cDNA, if present, and detecting the presence or absence of amplification product.

The method of the invention can detect as few as 1,000 copies of a miRNA in a sample. This result compares very favorably against the known copy number of miRNA in various cells, which is reported to range from a few to more than 500,000. Thus, the method of the invention can detect miRNA from as few as one cell. Typically, a sample will contain cell lysates or purified cell components from many cells (e.g., millions of cells); thus, the method of the invention is well suited for detection of miRNA from typical samples. Of course, parameters for detection may be adjusted to suit the individual practitioner's desires for speed and sensitivity.

Therefore, while the method of the invention is capable of detecting as few as 1,000 miRNA molecules in a cell sample, it may also be used to detect more, such as 50,000 molecules, 100,000 molecules, 250,000 molecules, 500,000 molecules, 1,000,000 molecules, or more. Likewise, while the method is capable of detecting a miRNA of interest in as few as one cell (or a lysate made therefrom), it can also detect a miRNA in a sample of many cells (or lysates therefrom), such as 10 cells, 100 cells, 1,000 cells, 10,000 cells, 50,000 cells, 100,000 cells, 500,000 cells, 1,000,000 cells, 10,000,000 cells, or more. As will be evident to those of skill in the art, the present method can detect any specific number of molecules of miRNA or cells within the range of these exemplary numbers, and thus, each particular number need not be stated.

In another aspect of the invention, nucleic acids are provided. The nucleic acids are generally nucleic acids that are useful in performing at least one embodiment of the method of detection according to the invention, or are created by at least one embodiment of the method of designing a primer according to the invention. The nucleic acids thus may be polyA tail molecules, reverse transcription oligonucleotides (adapter primers), amplification primers, cDNA molecules (e.g., amplification templates), miRNA (for use as positive controls), RNA oligonucleotides having a polyA tail (RT template controls), and other nucleic acids that can serve as controls for one or more steps of the method. Of course, in embodiments, the nucleic acid is a primer according to the invention.

The first class of nucleic acids provided by the invention are polyA tail molecules. The number of adenines in the polyA tail can vary from about 5 to about 1000. In embodiments, the tail comprises about 20 to about 300 adenines, such as from about 20 to about 200, from about 50 to about 150, and any other range not specifically stated. The nucleic acids in this class include molecules comprising the poly adenines and the miRNA after the polyA tail is added, as discussed above.

The second class of nucleic acids provided by the invention are reverse transcription oligonucleotides (adapter primers). Reverse transcription oligonucleotides are oligonucleotides of any suitable length that can hybridize under appropriate conditions to a target miRNA. The reverse transcription oligonucleotides of the present invention can comprise a region that is complementary, either completely or partially, to the polyA tail found at the 3' end of the target miRNA. The reverse transcription oligonucleotides anneal to the polyA tail and are extended by polymerization. Alternatively or in addition, the primer can comprise a PCR priming site (or a sequence complementary to a PCR priming site). Alternatively or in addition, the adapter primer also comprises a spacer region between the PCR priming site (or complement) and the polyA tail.

Various methods are available to estimate the melting temperature (Tm) of the adapter primer (or other primers of the invention) to the target miRNA in reverse transcription and the forward and reverse primer to the cDNA in PCR amplification. The Tm is the temperature at which 50% of the nucleotide sequence and its perfect complement are in duplex. These methods apply to estimating the Tm of DNA:DNA hybrids, of RNA:RNA hybrids, and of DNA:RNA hybrids. The methods of estimating the Tm for DNA:DNA hybrids range from the crude estimation given by 2° C. for each A:T and 4° C. for each G:C (Wallace, R. B., J. Shaffer, R. R. Murphy, J. Bonner, T. Hirose, and K. Itakura, 1979. Nucleic Acids Res. 6, 3543) to the nearest neighbor method used by Mfold (Zuker, M. 2003. Mfold web server for nucleic acid folding and hybridization prediction. Nucleic Acids Res. 31(13): 3406-3415 and Mathews, D. H., J. Sabina, M. Zuker and D. H. Turner. 1999. Expanded Sequence Dependence of Thermodynamic Parameters Improves Prediction of RNA Secondary Structure. J. Mol. Biol. 288, 911-940). Mfold is based on the effect of the nucleotide sequence and is considered to be the most accurate method of estimating Tm.

More recently, methods have been developed to estimate the Tm of DNA:RNA hybrids for use in anti-sense technology (Sugimoto, N., S. Nakano, M. Katoh, A. Matsumura, H. Nakamuta, T. Ohmichi, M. Yoneyama, and M. Sasaki. 1995. Thermodynamic parameters to predict stability of RNA/DNA hybrid duplexes. Biochemistry. 34(35):12,211-12,116; Gray, D. M., 1997. Derivation of nearest-neighbor properties from data on nucleic acid oligomers. II. Thermodynamic parameters of DNA:RNA hybrids and DNA duplexes. Biopolymers. 42(7):795-810) and Le Novere, N., 2001. MELTING, computing the melting temperature of nucleic acid duplex. Bioinformatics. 17(12):1226-1227). When the stability of RNA:RNA, RNA:DNA, and DNA:DNA were compared, the most stable duplex was RNA:RNA. Whether the RNA:DNA or DNA:DNA duplex was more stable was dependent upon the nucleotide sequence. This sequence dependence is considered when calculating the Tm of DNA:RNA based using the nearestneighbor method http:(doubleslash)bioweb(dot)pasteur(dot)fr(slash)seqanal(slash)interfaces(slash)melting(dot)html). The nearestneighbor equation for DNA and RNA-based oligos is: (1) $Tm=(1000\Delta H/A+\Delta S+R\ln(C/4))-273.15+16.6\log[Na+]$ (For DNA see: Breslauer, K, J., R. Frank, H. Blocker, L. A. Marky, 1986. Proc. Natl. Acad. Sci. USA 83:3746-3750 and for RNA see: Freier, S. M., R. Kierzek, J. A. Jaeger, N. Sugimoto, M. H. Caruthers, T. Neilson, D. H. Turner, 1986. Proc. Natl. Acad. Sci. 83:9373-9377) $\Delta H$ (Kcal/mol) is the sum of the nearest-neighbor enthalpy changes for duplexes. A is a constant containing corrections for helix initiation. $\Delta S$ is the sum of the nearest-neighbor entropy changes. R is the Gas Constant (1.99 cal K-1 mol−1), and C is the concentration of the oligonucleotides. Exemplary $\Delta H$ and $\Delta S$ values for nearest neighbor interactions of DNA and RNA are shown in Table 1. In many cases this equation gives values that are no more than 5° C. from the empirical value. It is good to note that this equation includes a factor to adjust for salt concentration.

TABLE 1

Thermodynamic parameters for nearest-neighbor melting temperature formula

| | DNA | | RNA | |
|---|---|---|---|---|
| Interaction | $\Delta H$ | $\Delta S$ | $\Delta H$ | $\Delta S$ |
| AA/TT | −9.1 | −24.0 | −6.6 | −18.4 |
| AT/TA | −8.6 | −23.9 | −5.7 | −15.5 |
| TA/AT | −6.0 | −16.9 | −8.1 | −22.6 |
| CA/GT | −5.8 | −12.9 | −10.5 | −27.8 |
| GT/CA | −6.5 | −17.3 | −10.2 | −26.2 |
| CT/GA | −7.8 | −20.8 | −7.6 | −19.2 |
| GA/CT | −5.6 | −13.5 | −13.3 | −35.5 |
| CG/GC | −11.9 | −27.8 | −8.0 | −19.4 |
| GC/CG | −11.1 | −26.7 | −14.2 | −34.9 |
| GG/CC | −11.0 | −26.6 | −12.2 | −29.7 |
| | 0.0 | −10.8 | 0.0 | −10.8 |

While these methods are useful in estimating the Tm of duplexes, a method to empirically determine the Tm of the duplexes of this invention is also useful. A common method is to use a temperature-controlled cell in a UV spectrophotometer and measure absorbance over a range of temperatures. When temperature is plotted vs. absorbance, an S-shaped curve with two plateaus is observed. The temperature reading halfway the plateaus corresponds to the Tm. Alternatively, a thermocycler such as the MX3000P with samples comprising a nucleic acid dye that binds double-stranded nucleic acid with higher affinity than single-stranded nucleic acid, such as SYBR Green (Molecular Probes), is used to generate the plot with temperature vs. absorbance.

It is to be noted at this point that each value stated in this disclosure is not, unless otherwise stated, meant to be precisely limited to that particular value. Rather, it is meant to indicate the stated value and any statistically insignificant values surrounding it. As a general rule, unless otherwise noted or evident from the context of the disclosure, each value includes an inherent range of 5% above and below the stated value. At times, this concept is captured by use of the term "about". However, the absence of the term "about" in reference to a number does not indicate that the value is meant to mean "precisely" or "exactly". Rather, it is only when the terms "precisely" or "exactly" (or another term clearly indicating precision) are used is one to understand that a value is so limited. In such cases, the stated value will be defined by the normal rules of rounding based on significant digits recited. Thus, for example, recitation of the value "100" means any whole or fractional value between 95 and 105, whereas recitation of the value "exactly 100" means 99.5 to 100.4.

In view of the fact that the miRNA-specific forward primer may comprise a sequence that can hybridize with a target sequence on a cDNA produced from a miRNA of interest, but that might not show 100% identity with that target sequence, it is evident that the miRNA-specific forward primer can hybridize with cDNA sequences produced from other miRNA, such as miRNA that are related to the miRNA of interest. Accordingly, the miRNA-specific forward primer can be used to identify unknown miRNA that have a certain level of sequence identity with a known miRNA. Likewise, the miRNA-specific forward primer and/or the hybridization conditions can be adjusted such that the miRNA-specific forward primer binds to and detects two or more members of the same miRNA family. In this way, a general understanding of the extent to which family members are present in a sample can be gained. In such a situation, if the practitioner desires to identify the individual members of the family that have been detected, hybridization conditions may be adjusted, or the sequence of the miRNA-specific primer may be modified. In silico nucleotide sequence comparisons between miRNA made using ClustalW (Higgins D., J. Thompson, T. Gibson, J. D. Thompson, D. G. Higgins, T. J. Gibson. 1994. CLUSTAL W: improving the sensitivity of progressive multiple sequence alignment through sequence weighting, position-specific gap penalties and weight matrix choice. Nucleic Acids Res. 22:4673-4680) assist in designing primers to detect one or more miRNA.

Intra- and inter-molecular interactions within and between the adapter primer, the cDNA product of the reverse transcription, the miRNA template, and the PCR primers can result in undesirable side reactions. Intra-molecular interactions are estimated using programs such as Mfold (version 3.1) (Zuker, M., above), which uses the nearest neighbor energy rules to assign free energies to loops rather than to base pairs. Inter-molecular interactions are estimated using common primer design programs such as Primer Designer 4.0 (Sci Ed Central). One of skill in the art can select criteria based on the level of specificity desired.

In silico nucleotide sequence comparisons between potentially useful sequences and published human genomic DNA can be made using BLAST (Altschul, S. F., Gish, W., Miller, W., Myers, E. W. and Lipman, D. J. 1990. Basic local alignment search tool. J. Mol. Biol. 215:403-410). While this method is useful, it has been found that a QPCR using the potentially useful sequence and genomic DNA or cDNA from the organism of interest as template (for example, human genomic DNA) be performed to validate the in silico findings.

In addition to the polyA binding site, the adapter primer may comprise non-binding nucleotides that provide length, and optionally other features. These non-polyA binding nucleotides can be randomly included in the adapter primer or the sequences of such nucleotides can be designed for particular purposes. In embodiments, the non-binding nucleotides are specifically included in one or more particular sequences or in relative amounts of adenine, guanine, cytosine, and thymine (or uracil, depending on the desire of the practitioner) so as to provide binding sites for one or more short oligonucleotides, such as amplification primers or detection probes. In embodiments, it may be desirable to engineer amplification primer binding sites that have similar melting temperatures to the miRNA-specific forward primer used in PCR amplification to facilitate accurate and robust amplification.

The adapter primer may comprise, in addition to polyA binding sequences, sequences that do not provide any sequence-specific function. These are referred to herein at various times as "spacer" or "linker" sequences. These spacer or linker sequences mainly provide length for the adapter primer, and thus can vary widely is length from one oligonucleotide to the next. In general, the adapter primer is about 1 to 250 nucleotides or greater. As a general rule, design of the linker sequences should follow the general considerations for PCR primers (e.g., no significant homology to sequences in the genome of the organism being studied, no significant secondary structure).

In embodiments, the adapter primer thus comprises a spacer sequence to increase the length of the cDNA produced from the reverse transcription. Among the advantages provided by the spacer, the increase in length can provide an efficient template for the QPCR when using SYBR® Green (Molecular Probes) for detection. In embodiments, randomly generated sequences can be added to the adapter primer between the PCR priming site and the polyA annealing sequence. If desired, these can be analyzed for 1) intermolecular interactions using primer design software (Primer Designer 4.0), 2) intra-molecular interactions (Mfold), and 3) homology to the human genome (BLAST). They can also be analyzed for their respective Tm and the identity and/or position of various nucleotides altered to obtain oligonucleotides with suitable characteristics.

Other nucleotide sequences that can be provided on the adapter primer includes, but are not limited to, sequences for binding of detection moieties (e.g., TaqMan binding sequences), sequences for sequence-specific capture probes, sequences for additional amplification probes, restriction endonuclease recognition and/or cleavage sites, and sequences that are known to be recognition or modification sites for nucleic acid modifying enzymes (e.g., methylation sites). The addition of such sequences permit any number of additional pieces of information to be generated during an assay. For example, addition of TaqMan binding sequences permits multiplexing. Thus, in an embodiment, the adapter primer includes a probe-binding region to allow for annealing of a hydrolysis probe having a fluorophore, which can be located at the 5' end of the probe, and a quencher that is either internal or located at the 3' end of the probe (see, for example, Higuchi, R., Fockler, C., Dollinger, G. and Watson, R. Kinetic PCR analysis: real-time monitoring of DNA amplification reactions. 1993. Biotechnology (N Y). 11(9):1026-30 and Holland, P. M., Abramson, R. D., Watson, R. and Gelfand, D. H. Detection of specific polymerase chain reaction product by utilizing the 5'-3' exonuclease activity of *Thermus aquaticus* DNA polymerase. 1991. Proc. Natl. Acad. Sci. USA 88(16): 7276-80). When a hydrolysis probe is used for detection of target miRNA, FullVelocity™ QPCR Master Mix (Stratagene) can be used.

The next class of nucleic acids provided by the invention are cDNA molecules which are a result of reverse transcription. The cDNA molecules may be of any length, but are typically in the range of 35-500 nucleotides in length. In some embodiments, the cDNA molecules are from 60 to 120 nucleotides in length. The cDNA molecule can be detected itself by any number of known techniques, or can serve as a template for amplification, digestion and subcloning, or serve other functions in any other technique in which single-stranded nucleic acids can be used. Thus, in embodiments, the cDNA molecule is a labeled product, containing one or more labels or members of a labeling system at one or more points throughout its sequence. Furthermore, the cDNA molecule may be used for any of a number of other purposes, such as use as a molecular weight or luminescence standard, or a positive control for future practice of the method of the invention to detect the particular target miRNA from which the cDNA was produced.

The next class of nucleic acids provided by the invention are amplification primers. Amplification primers are any oligonucleotides that can function to prime polymerization of nucleic acids from template nucleic acids. Those of skill in the art are well aware of techniques and considerations for producing amplification primers, including sets of primers that function reliably and robustly in conjunction with each other to form a double-stranded nucleic acid product of interest from the same template. In accordance with the present invention, the miRNA-specific amplification primer is designed by the primer design protocol of the invention and is designed in conjunction with the amplification primer binding site of the adapter primer, and vice versa. While it is envisioned that there are advantages to designing unique or different reverse amplification primer sequences (and corresponding binding sites on the cDNA), it is also envisioned that the use of standard amplification primer sequences for the reverse primer, and thus standard amplification binding sequences on the adapter primer, can be advantageous in providing a single, standard amplification procedure that can be consistently be reproduced reliably, or at least can reduce the amount of variation, regardless of the identity of the target miRNA. Thus, in embodiments, the reverse amplification primer is selected from among those known in the art as useful for high fidelity amplification of nucleic acids of 50-500 nucleotides in length. In other embodiments, the reverse amplification primer is generated based on selected sequences present on the cDNA or is randomly generated and tested for suitability and specificity. The forward miRNA-specific primer, of course, is not standard and is designed according to the primer design protocol of the invention.

The reverse amplification primer is designed to bind to the amplification binding site of the adapter primer with high specificity. In embodiments, the reverse amplification primer can be designed to have melting temperatures that are quite high (e.g., 62° C. or above). The length and nucleotide composition of each particular primer is not limited by any factor except that the forward and reverse primer or primers should be selected in conjunction to produce primers that will function acceptably to amplify the cDNA for which the primer was designed, if such a cDNA is present in the composition into which the primer is combined. In embodiments where the cDNA contains one or more regions of secondary structure as a result of the sequences of the cDNA, it is preferred, but not required, that the amplification primers specifically bind to the cDNA at a temperature above the temperature at which the secondary structure of the cDNA melts.

Of course, as is known in the art, the reverse amplification primer can include sequences other than those involved in binding to a target sequence. Thus, it may include, at the 5' end, non-binding nucleotides that can serve any number of functions. Included among the functions are: 1) increase in length of the amplified product as compared to the original template (e.g., to provide nucleotides for restriction endonuclease binding), 2) inclusion of a restriction endonuclease cleavage site, 3) provision of a label or substrate for future labeling, 4) provision of sequence for capture or purification, 5) adjustment of Tm, and 6) any other function contemplated by the practitioner. In summary, the reverse amplification primer, while not limited in length, nucleotide content, or sequence, will typically be 18-30 bases long, contain 40-60% G+C content, have a melting temperature (Tm) of about 52° C. or higher, show no significant homology to genomic sequences of the organism under study, show no significant secondary structures or structures formed between primers (e.g., using Zucker's Mfold program), not have a 3' thymidine, and not have multiple G or C at the 3' end. The main consideration is that the primers function to specifically amplify the cDNA product.

The next class of nucleic acids provided by the invention are amplification products. The amplification products are the products produced from amplifying the cDNA. The amplification products may comprise the same sequence or may be different from the cDNA template. For example, they may be longer, and include labels, substrates for labels, restriction endonuclease binding/cleavage sites, multiple primer binding sites, detection sites, and/or hydrolysis probe binding sites. Likewise, amplification products may be shorter than the cDNA. Amplification products that are shorter than their template cDNA may still contain one or more nucleotide sequences that are not present in the cDNA template, including, but not limited to, restriction endonuclease binding/cleavage sites, primer binding sites, labels or label substrates, detection sites, and/or hydrolysis probe binding sites. The amplification products, in addition to being useful for detection, and thus an indication of the presence or absence of a target miRNA in a sample of interest, can be used in a similar fashion to the cDNA. Thus, among other things, they may be used as controls for reverse transcription reactions, or as controls for detection of miRNA.

Another non-limiting example of a class of nucleic acids provided by the invention are miRNA to be detected in the sample. The present invention relies on the known sequence of particular miRNA to be detected to specifically detect that miRNA, to detect miRNA with sequence identity to the known miRNA, or to design primers to detect the miRNA and/or miRNA having sequence identity to a known miRNA. miRNA molecules can be provided by the invention to serve as, for example, positive controls for reverse transcription, or any other purpose chosen by the practitioner. Numerous miRNA sequences are publicly available, and one of skill in the art may produce any of these using standard molecular biology techniques.

In an additional aspect, the invention provides compositions. Typically, the compositions comprise one or more component that is useful for practicing at least one embodiment of a method of the invention, or is produced through practice of at least one embodiment of a method of the invention. The compositions are not limited in their physical form, but are typically solids or liquids, or combinations of these. Furthermore, the compositions may be present in any suitable environment, including, but not limited to, reaction vessels (e.g., microfuge tubes, PCR tubes, plastic multi-well plates, and microarrays), vials, ampules, bottles, bags, and the like. In situations where a composition comprises a single substance according to the invention, the composition will typically comprise some other substance, such as water or an aqueous solution, one or more salts, buffering agents, and/or biological material. Compositions of the invention can comprise one or more of the other components of the invention, in any ratio or form. Likewise, they can comprise some or all of the reagents or molecules necessary for polyA tail addition, reverse transcription, amplification of the cDNA, or any combination of the above. Thus, the compositions may comprise ATP, magnesium or manganese salts, nucleotide triphosphates, and the like. They also may comprise some or all of the components necessary for generation of a signal from a labeled nucleic acid of the invention. In general, the compositions may be any composition that comprises a nucleic acid of the invention, or that can be used for making or detecting a nucleic acid of the invention.

A composition of the invention may comprise one or more adapter primers and/or amplification primers. The primer may be provided as the major component of the composition, such as in a purified or partially purified state, or may be a minor component. The primer may be any adapter or amplification primer according to the invention, in any number of copies, any amount, or any concentration. The practitioner can easily determine suitable amounts and concentrations based on the particular use envisioned at the time. Thus, a composition according to the invention may comprise a single adapter or amplification primer. It may also comprise two or more adapter or amplification primers, each of which having a different sequence, or having a different label or capability for labeling, from all others in the composition. Non-limiting examples of compositions of the invention that comprise adapter or amplification primers include compositions comprising one or more adapter primer and a sample containing or suspected of containing a miRNA of interest or a miRNA of interest with a polyA tail. Other non-limiting examples include compositions comprising one or more adapter primers, one or more amplification primers, and a sample containing or suspected of containing a miRNA of interest. Still other non-limiting examples include compositions comprising at least one amplification primer, at least one adapter primer, a sample containing or suspected of containing a target miRNA, and a reverse transcriptase, which is capable under the appropriate conditions of producing a cDNA. Yet other non-limiting examples of compositions are those comprising the components listed directly above, and further comprising at least one polymerase, which is capable under appropriate conditions of catalyzing the polymerization of at least one amplification primer to form a polynucleotide. In further non-limiting examples, compositions may comprise one or more amplification primer and a cDNA. Additional non-limiting examples include compositions comprising at least one amplification primer and an amplification product. In embodiments, the compositions comprise two or more amplification primers that are designed to function together to produce a double-stranded nucleic acid amplification product. In certain embodiments, the compositions comprise labels or members of a labeling system. In some embodiments, multiple amplification primers are present in a single composition, some of which being specific for one particular cDNA, others being specific for one or more other cDNA molecules.

Alternatively, a composition of the invention may comprise an amplification product. The amplification product may be any nucleic acid that is derived (or has ultimately been produced) from a target miRNA through practice of the method of the invention. As with other compositions comprising nucleic acids of the invention, compositions comprising an amplification product may comprise it in any number of copies, amount, or concentration. The amplification product may be provided as the major substance in the composition, as when provided in a purified or partially purified form, or may be present as a minority of the substances in the composition. Non-limiting examples of compositions of the invention include compositions comprising an amplification product and a sample containing a target miRNA. Other non-limiting examples include compositions comprising an amplification product and at least two amplification primers. Other non-limiting examples include those in which the composition comprises an amplification product and at least one polymerase. Yet other non-limiting examples include compositions comprising an amplification product and at least one member of a labeling system. Yet other non-limiting examples include compositions comprising an amplification product and at least one reverse transcriptase. Other non-limiting examples include compositions comprising an amplification product and cDNA molecule. Further non-limiting examples include compositions comprising a target miRNA, at least one adapter primer, at least one reverse transcriptase, a cDNA molecule, at least one amplification primer, at least one polymerase, and an amplification product. In embodiments, the composition comprises agarose, polyacrylamide, or some other polymeric material that is suitable for isolating or purifying, at least to some extent, nucleic acids. In embodiments, the composition comprises nylon, nitrocellulose, or some other solid support to which nucleic acids can bind. In some embodiments, the compositions comprise at least one label or member of a labeling system. Two or more different amplification products may be present in a single composition.

Compositions of the invention can comprise one or more nucleotidyl transferases and in particular, polyA polymerases. The polymerase can be any polymerase known to those of skill in the art as being useful for adding a homopolymeric tail to a miRNA. Thus, it can be, for example, *E. coli* polyA Polymerase I. This enzyme is of particular value in this method because of its high processivity, specificity for single-stranded RNA molecules, and its ability to add a polyA tail to a RNA is sequence-independent.

Compositions of the invention can comprise one or more nucleic acid polymerases. The polymerase can be any polymerase known to those of skill in the art as being useful for polymerizing a nucleic acid molecule from a primer using a strand of nucleic acid as a template for incorporation of nucleotide bases. Thus, it can be, for example, Taq DNA polymerase, Pfu DNA polymerase, Pfx DNA polymerase, Tli DNA polymerase, Tfl DNA polymerase, klenow, T4 DNA polymerase, T3 RNA polymerase, T7 RNA polymerase, and SP6 RNA polymerase, or combinations, mutants, or fusion proteins thereof.

Compositions of the invention can comprise one or more buffers. A PCR reaction buffer composition may contain any known chemicals and reagents used in a buffer for PCR reaction. For example, the buffer composition can contain a buffering composition selected from Tris, Tricine, or Bicine. The amount is an amount to provide adequate buffering for reactions, such as from 1 mM to 500 mM, for example 5 mM, 10 mM, 20 mM, 50 mM, 100 mM, 150 mM, 200 mM, or 250 mM. In embodiments, the buffering composition has a pH range of from 6.5 to 9.5, such as from 7.0 to 8.5 or 7.5 to 8.0, for example, 6.8, 7.2, 7.8, 8.2, 8.8, 9.0, or 9.2. A PCR reaction buffer can contain $Mg^{2+}$ (e.g., $MgCl_2$ or $MgSO_4$) in the range of 0.5-20 mM, such as 1 mM, 2 mM, 5 mM, 10 mM, or 15 mM. The buffer may also contain $K^+$ (e.g., KCl) in the range of from 0.1 to 100 mM, such as 0.5 mM, 1 mM, 2 mM, 5 mM, 10 mM, 20 mM, or 25 mM. In some embodiments, the buffer contains components that enhance PCR yield (e.g., $(NH_4)_2SO_4$ in the range of from 0.1 to 50 mM, such as 0.5 mM, 1 mM, 5 mM, 10 mM 20 mM, or 25 mM). In embodiments, the buffer contains one or more non-ionic detergents (e.g., Trition X-100, Tween 20, or Brij®, NP40, in the range of from 0.1% to 10%, such as 0.5%, 1%, or 5%). Alternatively, the buffer contains one or more surfactants (0.0001-10%). The buffer may also contain BSA in the range of from 0.1-500 ug/ml, such as 1 ug/ml, 5 ug/ml, 10 ug/ml, 50 ug/ml, 100 ug/ml, 150 ug/ml, 200 ug/ml, or 250 ug/ml. Of course, any particular value within these ranges will be immediately apparent to those of skill in the art without each particular value needing to be recited specifically herein, and as such, each value is to be understood as having been specifically recited.

Other PCR additives may also affect the accuracy and specificity of PCR reactions. For example, EDTA at less than 2 mM, such as at 1 mM, 0.5 mM, or 0.1 mM or less, may be present in the amplification reaction mix. In addition or alternatively, detergents, such as Tween-20™, Nonidet™ P-40, and Brij® can be present in the enzyme dilution buffers. A final concentration of non-ionic detergent approximately 0.1% or less is appropriate, such as 0.01%-0.1%, for example 0.01%, 0.02%, or 0.05%, which is an amount that should not significantly interfere with polymerase activity. Similarly, glycerol is often present in enzyme preparations and is generally diluted to a concentration of 1-20% in the reaction mix. Glycerol (about 5-10%), formamide (about 1-5%), and/or DMSO (about 2-10%) can be added in PCR reactions for template DNA with high GC content or long length (e.g., >1 kb). These additives can change the Tm (melting temperature) of primer-template hybridization reaction and the thermostability of polymerase enzyme. Betaine (0.1-2M) is also useful for PCR over high GC content and long fragments of DNA. Tetramethylammonium chloride (TMAC, >50 mM), Tetraethylammonium chloride (TEAC), and Trimethlamine N-oxide (TMANO) may also be used. Test PCR reactions may be performed to determine optimum concentration of each additive mentioned above.

The invention provides for additives including, but not limited to antibodies (for hot start PCR) and ssb (single strand DNA binding protein; higher specificity). The invention also contemplates mutant archael DNA polymerases in combination with accessory factors, for example as described in U.S. Pat. No. 6,333,158, and WO 01/09347 A2, hereby incorporated by reference in their entirety.

$Mg^{2+}$ concentration can affect the annealing of the oligonucleotide primers to the template DNA by stabilizing the primer-template interaction, and it also is believed to stabilize the replication complex of polymerase with template-primer. It can therefore also increase non-specific annealing and produce undesirable PCR products (gives multiple bands in gel). When non-specific amplification occurs, $Mg^{2+}$ might need to be lowered or EDTA can be added to chelate excess $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in DNA Replication 2nd edition, supra). Divalent cation is typically supplied in the form of a salt such $MgCl_2$, $Mg(OAc)_2$, $MgSO_4$, $MnCl_2$, $Mn(OAc)_2$, or $MnSO_4$. Usable cation concentrations in a Tris-HCl buffer are for $MnCl_2$ from 0.05 to 20 mM, such as between 0.1 and 10 mM, for example between 0.5 and 2 mM, and for $MgCl_2$ from 0.5 to 10 mM. Usable cation concentrations in a Bicine/KOAc buffer are from 1 to 20 mM for $Mn(OAc)_2$, preferably between 2 and 5 mM.

Monovalent cation required by DNA polymerase may be supplied by the potassium, sodium, ammonium, or lithium salts of either chloride or acetate. For KCl, the concentration is generally between 1 and 200 mM, such as between 40 and 100 mM, although the optimum concentration may vary depending on the polymerase used in the reaction.

Deoxyribonucleoside triphosphates (dNTPs) are added as solutions of the salts of dATP, dCTP, dGTP, dUTP, and dTTP, such as disodium or lithium salts. In the present method, a final concentration in the range of 1 uM to 2 mM each is suitable, and 100-600 uM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 uM of each dNTP may be preferred when using a Tris-HCl buffer.

dNTPs chelate divalent cations; therefore the amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 uM) might reduce the error rate. PCR reactions for amplifying larger size templates may need more dNTPs.

The pH of the buffering component in standard PCR reaction buffers is from 8.3-8.8. However, other pH ranges may be used as appropriate. For example, a different pH range may be required by the particular goals of the amplification process or by an enzyme or any other component of the reaction mixture. In particular, a pH of 8.0 may be required for use with chemically modified polymerases.

In yet another aspect of the invention, kits are provided. Kits according to the invention provide at least one component that is useful for practicing at least one embodiment of a method of the invention. Thus, a kit according to the invention can provide some or all of the components necessary to detect the presence of a miRNA in a sample. In typical embodiments, a kit comprises at least one container that contains a nucleic acid of the invention. In various specific embodiments, the kit comprises all of the nucleic acids needed to perform at least one embodiment of the method of the invention.

Kits are generally defined as packages containing one or more containers containing one or more nucleic acids or compositions of the invention. The kits themselves may be fabricated out of any suitable material, including, but not limited to, cardboard, metal, glass, plastic, or some other polymeric material known to be useful for packaging and storing biological samples, research reagents, or substances. The kits may be designed to hold one or more containers, each of such containers being designed to hold one or more nucleic acids, compositions, or samples of the invention. The containers may be fabricated out of any suitable material including, but not limited to, glass, metal, plastic, or some other suitable polymeric material. Each container may be selected independently for material, shape, and size. Non-limiting examples of containers include tubes (e.g., microfuge tubes), vials, ampules, bottles, jars, bags, and the like. Each container may be sealed with a permanent seal or a recloseable seal, such as a screw cap. One or more of the containers in the kit may be sterilized prior to or after inclusion in the kit.

In certain embodiments, the kit comprises at least one miRNA-specific forward primer. These primers may be provided separately in different containers or together in a single container. Likewise, multiple containers may be provided, each containing at least one miRNA-specific forward primer. In embodiments, the kit comprises multiple different miRNA-specific forward primers, which can be used to detect the presence of two or more different miRNA targets.

In certain embodiments, the kit comprises at least one adapter primer. In various configurations, the adapter primers are provided separately in separate containers or together in a single container. Furthermore, multiple containers containing the various adapter primers and reverse transcriptases can be provided, each independently containing one or more of the primers and reverse transcriptases.

In embodiments, the kit comprises one or more PCR primers. Thus, in embodiments, the kit comprises two PCR primers. In other embodiments, the kit comprises at least one adapter primer, at least one reverse transcriptase, and at least one synthetic miRNA. In yet other embodiments, the kit comprises at least one cDNA, at least one PCR primer (for example, two primers), and at least one polymerase. In yet other embodiments, the kit comprises at least one adapter primer, at least one reverse transcriptase, and at least one miRNA.

In certain embodiments, the kit comprises at least one adapter primer for detection of a particular target miRNA, at least one reverse transcriptase that is capable of producing a cDNA from the particular target miRNA, and at least two amplification primers that can amplify a cDNA. In yet other embodiments, the kit comprises at least one adapter primer for detection of a particular target miRNA, and at least two amplification primers that specifically amplify a cDNA produced from reverse transcription. In various configurations of the kit, at least one polymerase is included.

In certain configurations of the kit, one or more cDNA molecules specific for pre-defined miRNA are provided. These can be used, for example, as positive control reagents for monitoring of the assay. In configurations of the kit, one or more amplification products may be included.

The kit of the invention may include one or more other components or substances useful in practicing the methods of the invention, such as sterile water or aqueous solutions, buffers for performing the various reactions involved in the methods of the invention, and/or reagents for detection of reverse transcription or amplification products. Thus, in embodiments, the kit comprises one or more polymerase for amplification of a cDNA molecule. In embodiments, it comprises one or more reverse transcriptases for cDNA synthesis. It also can comprise some or all of the components, reagents, and supplies for performing reverse transcription and amplification according to embodiments of the invention. In embodiments, it includes some or all of the reagents necessary for performing QPCR.

EXAMPLES

The invention will be further explained by the following Examples, which are intended to be purely exemplary of the invention, and should not be considered as limiting the invention in any way.

Example 1

Details of a 3-Step Assay According to an Embodiment

The 3-step assay described herein consists of three different enzymatic steps, which are generally depicted in FIG. 1. In the first step, the RNA molecule is polyadenylated to add a universal sequence that can be used to direct priming in the next step. In the second step, the polyadenylated RNA molecule is annealed to an adapter primer and the RNA molecule is reverse transcribed to generate complementary DNA (cDNA). The adapter primer comprises a homopolymeric region consisting of dT and a unique sequence at the 5' end that serves as a universal reverse primer binding site in the next step. In the third step, the cDNA is detected with a miRNA-specific QPCR primer and a universal primer.

Example 2

PAP Reactions Using Synthetic RNA Templates to Generate Polyadenylated RNA

For miRNA analysis, polyadenylation (PAP) reactions were performed in 1× E-PAP buffer (Ambion), 0-1 millimolar (mM) adenosine triphosphate (ATP), 0-2.5 mM manganese chloride ($MnCl_2$), 0 to $10^{14}$ copies of a synthetic RNA, 0-20 units (U) RNase Block Ribonuclease Inhibitor (optional; Stratagene), and 0-2 U *Escherichia coli* polyA polymerase (E-PAP; Ambion or Stratagene). PAP reaction components were combined and incubated at 37° C. for 15-60 min. After the incubation period, the PAP reactions were terminated by heating at 95° C. for 5 minutes and stored at 6° C. or −20° C. until further analysis.

Buffer components were varied in different reactions, including positive and negative control reactions. In positive control reactions, all reaction components, including a miRNA template, were included in the reaction. In these reactions, a signal in QPCR was the expected result. In negative control reactions, either the ATP or the E-PAP was commonly omitted. In these reactions, no signal in QPCR was the expected result. In those experiments where a signal was detected in QPCR above 10-100 copies, the experiment was repeated until either no signal or fewer than 100 copies were detected. Only the experiments with an acceptable level of background are described herein.

In addition, it was found that while several manufacturers of E-PAP recommend including $MnCl_2$ in the E-PAP reaction buffer, the omission of $MnCl_2$ did not adversely affect polyadenylation of synthetic miRNA or miRNA in total RNA. The presence of $MnCl_2$ in PCR results in random mutagenesis in a method known as Error-Prone PCR. Thus, omission of $MnCl_2$ in the PAP reaction is desirable when a portion of the E-PAP reaction products are used directly in the reverse transcription reaction and subsequent QPCR to retain the desired QPCR assay specificity.

PAP reaction conditions were analyzed by direct detection of PAP reaction products by gel electrophoresis or by reverse transcription of the PAP products followed by detection of the reverse transcription products by QPCR.

Example 3

Gel Analysis of Polyadenylated RNA

For PAP reaction optimization experiments, PAP reaction products were analyzed by gel electrophoresis. A suitable portion of the PAP reaction product was combined with an equal number of a synthetic DNA oligonucleotide comprising a nucleotide sequence that is complementary to the RNA sequence being detected and an equal volume of Novex® TBE Sample Buffer (2×) (Invitrogen). The samples were incubated at 70° C. for 3 min and stored on ice. The samples were loaded into the wells of a 4-20% (w/v) Novex® TBE Gels (Invitrogen) and the nucleic acids separated by electrophoresis at 180V until the bromophenol blue dye front was ⅔ to ¾ the length of the gel. The nucleic acids were then stained with SYBR Gold (Molecular Probes) and visualized with the Eagle Eye® II System (Stratagene) according to the manufacturer's recommended conditions.

Example 4

PAP Reactions Using RNA Templates from Cells to Generate Polyadenyated RNA

For detection of miRNA and mRNA from cells, PAP reactions were performed as described in Example 2, above. However, the synthetic miRNA template was replaced with 0 to 1 microgram (ug) of total RNA template from a cell. PAP reaction components were combined and incubated at 37° C. for 15-60 min. After the incubation period, the PAP reactions were terminated by heating at 95° C. for 5 minutes and stored at 6° C. or −20° C. until further analysis. It should be noted that the amount of miRNA and mRNA in the RNA samples from cells might vary depending upon the method used for isolation of the RNA sample, and thus particular parameters for a particular sample might vary.

Example 5

Purification of Polyadenylated RNA

For purification of polyadenylated RNA, several methods were used. Purification of the polyadenylated RNA prior to reverse transcription is optional but is useful in removing the E-PAP and buffer components from subsequent reactions. Suitable methods include organic extraction using phenol:chloroform followed by ethanol precipitation, binding to and elution from oligo (dT) such as the oligo (dT) bound to magnetic particles in the Absolutely mRNA™ Purification Kit (Stratagene), or any other method that results in a RNA template that is suitable for reverse transcription.

Example 6

Reverse Transcription of Polyadenylated miRNA to Generate cDNA

For conversion of polyadenylated RNA to complementary DNA (cDNA), reverse transcriptase (RT) reactions were performed in 1×RT buffer, 0-0.5 uM RT adapter primer (Table 2; SEQ ID NO: 53, 54, 55, 56, or 57), 0-100% of the polyadenylation product reaction, and 0-200 U RT. The reactions were incubated at temperatures and times which were appropriate for the RT. The reactions were diluted with RNase-, DNase-free water (Sigma) and stored at 6° C. or −20° C. prior to QPCR analysis. In general, RT products were diluted 1:300 prior to QPCR analysis.

Several reverse transcriptases (RTs) were evaluated during the development of this method. These reverse transcriptases included MMLV RT (Stratagene), StrataScript® Reverse Transcriptase (Stratagene), StrataScript® 5.0 Multiple Temperature Reverse Transcriptase (Stratagene), and AffinityScript™ Multiple Temperature Reverse Transcriptase (Stratagene). All RTs were used with the buffer and reaction conditions recommended by the manufacturer. For example, reactions with AffinityScript™ Multiple Temperature Reverse Transcriptase (Stratagene) were incubated at 50° C. for 5 min, 25° C. for 15 min, 45° C. for 30 min, and 95° C. for 5 min.

The optimal concentration of RT adapter primer varied depending upon the amount of template. For example, when synthetic miRNA were used as the template, a lower amount of RT adapter primer was optimal than when total RNA was used as the template. This difference is likely due to the differences in the amount of polyadenylated template present in synthetic miRNA and total RNA preparations.

Example 7

Determining Effect of Heating and Addition of Perfect Match® PCR Enhancer to Reverse Transcription Reaction Perfect Match® PCR Enhancer (Stratagene) has been shown to increase yield and specificity of primary PCR amplification products, minimize the formation of poorly matched primer-template complexes, and destabilize many mismatched primer-template complexes. While these effects have been demonstrated when using a single-stranded DNA template and DNA primer, the addition of Perfect Match may also have beneficial effects in a reverse transcription reaction with a single-stranded RNA template and DNA primer. In addition, thermal denaturation has been shown to be beneficial in reducing secondary structure that may be found in single-stranded nucleic acids. It was therefore proposed that the addition of Perfect Match and thermal denaturation may enhance reverse transcription.

In order to test any additive for use in this invention, the additive is preferably tested in one or more of the enzymatic reactions. Any additive that has a beneficial effect to the one reaction but has an adverse effect on the subsequent reaction can be removed from the previous reaction by purification prior to its addition to the subsequent reaction. Alternatively, the effect can be reduced by dilution of the previous reaction products prior to addition of a portion of the previous reaction products to the subsequent reaction.

In this example, varying amounts of Perfect Match were added to the reverse transcription reaction using $10^{10}$ copies of the let-7d 14A miRNA template (SEQ ID NO: 64) as described above and in the product literature for Perfect Match. The Perfect Match (1 U/uL) was diluted in water to $8\times10^{-4}$ to $8\times10^{-7}$ U/uL and 1.0 uL was added to a 20 uL RT reaction. The reactions were prepared in quadruplicate. One set of two reactions were incubated at 55° C. for 5 min (template denaturation) while the second set remained on ice. The samples were quickly spun down and AffinityScript® (Stratagene) was added to all samples. All reactions were then incubated at 25° C. for 15 min (primer annealing and extension), 42° C. for 20 min (primer extension), and 95° C. for 5 min (RT denaturation). In subsequent experiments, AffinityScript was added before heating at 50° C. for 5 min to reduce the potential for cross contamination when opening the tubes. While AffinityScript retains most of its activity when incubated at 55° C., more activity is retained at 50° C.; therefore, 50° C. was used in place of 55° C. In addition, AffinityScript has reverse transcriptase activity at 25° C. Incubation at 25° C. is therefore likely to allow for both annealing and extension of the RT adapter primer.

Figure 2:
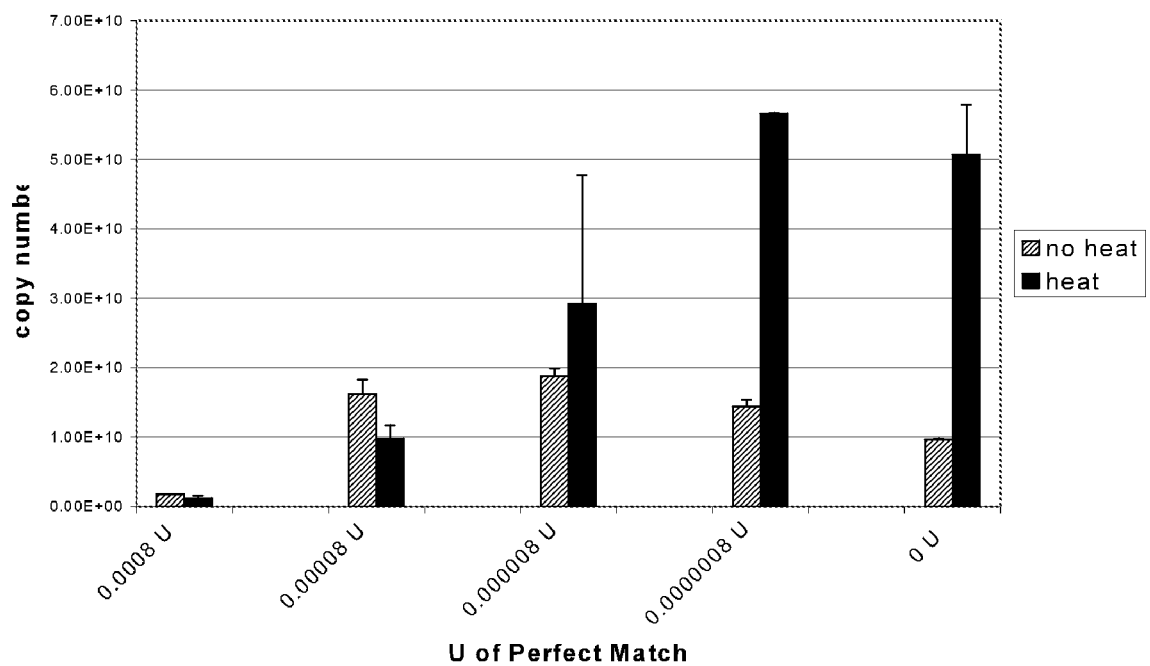
FIG. 2 depicts the effect of heating and addition of Perfect Match PCR Enhancer on reverse transcription efficiency.

QPCR was used to determine the effect of incubation at 55° C. (heat) or on ice (no heat) and the amount of Perfect Match on the RT efficiency (FIG. 2). As can be seen in FIG. 2, 0.0008 U Perfect Match appeared to have an inhibitory effect compared to lower amounts or no Perfect Match. $8\times10^{-6}$ U Perfect Match resulted in about 10-fold higher sensitivity than 0 U Perfect Match. However, the highest increase in sensitivity resulted from heating the samples prior to reverse transcription in the presence of 0 to $8\times10^{-7}$ U Perfect Match. Thus, a heating step at 50° C. was added to the incubation temperature profile when using AffinityScript in the RT reaction.

These results are used as a guideline in using Perfect Match in the reverse transcription reaction to increase assay sensitivity. Similar experiments are used in identifying reaction conditions to increase sensitivity of other enzymatic reactions.

In this experiment, the effect of Perfect Match on assay sensitivity was measured using a synthetic miRNA template. In practice, a miRNA in a mixture of different RNA, for example those present in total RNA, is quantitated. An experiment in which a miRNA template of known copy number is added to a total RNA sample lacking such miRNA template is useful in identifying reaction conditions in which Perfect Match and/or heating affects the assay sensitivity resulting in more accurate miRNA quantitation.

Example 8

QPCR Analysis of cDNA

For QPCR analysis, 0-5 microliters (uL) of the diluted RT products was added to each QPCR. In general the RT products were diluted 1:300 prior to use in QPCR. QPCR was performed using components from the Brilliant® SYBR® Green QPCR Core Reagent Kit (Stratagene) and Perfect Match® PCR Enhancer (optional; Stratagene). The reaction conditions were as follows (25 uL reaction volume): 1× Core PCR buffer, 2.5-5.5 mM magnesium chloride ($MgCl_2$), 200 micromolar (uM) each dNTP (dGTP, dATP, dTTP, and dCTP), 125-250 nanomolar (nM) miRNA-specific PCR primer (Table 5; SEQ ID NOs: 66-182), 125-250 nM R primer (Table 3; SEQ ID NOs: 58-61), $0\text{-}10^{-8}$ U Perfect Match, 30 nM ROX (reference dye, Stratagene), 1× EvaGreen™ (detection dye, Biotium) or 1×SYBR Green® I stock solution (detection dye, Invitrogen), and 1.25-2.5 U SureStart® Taq DNA polymerase. The cycling conditions were step 1: 1 cycle of 95° C. for 10 min (hot start) and step 2: 40 cycles of 95° C. for 10 seconds (sec); 55-60° C. for 15 sec; 72° C. for 20 sec (amplification). A dissociation curve was generated by: step 1: one cycle of 95° C. for 60 sec and ramp down to 55° C. for 30 sec and step 2: ramp up 55° C. to 95° C. (at a rate of 0.2° C./sec). The Mx3000P™ real-time PCR system (Stratagene) was used for thermal cycling and to quantitate the fluorescence intensities during QPCR and while generating the dissociation curve. If desired, further validation of the QPCR products can be performed by gel analysis of the QPCR products as described above.

As previous discussed, the choice of R primer used depends upon the RT adapter that was used to generate the cDNA. A R primer that is capable of annealing to the RT adapter and being extended by a polymerase is used.

Nucleic acids not containing a gene of interest are optionally added to test samples to reduce non-specific binding and to aid in recovery of small amounts of nucleic acids. These nucleic acids include yeast or *E. coli* tRNA, yeast or *E. coli* total RNA, and sheared, denatured salmon sperm DNA. For example, *Turulla* yeast total RNA (Ambion) or *Saccharomyces cerevisiae* yeast tRNA (Ambion). Such nucleic acids are considered to be inert as they do not affect the reaction into which they were placed. Alternatively, glycogen (Ambion) or linear acrylamide may be used. Any substance that does not contain a detectable gene of interest is suitable for this purpose. When cDNA generated from synthetic miRNA was analyzed, 0.1-10 ng sheared, denatured salmon sperm DNA (Stratagene) may be added to each QPCR to simulate reaction conditions when total RNA is used as the starting template.

Example 9

QPCR Specificity Testing Using Human Genomic DNA Template

PCR primers for use in the Examples were empirically tested to determine if they generated a detectable signal during QPCR in the presence of human genomic DNA and in the absence a sequence generated from a miRNA. No PCR product was detected in QPCR with several selected miRNA-specific primers and the R primer (SEQ ID NO:61) in the presence of 10 ng human genomic DNA. Thus, the signal indicating the presence of a miRNA generated during QPCR is unlikely to be due to the presence of contaminating genomic DNA in a sample.

Example 10

Polyadenylation control RNA templates were used as positive and negative controls in PAP reactions. A single-stranded RNA representing a previously-identified miRNA (Griffiths-Jones, S., R. J. Grocock, S. van Dongen, A. Bateman, A. J. Enright. 2006. miRBase: microRNA sequences, targets and gene nomenclature. Nucleic Acids Res., 34:D140-D144 and Griffiths-Jones, S. 2004. The microRNA Registry. Nucleic Acids Res. 32:D109-D111) or a miRNA not having significant homology to any previously-described miRNA (Alien; Table 2; SEQ ID NO:52) were used to test various polyadenylation conditions, to determine assay sensitivities, and to quantitate relative detection percentages in specificity assays. Nucleotide sequences of the mature miRNA were obtained from the most recent release of database provided at http: (doubleslash)microrna(dot)sanger(dot)ac(dot)uk(slash)sequences(slash). The naming convention in the database (Ambros, V., B. Bartel, D. P. Bartel, C. B. Burge, J. C. Carrington, X. Chen, G. Dreyfuss, S. R. Eddy, S. Griffiths-Jones, M. Marshall, M. Matzke, G. Ruvkun, T. Tuschl. 2003. A uniform system for microRNA annotation. RNA, 2003, 9(3):277-279) is used herein.

Polyadenylation Control RNA Templates

The polyadenylation control RNA templates may have a 5' OH or a 5' phosphate. The RNA control templates described herein have 5' OH. However, unpaired terminal nucleotides and 5' monophosphorylation have been shown to increase 3' polyadenylation by *Escherichia coli* poly(A) polymerase I in vivo (Feng, F., S. N. Cohen 2000. Unpaired terminal nucleotides and 5' monophosphorylation govern 3' polyadenylation by *Escherichia coli* poly(A) polymerase I. PNAS 97:6415-6420). Thus, the addition of a 5' monophosphate to the 5' end of a synthetic miRNA template may more accurately reflect the in vivo conditions and result in higher PAP reaction efficiencies when using *E. coli* PAP (E-PAP).

When RNA or DNA molecules corresponding to naturally-occurring miRNA are used as controls, there is the potential for contamination of test samples with control RNA or DNA resulting in false positives. Additionally, the detection of an Alien RNA or DNA molecule in test samples is an indication that contamination has occurred. Alternatively, known copy numbers of Alien RNA or DNA molecules are added to test samples to determine assay sensitivity, identify samples, and determine assay specificity.

Example 11

Reverse Transcriptase (RT) Control RNA Templates

RT control RNA templates were used as positive and negative controls in reverse transcription reactions. A single-stranded RNA representing a previously-identified miRNA or an Alien miRNA with a polyA tail consisting of 14 A (Table 4; SEQ ID NO:65) was used to test various RT conditions, to determine assay sensitivities, and to determine assay specificity.

The use of the RT control RNA template facilitated monitoring of the polyadenylation, reverse transcription, and amplification reactions. For example, a separate RT reaction with the RT control RNA template was used as a positive control and cDNA synthesized from the RT control RNA template was detected by generating a signal in QPCR. If the reaction including the RT control RNA template did not generate a signal in QPCR, it was an indication that either the RT reaction or the QPCR had failed. In contrast, if the reaction including the RT control RNA generated a signal in QPCR, it was an indication that both the RT reaction and QPCR had performed as expected. Additionally, if test samples in which a miRNA was present failed to generated a signal in QPCR while a signal was generated with the RT control RNA template, it was an indication that the polyadenylation reaction and not the reverse transcription reaction or QPCR had failed. Alternatively, a separate RT reaction with the RT control RNA template was used as a negative control by omitting one or more of the RT reaction components from the RT reaction and detected a signal generated in QPCR. If a signal was generated in QPCR, it could be used to identify sources of cross contamination or be used as a background signal. Thus, the RT control RNA template was useful in monitoring reactions described herein

Example 12

QPCR Control DNA Templates

QPCR control DNA templates were used as positive and negative controls in QPCR and to determine relative miRNA copy number. The QPCR control DNA template comprised a single-stranded DNA with the same sequence as a previously-identified miRNA or an Alien miRNA with 14 A and the nucleotide sequence corresponding to the RT adapter (Table 3). In addition, the QPCR control DNA template had 0-3 G added to the 5' end of the miRNA. Alternatively, a DNA sequence that was complementary to the above described QPCR control DNA template was used.

Potential contamination of QPCR with QPCR control DNA templates can be eliminated by replacing one or more T in the QPCR control DNA template with U and the addition of 0.5 units (U) uracil-N-glycosylase (UNG; Invitrogen) to the QPCR reaction. Such reactions are heated at 50° C. for 2 minutes prior to the first cycle of QPCR. Thus, a QPCR control DNA template with one or more U is also useful in this invention.

Example 13 miRNA Sources

RNA templates from cells included those in total RNA isolated from cell culture and fresh frozen tissues (Ambion and Stratagene). Additionally, total RNA isolated from Formalin-Fixed Paraffin-Embedded (FFPE) tissues using the Optimum™ FFPE RNA Isolation Kit (Assuragen) or RecoverAll™ Total Nucleic Acid Isolation Kit for FFPE (Ambion).

Synthetic RNA templates representing miRNA (Table 2) were synthesized by commercial vendors including TriLink Biotechnologies, Integrated DNA Technologies (IDT), and Operon using the standard oligonucleotide phosphoramidite synthetic chemistry (McBride, L. J. and M. H. Caruthers. 1983. An investigation of several deoxynucleoside phosphoramidites useful for synthesizing deoxyoligonucleotides. Tetrahedron Lett. 24:245-248) and purified by high performance liquid chromatography (HPLC) or isolated from polyacrylamide gels following separation by electrophoresis (PAGE).

Example 14

Synthetic DNA Oligonucleotides

Synthetic DNA oligonucleotides used as primers, annealed to RNA to detect polyadenylation products, and as QPCR DNA control templates were obtained from and synthesized as described for the synthetic RNA templates herein.

The nomenclature for the miRNA-specific primers is as follows. The name included the miRNA that was detected. F indicates it is a forward primer and separates the miRNA name from the description. G, 2G, or 3G indicates that one, two, or three G were added to the 5' end of the miRNA-specific primer and were not a part of the original miRNA nucleotide sequence. Primers wherein an A, T, or C was added to the 5' end use the same nomenclature. −X indicates the number of nucleotides that were removed from the 3' end of the miRNA sequence wherein X is a number. wt (wild type) indicates that the primer is the same nucleotide sequence as the miRNA with deoxyribonucleotides instead of ribonucleotides. Also, the omission of an indicator at the end of a primer name indicates wild type. +X indicates the number of nucleotides that were added to the 3' end of the miRNA sequence. In this case, X was an A that is complementary to the RT adapter nucleotide sequence.

TABLE 2

Nucleotide Sequences of miRNA Polyadenylation Controls

| SEQ ID NO | Name | RNA Nucleotide Sequence (5' to 3') |
|---|---|---|
| 1 | let-7a | UGAGGUAGUAGGUUGUAUAGUU |
| 2 | let-7b | UGAGGUAGUAGGUUGUGUGGUU |
| 3 | let-7c | UGAGGUAGUAGGUUGUAUGGUU |
| 4 | let-7d | AGAGGUAGUAGGUUGCAUAGU |
| 5 | let-7e | UGAGGUAGGAGGUUGUAUAGU |
| 6 | let-7f | UGAGGUAGUAGAUUGUAUAGUU |
| 7 | let-7g | UGAGGUAGUAGUUUGUACAGU |
| 8 | let-7i | UGAGGUAGUAGUUUGUGCUGU |
| 9 | miR-15a | UAGCAGCACAUAAUGGUUUGUG |
| 10 | miR-15b | UAGCAGCACAUCAUGGUUUACA |
| 11 | miR-16 | UAGCAGCACGUAAAUAUUGGCG |
| 12 | miR-17-3p | ACUGCAGUGAAGGCACUUGU |

TABLE 2-continued

Nucleotide Sequences of miRNA Polyadenylation Controls

| SEQ ID NO | Name | RNA Nucleotide Sequence (5' to 3') |
|---|---|---|
| 13 | miR-17-5p | CAAAGUGCUUACAGUGCAGGUAGU |
| 14 | miR-19a | UGUGCAAAUCUAUGCAAAACUGA |
| 15 | miR-20 | AAAAGUGCUUACAGUGCAGGUAGC |
| 16 | miR-21 | UAGCUUAUCAGACUGAUGUUGA |
| 17 | miR-23a | AUCACAUUGCCAGGGAUUUCC |
| 18 | miR-23b | AUCACAUUGCCAGGGAUUACC |
| 19 | miR-24 | UGGCUCAGUUCAGCAGGAACAG |
| 20 | miR-25 | CAUUGCACUUGUCUCGGUCUGA |
| 21 | miR-29a | UAGCACCAUCUGAAAUCGGUU |
| 22 | miR-29b | UAGCACCAUUUGAAAUCAGUGUU |
| 23 | miR-29c | UAGCACCAUUUGAAAUCGGU |
| 24 | miR-30c | UGUAAACAUCCUACACUCUCAGC |
| 25 | miR-32 | UAUUGCACAUUACUAAGUUGC |
| 26 | miR-92 | UAUUGCACUUGUCCCGGCCUG |
| 27 | miR-98 | UGAGGUAGUAAGUUGUAUUGUU |
| 28 | miR-106a | AAAAGUGCUUACAGUGCAGGUAGC |
| 29 | miR-107 | AGCAGCAUUGUACAGGGCUAUCA |
| 30 | miR-122a | UGGAGUGUGACAAUGGUGUUUGU |
| 31 | miR-126 | UCGUACCGUGAGUAAUAAUGC |
| 32 | miR-128b | UCACAGUGAACCGGUCUCUUUC |
| 33 | miR-140 | AGUGGUUUUACCCUAUGGUAG |
| 34 | miR-143 | UGAGAUGAAGCACUGUAGCUCA |
| 35 | miR-145 | GUCCAGUUUUCCCAGGAAUCCCUU |
| 36 | miR-146a | UGAGAACUGAAUUCCAUGGGUU |
| 37 | miR-146b | UGAGAACUGAAUUCCAUAGGCU |
| 38 | miR-155 | UUAAUGCUAAUCGUGAUAGGGG |
| 39 | miR-181a* | ACCAUCGACCGUUGAUUGUACC |
| 40 | miR-181b | ACAUUCAUUGCUGUCGGUGGG |
| 41 | miR-188 | CAUCCCUUGCAUGGUGGAGGGU |
| 42 | miR-191 | CAACGGAAUCCCAAAAGCAGCU |
| 43 | miR-199a | CCCAGUGUUCAGACUACCUGUUC |
| 44 | miR-200b | UAAUACUGCCUGGUAAUGAUGAC |
| 45 | miR-210 | CUGUGCGUGUGACAGCGGCUGA |
| 46 | miR-214 | ACAGCAGGCACAGACAGGCAG |
| 47 | miR-218-2 | UUGUGCUUGAUCUAACCAUGU |
| 48 | miR-219 | UGAUUGUCCAAACGCAAUUCU |
| 49 | miR-221 | AGCUACAUUGUCUGCUGGGUUUC |
| 50 | miR-223 | UGUCAGUUUGUCAAAUACCCC |
| 51 | miR-331 | GCCCCUGGGCCUAUCCUAGAA |
| 52 | Alien | UCGAUCACACAAUCAGUAGCA |

TABLE 3

Nucleotide Sequences of RT Adapters and Corresponding QPCR Primers

| SEQ ID NO | Name | DNA Nucleotide Sequence (5' to 3') |
|---|---|---|
| 53 | Chiang RT adapter | GCGAGCACAGAATTAATACGACTCACTATAGG TTTTTTTTTTTTTVN (V = G, A, or C; N = G, A, T, or C) |
| 54 | 60C RT adapter | CGACCTTGCGAGCACAGAATTAATACGACTCA CTATAGGTTTTTTTTTTTTVN (V = G, A, or C; N = G, A, T, or C) |
| 55 | RT adapter | GACAGCTCATGACGCACAGACACGACTAGAGT TCTTTTTTTTTTTTVN (V = G, A, or C; N = G, A, T, or C) |
| 56 | RT adapter | GACGAGCTGCCTCAGTCGCATAGCTTGATCGA TTTTTTTTTTTVN (V = G, A, or C; N = G, A, T, or C) |
| 57 | RT adapter without anchor | GACGAGCTGCCTCAGTCGCATAGCTTGATCGA TTTTTTTTTTTT |
| 58 | Chiang R QPCR primer | GCGAGCACAGAATTAATACGAC |
| 59 | 60C R QPCR primer | CGACCTTGCGAGCACAGAATTAATACGAC |
| 60 | F QPCR primer | GACGTCTCATGAGGTAGTAGGTTGCATAGTT |
| 61 | R QPCR primer | GACGAGCTGCCTCAGTCGCATAG |

TABLE 4

Nucleotide Sequences of RT Control RNA Templates

| SEQ ID NO | Name | RNA Nucleotide Sequence (5' to 3')62 |
|---|---|---|
| 62 | let-7a 14A | UGAGGUAGUAGGUUGUAUAGUUAAAAAAAAAAAAA63 |
| 63 | let-7c 14A | UGAGGUAGUAGGUUGUAUGGUUAAAAAAAAAAAAA64 |
| 64 | let-7d 14A | AGAGGUAGUAGGUUGCAUAGUAAAAAAAAAAAAAA65 |
| 65 | Alien 14A | UCGAUCACACAAUCAGUAGCAAAAAAAAAAAAAAA |

TABLE 5

Nucleotide Sequences of miRNA-Specific QPCR Primers

| SEQ ID NO | Primer | miRNA | DNA Nucleotide Sequence (5' to 3') |
|---|---|---|---|
| 66 | let-7aFwt | let-7a | GGTGAGGTAGTAGGTTGTATAGTT |
| 67 | let-7aF3Gwt | let-7a | GGGTGAGGTAGTAGGTTGTATAGTT |
| 68 | let-7aF3G-3 | let-7a | GGGTGAGGTAGTAGGTTGTATA |
| 69 | let-7aF-3 | let-7a | TGAGGTAGTAGGTTGTATA |
| 70 | let-7aF2Gwt | let-7a | GGTGAGGTAGTAGGTTGTATAGTT |
| 71 | let-7aF3G-3 | let-7a | GGGTGAGGTAGTAGGTTGTATA |
| 72 | let-7aF3G-3 | let-7a | GGGTGAGGTAGTAGGTTGTATA |
| 181 | let-7aF3Awt | let-7a | AAATGAGGTAGTAGGTTGTATAGTT |
| 182 | let-7aF3Twt | let-7a | TTTTGAGGTAGTAGGTTGTATAGTT |
| 183 | let-7aF3Cwt | let-7a | CCCTGAGGTAGTAGGTTGTATAGTT |
| 73 | let-7bFwt | let-7b | TGAGGTAGTAGGTTGTGTGGTT |
| 74 | let-7bF3G-5 | let-7b | GGGTGAGGTAGTAGGTTGTG |
| 75 | let-7bF3G-3 | let-7b | GGGTGAGGTAGTAGGTTGTGTG |
| 76 | let-7cFwt | let-7c | TGAGGTAGTAGGTTGTATGGTT |
| 77 | let-7cFGwt | let-7c | GTGAGGTAGTAGGTTGTATGGTT |
| 78 | let-7cF-3 | let-7c | TGAGGTAGTAGGTTGTATG |
| 79 | let-7cF3G | let-7c | GGGTGAGGTAGTAGGTTGTATGGTT |
| 80 | let-7cF3G-3 | let-7c | GGGTGAGGTAGTAGGTTGTATG |
| 81 | let-7cFG-3 | let-7c | GTGAGGTAGTAGGTTGTATG |
| 82 | let-7cF2G-3 | let-7c | GGTGAGGTAGTAGGTTGTATG |
| 83 | let-7cFG-5 | let-7c | GTGAGGTAGTAGGTTGTA |
| 84 | let-7cF2G-5 | let-7c | GGTGAGGTAGTAGGTTGTA |
| 85 | let-7dFwt | let-7d | AGAGGTAGTAGGTTGCATAGT |
| 86 | let-7dF3G | let-7d | GGGAGAGGTAGTAGGTTGCATAGT |
| 87 | let-7dF3A | let-7d | AAAAGAGGTAGTAGGTTGCATAGT |
| 88 | let-7dF3T | let-7d | TTTAGAGGTAGTAGGTTGCATAGT |
| 89 | let-7dF3C | let-7d | CCCAGAGGTAGTAGGTTGCATAGT |
| 90 | let-7dF3G-3 | let-7d | GGGAGAGGTAGTAGGTTGCAT |

TABLE 5-continued

Nucleotide Sequences of miRNA-Specific QPCR Primers

| SEQ ID NO | Primer | miRNA | DNA Nucleotide Sequence (5' to 3') |
|---|---|---|---|
| 91 | let-7dF3A-3 | let-7d | AAAAGAGGTAGTAGGTTGCAT |
| 92 | let-7dF3T-3 | let-7d | TTTAGAGGTAGTAGGTTGCAT |
| 93 | let-7dF3C-3 | let-7d | CCCAGAGGTAGTAGGTTGCAT |
| 94 | let-7dF3Gwt | let-7d | GGGAGAGGTAGTAGGTTGCATAGT |
| 95 | let-7dF3G-2 | let-7d | GGGAGAGGTAGTAGGTTGCATA |
| 96 | let-7dF-2 | let-7d | AGAGGTAGTAGGTTGCATA |
| 97 | let-7dF3G-5 | let-7d | GGGAGAGGTAGTAGGTTGC |
| 98 | let-7dF-5 | let-7d | AGAGGTAGTAGGTTGC |
| 99 | let-7eF1Gwt | let-7e | GTGAGGTAGGAGGTTGTATAGT |
| 100 | let-7eF3G-12 | let-7e | GGGTGAGGTAGG |
| 101 | let-7eF3G-2 | let-7e | GGGTGAGGTAGGAGGTTGTATA |
| 102 | let-7eFwt | let-7eF | TGAGGTAGGAGGTTGTATAGT |
| 103 | let-7fFwt | let-7f | GTGCTGAGGTAGTAGATTGTATAGTT |
| 104 | let-7fF3G-10 | let-7f | GGGTGAGGTAGTAGA |
| 105 | let-7fF3G-3 | let-7f | GGGTGAGGTAGTAGATTGTATA |
| 106 | let-7fFwt | let-7fF | TGAGGTAGTAGATTGTATAGTT |
| 107 | let-7gF2G | let-7g | GGTGAGGTAGTAGTTTGTACAGT |
| 108 | let-7gFwt | let-7g | TGAGGTAGTAGTTTGTACAGT |
| 109 | let-7gF2G-6 | let-7g | GGGGTAGTAGTTTGTA |
| 110 | let-7gF2G-5 | let-7g | GGGGTAGTAGTTTGTAC |
| 111 | let-7gF2G-4 | let-7g | GGGGTAGTAGTTTGTACA |
| 112 | let-7iFwt | let-7i | TGAGGTAGTAGTTTGTGCTGT |
| 113 | let-7iF2G-6 | let-7i | GGGGTAGTAGTTTGTG |
| 114 | let-7iF2G-5 | let-7i | GGGGTAGTAGTTTGTGC |
| 115 | let-7iF2G-4 | let-7i | GGGGTAGTAGTTTGTGCT |
| 116 | miR-15aFwt | miR-15a | TAGCAGCACATAATGGTTTGTG |
| 117 | miR-15aF3G-10 | miR-15a | GGGTAGCAGCACATAA |
| 118 | miR-15bFwt | miR-15b | TAGCAGCACATCATGGTTTACA |
| 119 | miR-16F2A | miR-16 | TAGCAGCACGTAAATATTGGCGAA |
| 120 | miR-16Fwt | miR-16 | TAGCAGCACGTAAATATTGGCG |
| 121 | miR-17-3pF2G-5 | miR-17-3p | GGACTGCAGTGAAGGCA |
| 122 | miR-17-3pF2G-4 | miR-17-3p | GGACTGCAGTGAAGGCAC |
| 123 | miR-17-5pFwt | miR-17-5p | CAAAGTGCTTACAGTGCAGGTAGT |
| 124 | miR-19aF2Gwt | miR-19a | GGTGTGCAAATCTATGCAAAACTGA |
| 125 | miR-19aF3G-7 | miR-19a | GGGTGTGCAAATCTATGCAA |
| 126 | miR-19aF3G-9 | miR-19a | GGGTGTGCAAATCTATGC |
| 127 | miR-20aF1G-4 | miR-20a | GTAAAGTGCTTATAGTGCAGG |

TABLE 5-continued

Nucleotide Sequences of miRNA-Specific QPCR Primers

| SEQ ID NO | Primer | miRNA | DNA Nucleotide Sequence (5' to 3') |
|---|---|---|---|
| 128 | miR-20aF3G-4 | miR-20a | GGGTAAAGTGCTTATAGTGCAGG |
| 129 | miR-21F3Gwt | miR-21 | GGGTAGCTTATCAGACTGATGTTGA |
| 130 | miR-21F2G-2 | miR-21 | GGTAGCTTATCAGACTGATGTT |
| 131 | miR-21F3G-2 | miR-21 | GGGTAGCTTATCAGACTGATGTT |
| 132 | miR-21F3Gwt | miR-21 | GGGTAGCTTATCAGACTGATGTTGA |
| 133 | miR-23aF3G-2 | miR-23a | GGGATCACATTGCCAGGGATTT |
| 134 | miR-23aF3G-1 | miR-23a | GGGATCACATTGCCAGGGATTTC |
| 135 | miR-23bF3G-1 | miR-23b | GGGATCACATTGCCAGGGATTAC |
| 136 | miR-23bF3G-2 | miR-23b | GGGATCACATTGCCAGGGATTA |
| 137 | miR-23bF3Gwt | miR-23b | GGGATCACATTGCCAGGGATTACC |
| 138 | miR-25Fwt | miR-25 | CATTGCACTTGTCTCGGTCTGA |
| 139 | miR-29aF3G-3 | miR-29a | GGGTAGCACCATCTGAAATCG |
| 140 | miR-29b-2F3G-5 | miR-29b | GGGTAGCACCATTTGAAATCA |
| 141 | miR-29b-2Fwt | miR-29b | TAGCACCATTTGAAATCAGTGTT |
| 142 | miR-29b-2F3G-5 | miR-29b | GGGTAGCACCATTTGAAATCA |
| 143 | miR-29cF3G-3 | miR-29c | GGGTAGCACCATTTGAAATCG |
| 144 | miR-30cF2G-1 | miR-30c | GGTGTAAACATCCTACACTCTCAG |
| 145 | miR-30cF3G-3 | miR-30c | GGGTGTAAACATCCTACACTCTC |
| 146 | miR-32F3Gwt | miR-32 | GGGTATTGCACATTACTAAGTTGC |
| 147 | miR-32F3G-6 | miR-32 | GGGTATTGCACATTACTA |
| 148 | miR-92-1Fwt | miR-92-1 | TATTGCACTTGTCCCGGCCTG |
| 149 | miR-98Fwt | miR-98 | GTGTGAGGTAGTAAGTTGTATTGTT |
| 150 | miR-98F3G-11 | miR-98 | GGGTGAGGTAGTAA |
| 151 | miR-98F3G-3 | miR-98 | GGGTGAGGTAGTAAGTTGTATT |
| 152 | miR-98Fwt | miR-98F | TGAGGTAGTAAGTTGTATTGTT |
| 153 | miR-106aFwt | miR-106a | AAAGTGCTTACAGTGCAGGTAGC |
| 154 | miR-106aF+2 | miR-106a | AGTGCTTACAGTGCAGGTAGC |
| 155 | miR-107F1G-1 | miR-107 | GAGCAGCATTGTACAGGGCTATC |
| 156 | miR-122aF3G-3 | miR-122a | GGGTGGAGTGTGACAATGGTGTT |
| 157 | miR-126F3G-2 | miR-126 | GGGTCGTACCGTGAGTAATAATG |
| 158 | miR-128bFGwt | miR-128b | GTCACAGTGAACCGGTCTCTTTC |
| 159 | miR-128bF3G-10 | miR-128b | GGGTCACAGTGAACC |
| 160 | miR-140F3Gwt | miR-140 | GGGAGTGGTTTTACCCTATGGTAG |
| 161 | miR-143F3Gwt | miR-143 | GGGTGAGATGAAGCACTGTAGCTCA |
| 162 | miR-145F2G-4 | miR-145 | GGGTCCAGTTTTCCCAGGAATC |
| 163 | miR-146aF3G-1 | miR-146a | GGGTGAGAACTGAATTCCATGGGT |
| 164 | miR-146aF3G-4 | miR-146a | GGGTGAGAACTGAATTCCATG |

TABLE 5-continued

Nucleotide Sequences of miRNA-Specific QPCR Primers

| SEQ ID NO | Primer | miRNA | DNA Nucleotide Sequence (5' to 3') |
|---|---|---|---|
| 165 | miR-146bF3G-1 | miR-146b | GGGTGAGAACTGAATTCCATAGGC |
| 166 | miR-146bF3G-4 | miR-146b | GGGTGAGAACTGAATTCCATA |
| 167 | miR-155F3G-1 | miR-155 | GGGTTAATGCTAATCGTGATAGGG |
| 168 | miR-155F3G-7 | miR-155 | GGGTTAATGCTAATCGTG |
| 169 | miR-155F3G-8 | miR-155 | GGGTTAATGCTAATCGT |
| 170 | miR-188F3G-7 | miR-188 | GGGCATCCCTTGCATGGT |
| 171 | miR-199aFwt | miR-199a | CCCAGTGTTCAGACTACCTGTTC |
| 172 | miR-199aF-1 | miR-199a | CCCAGTGTTCAGACTACCTGTT |
| 173 | miR-199aF-1-1 | miR-199a | CCAGTGTTCAGACTACCTGTT |
| 174 | miR-199aF2G | miR-199a | GGCCCAGTGTTCAGACTACCTGTTC |
| 175 | miR-200bF3G | miR-200b | GGGTAATACTGCCTGGTAATGATGAC |
| 176 | miR-219F3Gwt | miR-219 | GGGTGATTGTCCAAACGCAATTCT |
| 177 | miR-331FG2 | miR-331 | GGACCCTGAGCCTATCCTAGAA |
| 178 | AlienF3Gwt | Alien | GGGTCGATCACACAATCAGTAGCA |

TABLE 6

Nucleotide Sequences of QPCR DNA Templates

| SEQ ID NO | Name | DNA Nucleotide Sequence (5' to 3') |
|---|---|---|
| 179 | let-7d QPCR control DNA template | GGGAGAGGTAGTAGGTTGCATAGTAAAAAAAAAAAT CGATCAAGCTATGCGACTGAGGCAGCTCGTC |
| 180 | Alien QPCR control template | GGGTCGATCACACAATCAGTAGCAAAAAAAAAAAAT CGATCAAGCTATGCGACTGAGGCAGCTCGTC |

Example 15

Increasing Effectiveness of RT Reaction by Using Different RT Adapters and QPCR Primers For increasing the effectiveness of the conversion of polyadenylated RNA to cDNA, RT reactions were performed with four different RT adapters and their corresponding QPCR primers (Table 3; SEQ ID NOs: 53-61). Each RT adapter primer comprises an anchored oligo dT sequence and nucleotide sequences which act as primer binding sites in the subsequent QPCR. Thus, each RT adapter has a corresponding QPCR primer.

The teachings of Chiang, et al (Lu, S., Y. H. Sun, R. Shi, C. Clark, L. Li, V. L. Chiang. 2005. Novel and mechanical stress-responsive MicroRNAs in Populus trichocarpa that are absent from Arabidopsis. Plant Cell. 17(8):2186-203 and Shi, R., V. L. Chiang. 2005. Facile means for quantifying microRNA expression by real-time PCR. BioTechniques. 39(4):519-25) use a poly(T) adapter (Chiang RT adapter (Ambion); SEQ ID:53) and corresponding PCR primer (SEQ ID NO:58; Ambion). This adapter was first improved upon by the addition of nucleotides to increase the Tm of the QPCR primer in the 60 C RT adapter and QPCR primer (60 C; SEQ ID NOs:54 and 59, respectively). The unique nucleotides of the 60 C RT adapter were then replaced by two different unique nucleotide sequences in the F and R RT adapters (F; SEQ ID Nos:*55 and 56, respectively) and the corresponding F and R QPCR primers (R; SEQ ID NOs:60 and 61, respectively).

Figure 3:
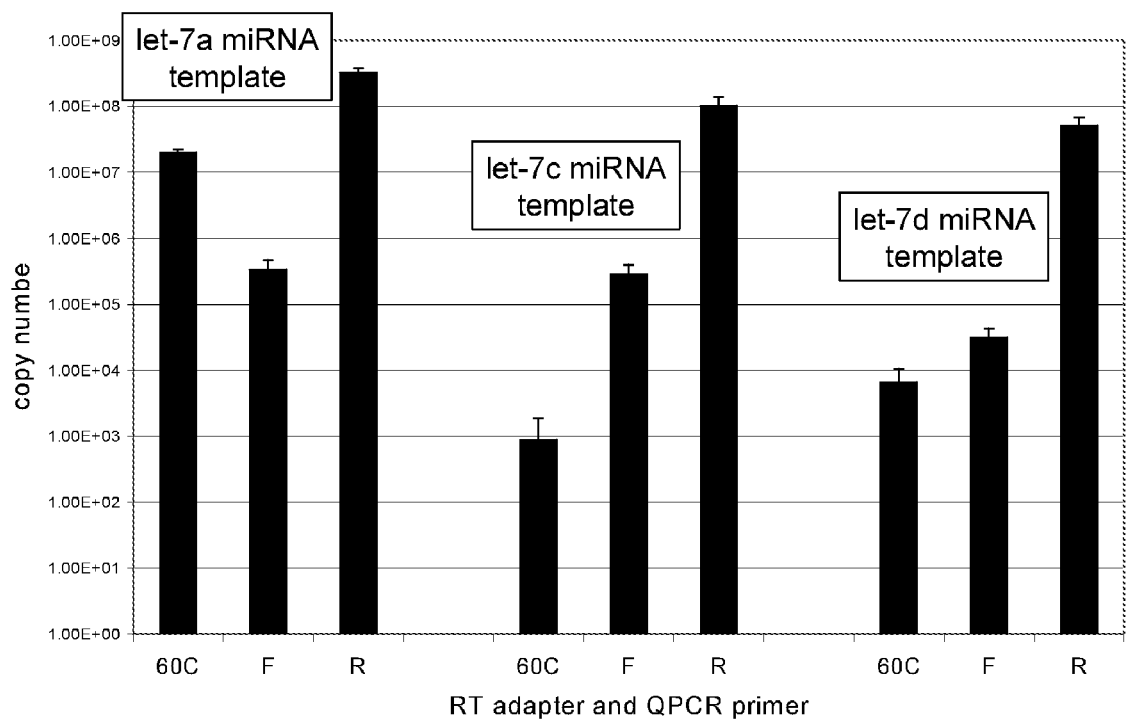
FIG. 3 depicts the effectiveness of the reverse transcription reaction using different reverse transcription adapters and QPCR primers.

As can be seen in FIG. 3, the assay sensitivity was increased by replacement of the 60 C RT adapter with the R RT adapter. These results were demonstrated using three different miRNA templates indicating that the increase in sensitivity when using the R RT adapter and R QPCR primer was not miRNA-specific. Thus, the use of the R RT adapter and the R QPCR primer represents an improvement over the initial poly(T) adapter (Chiang, V. L., et al). The F RT adapter was also more sensitive than the 60 C RT adapter with 2 of the 3 miRNA templates but was intermediate in sensitivity between the 60 C and R RT adapter and corresponding QPCR primer with one miRNA template.

Thus, the use of the R RT adapter and corresponding QPCR primer represent an improvement and were therefore used in subsequent experiment.

Example 16

Generation of Standard Curves in QPCR

A standard curve is useful in optimizing reaction conditions, testing the effect of RT reaction components on QPCR efficiency, determining the lower and upper detection limits, determining the QPCR efficiencies over ranges of template input, and in determining the copy number of miRNA in test samples. The copy number of miRNA in test samples was estimated by generating a standard curve of known copy number using the template and primers described herein in the same range as the copy number of miRNA in the test sample. The Ct of the miRNA test sample was compared to the standard curve to determine the relative copy number using the MX MxPro™ QPCR Software (Stratagene). While this method is not ideal as it does not include a correction for differences in amplification efficiencies between the test miRNA and the template used to generate the standard curve, it was useful in that it allowed for comparisons between experiments to be made. Thus, standard curves were generated for analysis of amplification of miRNA according to methods described herein.

In these examples, standard curves were generated with DNA templates having a miRNA-specific 5' primer binding region and 14 A with a universal 3' primer binding region. The universal 3' primer binding region allows for a common QPCR primer to be used with all of the templates amplified in these experiments. These templates were designed to simulate the template generated by polyadenylation and reverse transcription of miRNA, however, any other nucleotide sequence can be used.

In the examples given in Table 6 as suitable DNA templates, the 5' end corresponds to either the let-7d or Alien miRNA templates (SEQ ID NOs:4 and 52) and the 3' end corresponds to the R RT adapter (SEQ ID NO:56) and the corresponding R QPCR primer (SEQ ID NO:61). Thus, the let-7d and Alien miRNA-specific QPCR primers (SEQ ID NOs:97 and 178) are used in the QPCR to generate a standard curve.

Figure 4:
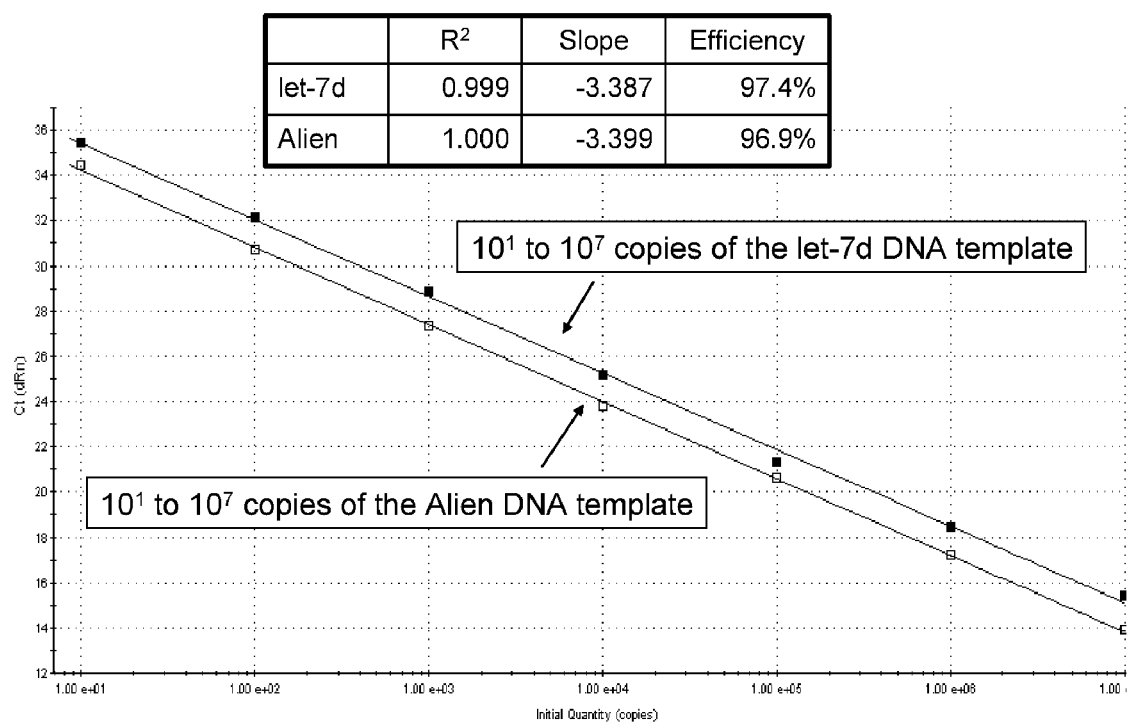
FIG. 4 depicts standard curves generated using let-7d and Alien templates.

For example, standard curves were generated using 10¹ to 10⁷ molecules of the let-7d (SEQ ID NO: 179) and Alien (SEQ ID NO: 180) DNA templates and their corresponding QPCR primers (SEQ ID NOs:97 and 178) with the R primer (SEQ ID NO:61) in QPCR (FIG. 4). As can be seen from the Figure, the standard curves are linear over 6 logs.

The linearity of the standard curve and the high correlation coefficient indicate the high degree of similarity between the QPCR efficiencies over a wide range of input DNA template. Similar standard curves were generated with both DNA templates indicating similar amplification efficiencies of the template representing the reverse transcribed polyadenylation products. Additionally, the presence of the homopolymeric region represented by the A:T-rich region does not appear to have an adverse effect on amplification efficiency.

Example 17

QPCR of miRNA cDNA with let-7 miRNA-specific QPCR Primers as Described by Chiang, V. L. et al.

The relative 3-step assay sensitivities were determined by polyadenylating all synthetic miRNA templates (Table 2; SEQ ID NOs: 1-8, 27), converting the polyadenylated miRNA templates to cDNA, and quantitating the cDNA by QPCR by using the corresponding miRNA-specific primers as described by Chiang, V. L., et al.

Figure 5:
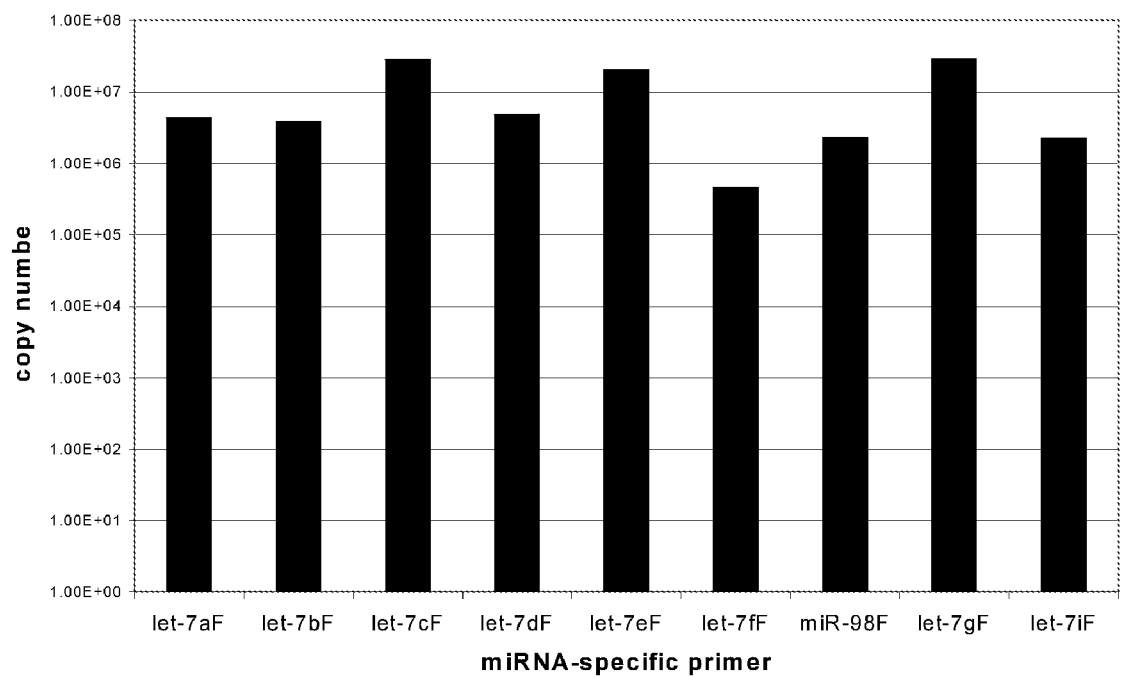
FIG. 5 depicts the relative assay sensitivities of different let-7 miRNA family members.

In FIG. 5, the relative 3-step assay sensitivities of the 9 different let-7 miRNA family members vary approximately 100-fold. This variation may be due to differences in the amount of synthetic miRNA template, differences in assay efficiency at one or more of the enzymatic steps, variations introduced during the purification step, and differences in QPCR efficiency. While these results demonstrate that the 3-step assay is capable of detecting miRNA templates, they do not indicate whether the miRNA-specific QPCR primers designed as described by Chiang, V. L., et al. can distinguish between the highly homologous let-7 miRNA templates.

Example 18

Determining Ability of let-7 Primers Designed According to Chiang, V. L., et al. to Distinguish Between let-7 miRNA Family Members The ability to distinguish between highly homologous let-7 family members was the primary goal of these experiments. As previously discussed, the let-7 family members have likely arisen from genomic duplication and mutation. Along with these changes, changes in expression of the various family members have also occurred. While the significance of these differences is currently being studied, it is likely that these differences will be critical to the understanding of their biological function.

To determine if the let-7aFwt and let-7dFwt primers designed according to Chiang, V. L., et al. could distinguish between the let-7a and let-7d miRNA templates, the let-7 synthetic miRNA templates were polyadenylated, converted to cDNA, and QPCR with let-7aFwt and let-7dFwt QPCR primers as described by Chiang, V. L., et al. In this experiment, the Chiang RT adapter primer and corresponding QPCR primer were used.

Figure 6:
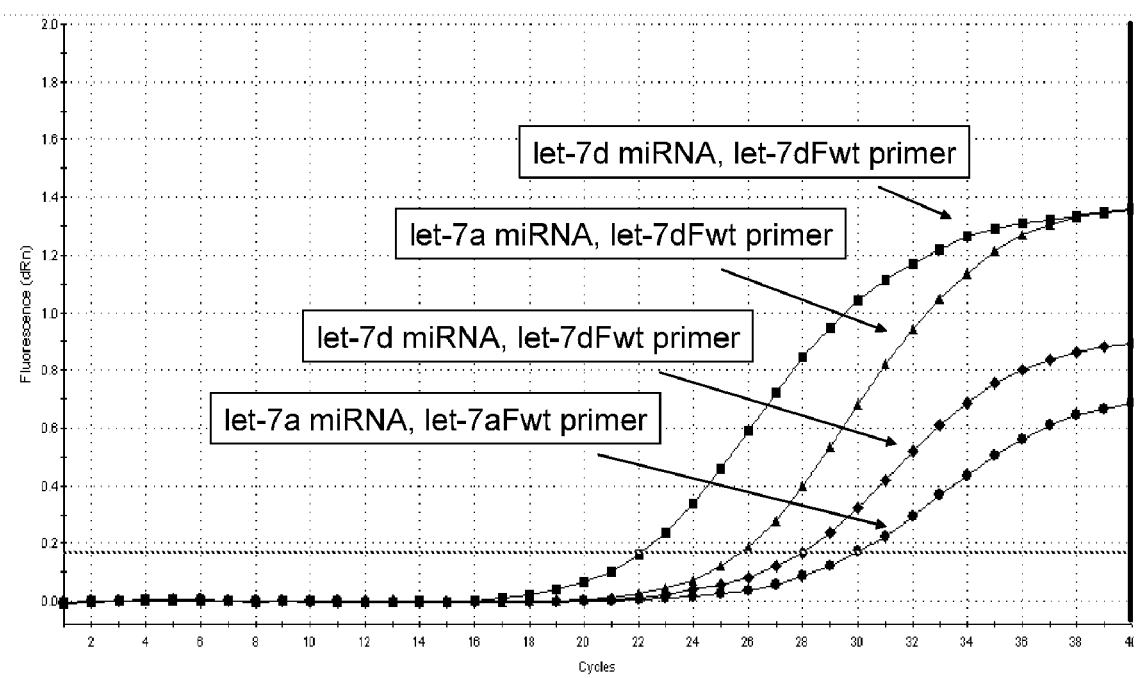
FIG. 6 depicts the detection of let-7a and let-7d miRNA templates.

As shown in FIG. 6, the let-7aFwt and let-7dFwt primers detected both the let-7a and let-7d miRNA templates. In fact, the lowest Cts (highest copy numbers) were the let-7dFwt primer with both the let-7a and let-7d miRNA templates. This might indicate that the let-7dFwt primer primes more efficiently than the let-7aFwt primer. In addition, fewer copies of the let-7a miRNA template are detected than the let-7d miRNA template when using the let-7aFwt primer. These results clearly indicate that neither the let-7aFwt or let-7dFwt primer detects only the corresponding let-7 miRNA template and therefore do not have the desired specificity.

While the method and primer design of Chiang, V. L., et al. was effective in detecting miRNA, it did not discriminate between the highly homologous let-7 family members at a level that would allow one to accurately quantitate the amount of a let-7 miRNA in a RNA sample derived from a cell. An improved primer design method was therefore investigated.

Example 19

Comparison of let-7a miRNA to Remaining let-7d Family Member Nucleotide Sequences A comparison of the let-7a miRNA and the other let-7 family members revealed between one and four nucleotide differences at different nucleotide positions throughout the length of the miRNA (FIG. 7). The nucleotide identities involved in the mismatches created between let-7a and the remaining let-7 family members vary. The single mismatch four nucleotides from the 3' end of let-7c indicates that the let-7a primer cannot be decreased in length from the 3' end more than four nucleotides. While the remaining nucleotide differences occur primarily in the middle or toward the 3' end of the miRNA, the best position to place the 3' end of the let-7a primer is not clear. The random position of these differences made it challenging to find a single base position where the nucleotide differences would have the highest effect on priming specificity while retaining assay sensitivity.

Example 20

Figure 8A:
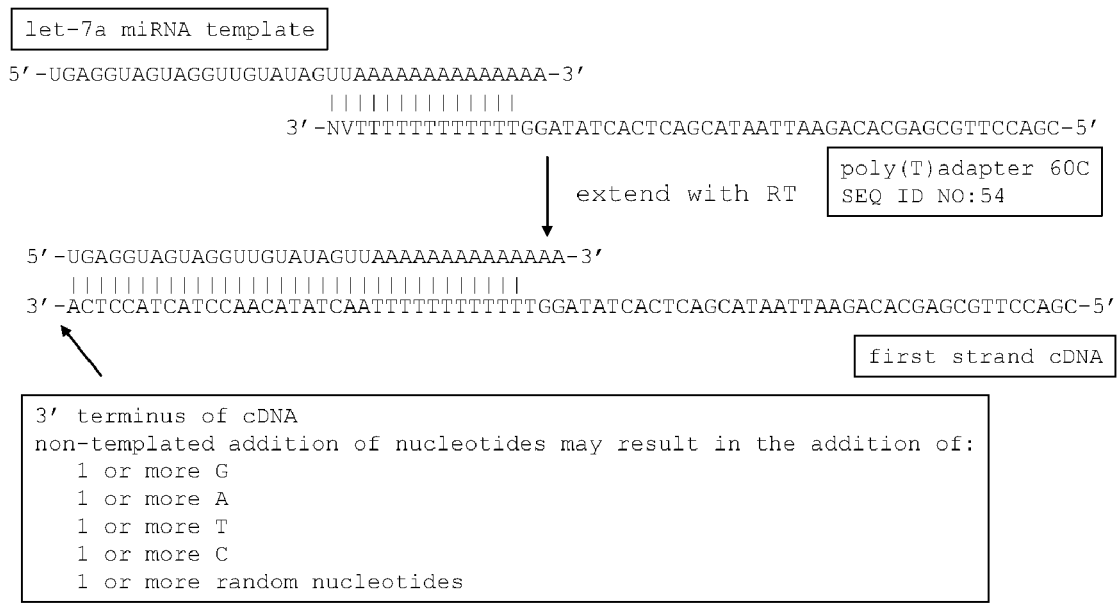

Relative Ability of let-7a miRNA-Specific QPCR Primers with Additional Nucleotides at the 5' end of the Primer and 3 Nucleotides Removed from the 3' End to Detect let-7a miRNA Template In Chenchik, A., Y. Zhu, L. Diatchenko, P. Siebert (U.S. Pat. No. 5,962,272), a method is described that is dependent upon the non-templated addition of nucleotides to the 3' end of a cDNA by a reverse transcriptase to allow for template switching. This template switching mechanism utilizes a 7-methylguanosine CAP structure present on the 5' ends of all eukaryotic mRNA. Additionally, template switching occurs primarily at the 5' end of a full-length mRNA and the non-templated addition is primarily C. The addition of one or more nucleotides to the 3' end of the miRNA cDNA in the reverse transcription method was desirable in that it would increase the length of the miRNA template (FIG. 8A-C). This method was combined with cDNA size fractionation to generate large full-length clones (Wellenreuther, R., I. Schupp, A. Poustka, S. Wiemann. 2004. SMART amplification combined with cDNA size fractionation in order to obtain large full-length clones. BMC Genomics. 5:36). In this method, it is noted that synthesis must be performed with a MMLV RTase that is RNaseH negative to ensure addition of C residues, and to prevent degradation of the template switch oligonucleotide during base pairing with these residues. Thus, it was uncertain whether a RNA template not having a 7-methylguanosine CAP structure and a MMLV having RNase H activity would be effective in non-templated nucleotide addition.

To this end, let-7a miRNA-specific QPCR primers were designed wherein 3 G, A, T, or C were added to the 5' end of the let-7a miRNA sequence (Table 5; SEQ ID Nos:67, 181, 182, 183). A second set of primers with the same addition to the 5' end and 3 nucleotides removed from the 3' end were also designed.

Figure 9:
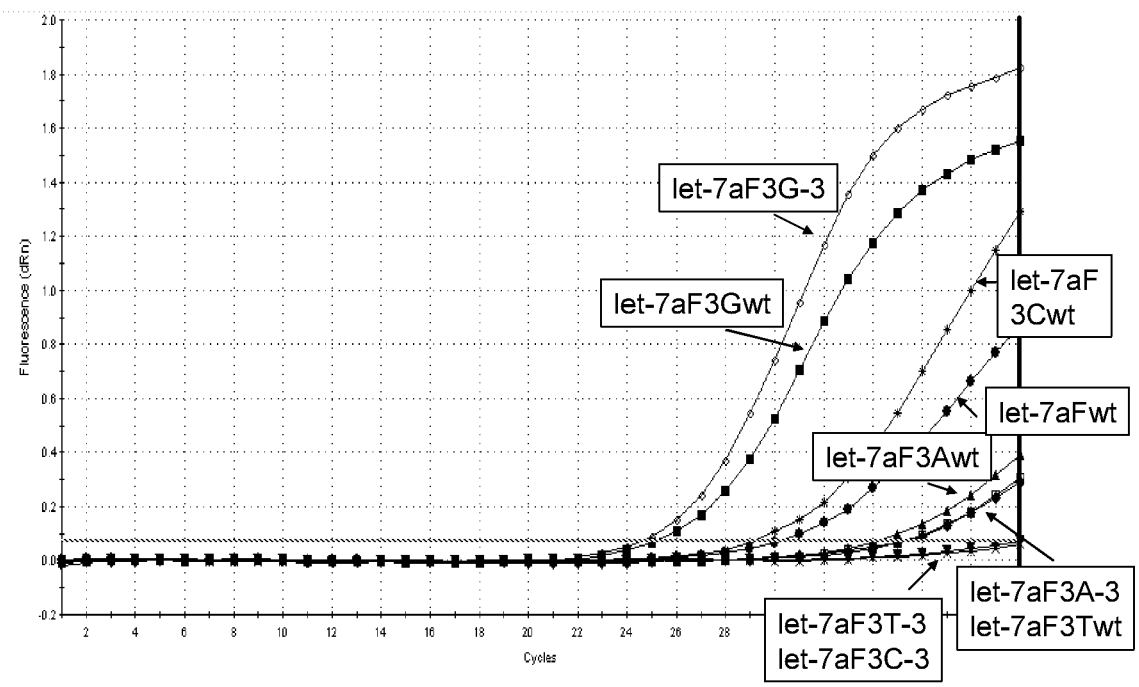
FIG. 9 depicts the assay sensitivity using different nucleotides on the 5' end of the let-7a primer.

The relative ability of the various let-7a miRNA-specific QPCR primers with G, A, T, or C added to the 5' end and either no nucleotides or 3 nucleotides removed from the 3' end was determined. As shown in FIG. 9, the addition of 3G at the 5' end of the let-7a primer (let-7aF3G-3 and let-7aF3Gwt) resulted in the highest assay sensitivity as demonstrated by the lowest Cts. let-7aF primers with either 3C (let-7aF3Cwt) or designed according to Chiang, V. L., et al. (let-7aFwt) were intermediate in sensitivity while the remaining primers tested had the lowest sensitivities. In addition, these results indicate that the removal of 3 nucleotides from the 3' end (let-7aF3G-3) did not change the sensitivity of the assay when compared to the full length primer (let-7aF3Gwt). These results clearly demonstrate the benefit that adding 3G to the 5' end of the let-7a miRNA-specific QPCR primer had on assay sensitivity. These results further indicate that non-templated addition of one or more C to the 3' end of the miRNA cDNA during reverse transcription has likely occurred.

The increase in assay sensitivity demonstrated with the addition of 3G to the 5' end of the let-7a miRNA-specific QPCR primer was observed with all four of the reverse transcriptases tested herein. The reverse transcriptases either have detectable RNase H activity or lack detectable RNase H activity indicating that this effect is independent of RNase H activity. This is in contrast to previous observations that indicated that non-templated nucleotide addition only occurred in the absence of RNase H activity (Wellenreuther, R., et al., above).

The addition of random nucleotides to the 5' end of a PCR primer to increase annealing between the primer and template following one round of polymerase extension is commonly used to increase PCR effectiveness. At first glance, it appeared that the addition of the 3G to the 5' end of the let-7aF miRNA-specific QPCR primer had this same affect. However, if this addition had simply improved annealing between the primer and template after the first primer extension reaction, one would expect to see the same effect with the primer wherein 3C were added to the 5' end of the let-7aF miRNA-specific QPCR primer as it would increase the Tm by the same amount. However, this is not the result. The Cts of both primers having 3G added to the 5' end were lower than the primer having 3C added to the 5' end. The let-7a miRNA-specific QPCR primers that generated high sensitivity were tested for specificity with all let-7 family members.

Due to the heterogeneity seen between let-7a miRNA and the other let-7 family members throughout the nucleotide sequence of the miRNA, a different member of the let-7 miRNA family with less heterogeneity or with heterogeneity at fewer nucleotide positions was sought. When the next series of primers for detection of this miRNA were designed, primers with removal of nucleotides from the 3' end with no addition of nucleotides to the 5' end were also tested.

Example 21

Comparison of let-7d miRNA to Remaining let-7d Family Member Nucleotide Sequences A comparison of the let-7d miRNA and the other let-7 family members revealed that the nucleotide at the position 6 bases from the 3' end of the let-7d miRNA was different than the nucleotide in all other let-7 family members (FIG. 10). In addition, the mismatch created at that position was a C in the let-7d primer sequence and an A in the other let-7 family member cDNA. This mismatch has been shown to be favorable in discrimination assays. It was therefore desirable to decrease the length of the let-7d primer to allow for the 3' end to be at or 3' of the C:A mismatch position. However, decreasing the length of the let-7d primer to these positions would decrease the Tm to a point where it was unlikely to anneal to the let-7d miRNA cDNA and be extended using traditional QPCR protocols. A method that would allow for removal of the 5 nucleotides at the 3' end of the let-7d primer that resulted in high sensitivity and specificity was therefore desirable.

To this end, let-7d miRNA-specific QPCR primers were designed wherein 3 G were added to the 5' end of the let-7d miRNA sequence and with either 0, 2, or 5 nucleotides were removed from the 3' end. As previously stated, primers without the addition of 3G and the removal nucleotides from the 3' end were also designed (Table 5; SEQ ID Nos: 86, 95, 97).

Example 22

Figure 11:
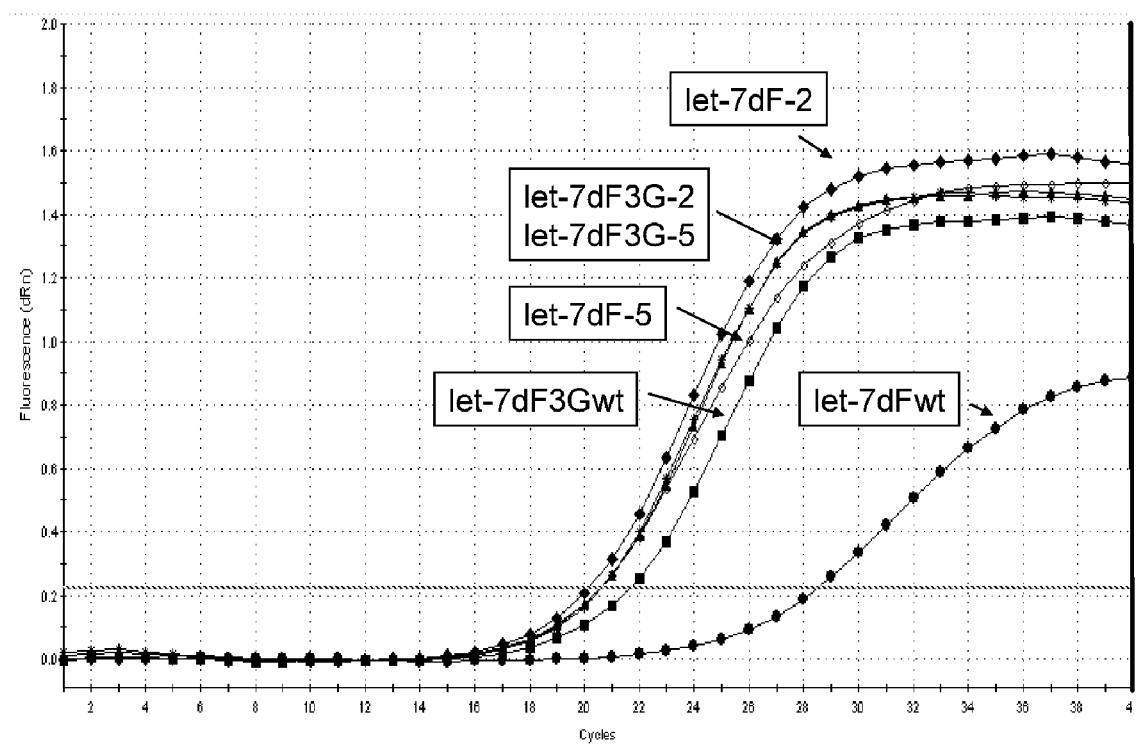
FIG. 11 depicts assay sensitivity using different let-7d primers with let-7d miRNA template.

Relative Ability of let-7d miRNA-Specific QPCR Primers with 3G at the 5' End of the Primer and Nucleotides Removed from the 3' end to Detect let-7d miRNA Template to Determine Assay Sensitivity The relative ability of the various let-7d miRNA-specific QPCR primers with 3G added to the 5' end and either 0, 2, or 5 nucleotides removed from the 3' end to detect the let-7d miRNA synthetic template was determined. As shown in FIG. 11, the addition of 3G at the 5' end of the let-7d primer (let-7dF3Gwt, let-7d3G-2, and let-7dF3G-5) resulted in high assay sensitivity as demonstrated by the lowest Cts. In addition, let-7d miRNA-specific QPCR primers without the addition of 3G (let-7dF-2 and let-7dF-5) showed high sensitivity. The let-7dFwt primers designed according to Chiang, V. L., et al. had the lowest sensitivity. It is interesting to note that in this assay, the removal of up to 5 nucleotides from the 3' end of the primer had little or no effect on the assay sensitivity.

In this example, the assay sensitivity in the detection of the let-7d miRNA template with various let-7d primers was determined. In the next example, the same let-7d primers were used to detect the let-7a miRNA template to determine assay specificity.

Example 23

Relative Ability of let-7d miRNA-Specific QPCR Primers to Detect let-7a miRNA Template to Determine Assay Specificity In the previous example, the assay sensitivity with various let-7d primers was determined. In this example, the same let-7d primers were used to detect the let-7a miRNA template to determine assay specificity.

Figure 12:
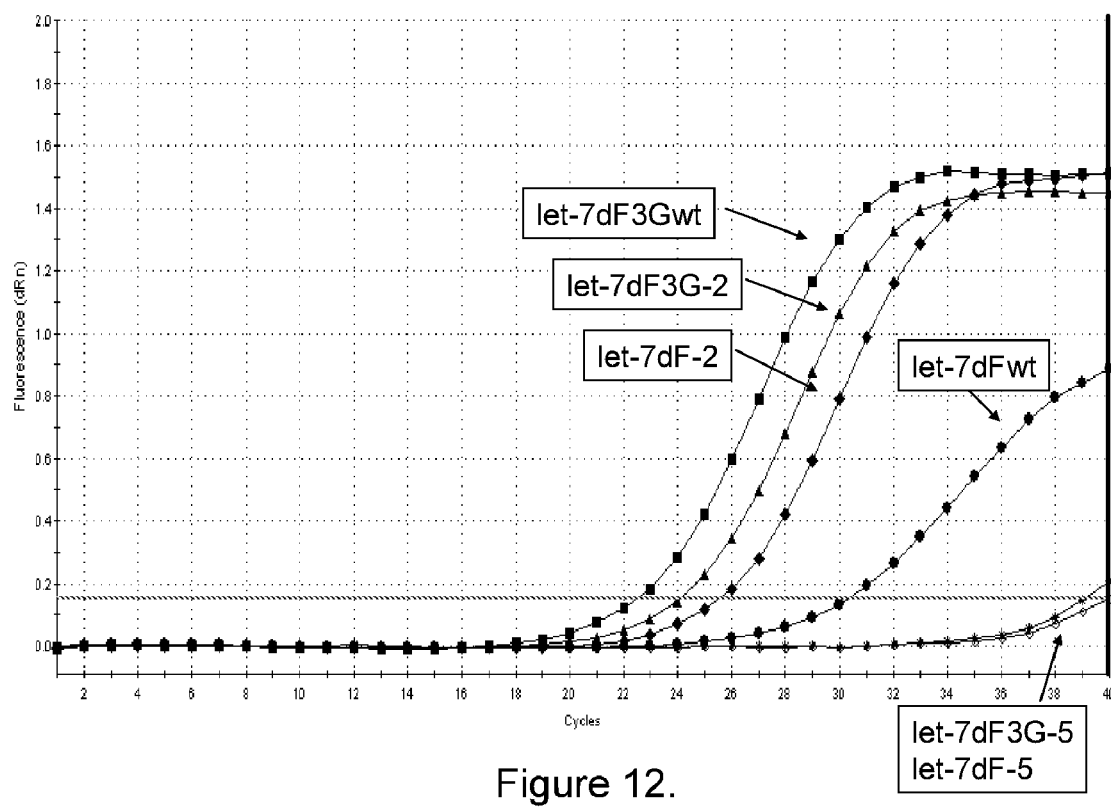
FIG. 12 depicts assay sensitivity using different let-7d primers with let-7a miRNA template.

The relative ability of the various let-7d miRNA-specific QPCR primers with 3G added to the 5' end and either 0, 2, or 5 nucleotides removed from the 3' end to detect the let-7a miRNA synthetic template was determined. As shown in FIG. 12, let-7d primers having either 0 or 2 nucleotides removed from the 3' end (let-7dF3Gwt, let-7d3G-2, and let-7dF-2) had the highest sensitivity which indicated the lowest specificity. The primer designed according to Chiang, V. L. et al (let-7dFwt) had intermediate specificity while both primers having 5 nucleotides removed from the 3' end (let-7dF-5 and let-7dF3G-5) had the highest specificity.

While these results indicate that the addition of 3G at the 5' end did not appear to improve assay specificity, their addition may still be of value in increasing the Tm of primers designed to detect other miRNA. To test this idea, a variety of miRNA-specific QPCR primers having 0 to 3G and varying numbers of nucleotides removed from the 3' end were evaluated for assay sensitivity.

Example 24

Relative 3-Step Assay Sensitivity Using Different miRNA Synthetic Templates and Corresponding miRNA-Specific Primers The relative 3-step assay sensitivities were determined by polyadenylating all synthetic miRNA templates (Table 2; SEQ ID NOs: 1-52), converting the polyadenylated miRNA templates to cDNA, and quantitating the cDNA by QPCR by using the corresponding miRNA-specific primers.

Figure 13:
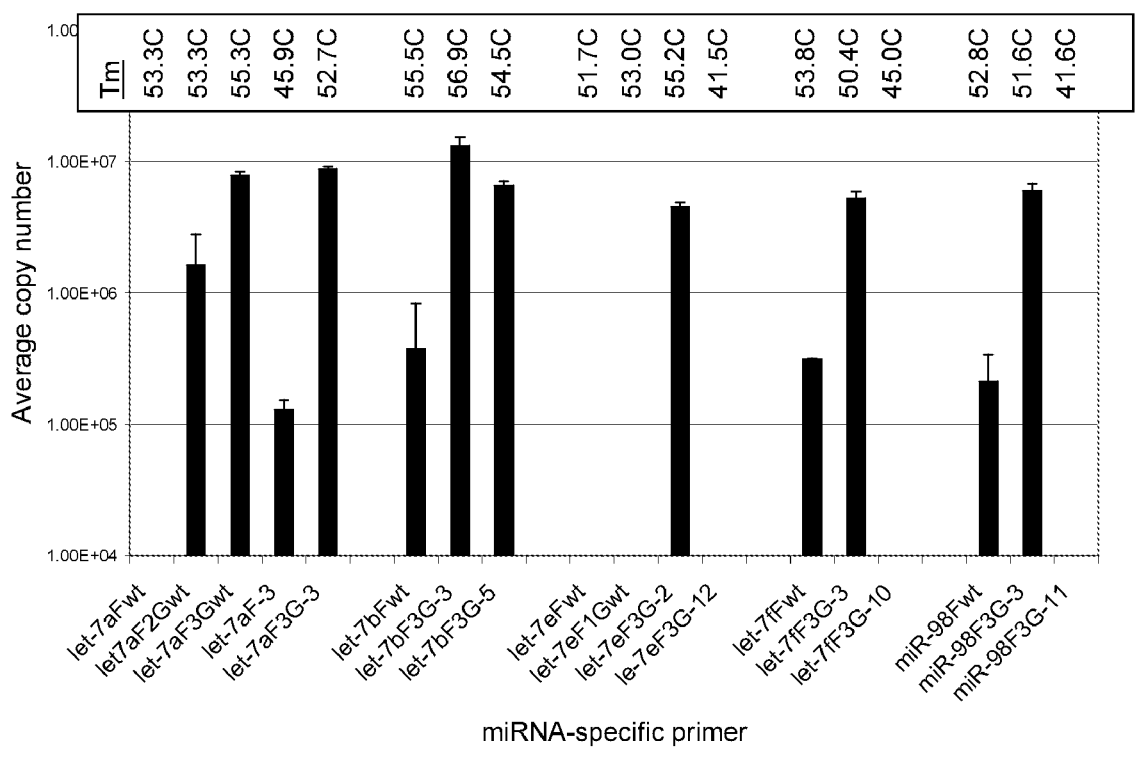
FIG. 13 depicts assay sensitivity using different miRNA synthetic templates.

In FIG. 13, the relative 3-step assay sensitivities of the 5 different miRNA are within 10-fold when using at least one of the miRNA-specific primers. In general, the assay sensitivities correlate with the Tm of the primer, however, that is not always the case. It is likely that the identity of the nucleotide(s) at the 3' end of the primer also affects the assay sensitivity. For example, a primer having a A or T at the 3' end is less likely to be extended in a polymerase reaction than a G or C.

The addition of one or more G to the 5' end appears to increase assay sensitivity as seen with let-7aF2Gwt ($1.61 \times 10^6$ copies) and let-7aF3Gwt ($7.85 \times 10^6$ copies) and let-7aF-3 ($1.29 \times 10^5$ copies) and let-7aF3G-3 ($8.77 \times 10^6$ copies). In this example, no copies were detected with the let-7aF primer. This may have been due to experimental error as this primer did detect copies in other experiments. This example also shows the increase in assay sensitivity when adding nucleotides to the 5' end while removing them from the 3' end of the let-7b primers. In this example, the let-7bFwt primer detected $3.74 \times 10^5$ copies, the let-7bF3G-3 primer detected $1.32 \times 10^7$ copies, and the let-7bF3G-5 primer detected $6.52 \times 10^6$ copies. Thus, the removal of up to 5 nucleotides from the 3' end of the let-7bFwt primer and addition of 3G to the 5' end resulted in an increase in assay sensitivity.

In another example, the sensitivity of miR-155 was ~100-fold lower than the other miRNA. The lower sensitivity of miR-155 with all 3 primers tested is likely due to the presence of 4 G at the 3' end of the miR-155 synthetic RNA template (SEQ ID NO:38) and its affect on the PAP reaction. More than 3 G in a single-stranded nucleic acid are known to have secondary structure. E-PAP is sensitive to secondary structure (Feng, Y., S. N. Cohen. 2000. Unpaired terminal nucleotides and 5' monophosphorylation govern 3' polyadenylation by *Escherichia coli* poly(A) polymerase I. Proc. Natl. Acad. Sci. 97:6415-6420) and the presence of secondary structure may be the reason. The miR-155 synthetic miRNA template may therefore be useful in identifying PAP reaction conditions which allow for more efficient polyadenylation of miRNA having secondary structure.

Example 25

Relative Assay Sensitivity Using Synthetic miRNA Templates

In this example, three of the let-7 family miRNA-specific QPCR primers having the highest sensitivities in the previous example (let-7aF3G-3, let-7c3G-3, and let-7d3G-5) were tested for specificity using cDNA generated from synthetic let-7 RNA family members. miR-98 was included in this testing as it is considered a member of the let-7 family based on its nucleotide sequence homology. The let-7d3G-5 primer was tested for specificity with the let-7a miRNA template in a previous example.

The relative percent detection of all miRNA synthetic templates with a single let-7 miRNA-specific primer were determined by polyadenylating miRNA corresponding to the 9 let-7 family members, converting the polyadenylated miRNA templates to cDNA, and quantitating the cDNA by QPCR using a let-7 family miRNA-specific primer.

In this example, the % relative detection was calculated by setting the copy number of the let-7 miRNA template and its corresponding primer as 100%. The copy number of the other miRNA templates with the primer being tested were compared to this copy number and the % relative detection was calculated (FIG. 14). For example, the copy number of the let-7d miRNA template detected with the let-7dF3G-5 miRNA-specific QPCR primer was set as 100%. The copy number of the remaining miRNA templates detected with the let-7dF3G-5 miRNA-specific QPCR primer were compared to the let-7d miRNA template copy number and the % relative detection was calculated. Thus, the % relative detection may be greater or lesser than 100%.

The copy numbers of the let-7 miRNA templates detected with the let-7aF3G-3 primer were converted to % relative detection (FIG. 14). Since the copy number detected of the let-7d miRNA template with the let-7aF3G-3 primer was ~2.5-fold higher than that detected of the let-7a miRNA template, it was calculated to be 254% relative detection. At first this is somewhat surprising, however, when one looks at the nucleotide sequence comparison between let-7a and let-7d miRNA (FIG. 7), one sees that there are only two nucleotide differences between these miRNA at nucleotide positions 1 and 16 from the 5' end of the let-7a miRNA template. In addition, the nucleotide difference that is closest to the 3' end and therefore would have the highest effect on primer binding and extension, is a T in the let-7aF3G-3 primer and a G in the let-7d miRNA template. As previously discussed, this mismatch is very difficult to discriminate against. In addition, this mismatch is 4 nucleotides from the 3' end of the let-7aF3G-3 primer and thus is less likely to have an effect on primer binding and extension than a mismatch that occurs closer or at the 3' end. Together with the % relative detections of the remaining let-7 family member miRNA, the nucleotide sequence comparison of the let-7d and let-7a miRNA and these results clearly illustrate the challenges in designing miRNA-specific QPCR primers and reaction conditions that can distinguish between these miRNA.

In early experiments, it was found that the let-7d miRNA-specific QPCR primer, let-7d3G-5 (SEQ ID NO:97), generated high sensitivity when detecting the let-7d miRNA template (FIG. 11) and specificity when detecting the let-7a miRNA template (FIG. 12). The results in FIG. 14 clearly indicate that the let-7d3G-5 primer also had high specificity with all let-7 miRNA templates as evidenced by the <0.24% relative detection. In contrast to the example given above for the let-7aF3G-3 primer, the nucleotide sequence comparison between let-7d and the remaining let-7 family member miRNA (FIG. 10), one sees that there is a single nucleotide difference between these miRNA at nucleotide position 6 from the 3' end of let-7d and the remaining let-7 miRNA templates. In addition, the nucleotide difference is a C in the let-7dF3G-5 primer and an A in the remaining let-7 miRNA templates. As previously discussed, this mismatch is one of the easiest to discriminate against. The removal of 5 nucleotides from the 3' end in the design of the let-7dF3G-5 primer places this mismatch in the most favorable position for discrimination, at the 3' end of the primer. Thus, this mismatch is most likely to affect primer binding and polymerase extension. This nucleotide sequence comparison and these results clearly illustrate the most favorable conditions for designing miRNA-specific QPCR primers that can distinguish between these miRNA.

Specificity with the let-7cF3G-3 primer when detecting the different let-7 miRNA templates was intermediate between the results of let-7aF3G-3 and let-7d3G-5 primers with highest % relative detections of 11.73 and 0.01 when detecting the let-7b and let-7l miRNA templates, respectively (FIG. 14).

Thus, while it was clear that a method that did not include either the addition or removal of nucleotides to the 5' or 3' ends of the primers would be needed to further increase specificity was needed, an experiment in which the ability to distinguish between let-7c and let-7d miRNA templates when combined was first conducted.

Example 26

Figure 15:
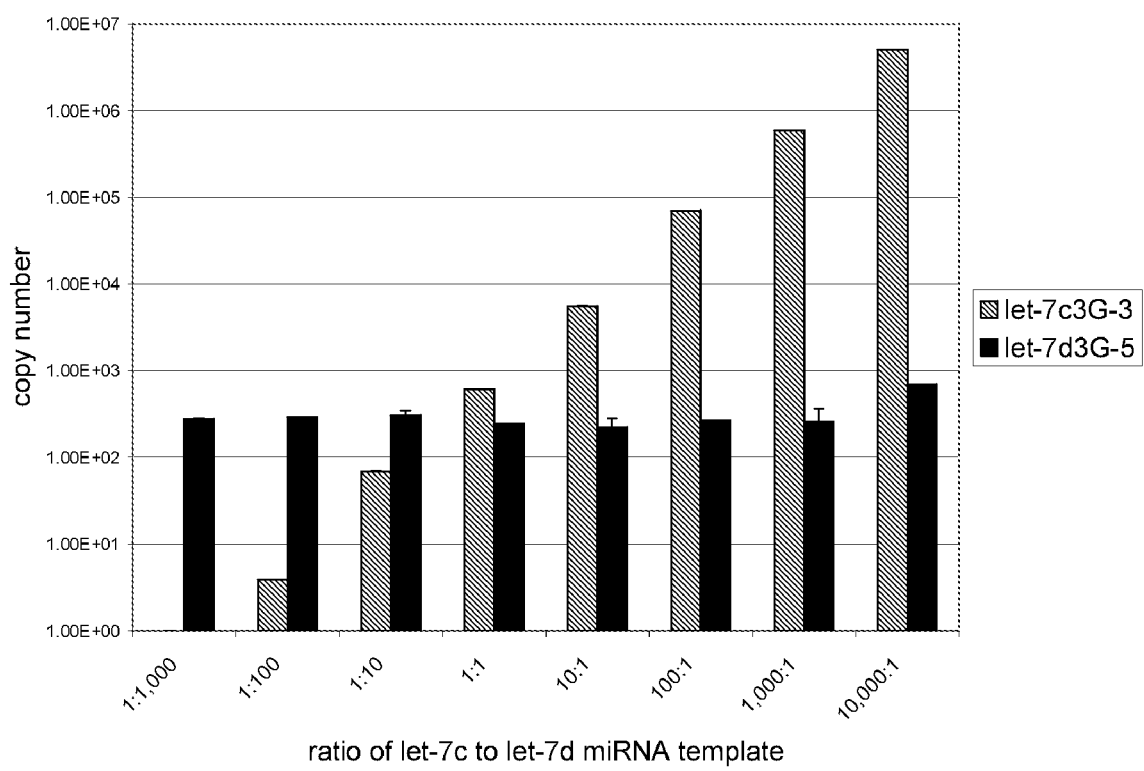
FIG. 15 depicts assay specificity determined by detecting varying numbers of let-7c miRNA.

Assay Specificity Determined by Detecting Varying Numbers of let-7c miRNA in a Constant Number of let-7d miRNA To demonstrate that the method of this invention can distinguish between closely related let-7 family members in the same reaction, varying numbers of let-7c miRNA in a constant number of let-7d miRNA were combined and quantitated. In this experiment, $10^6$ copies of let-7d miRNA (SEQ ID NO:4) were combined with 103 to 1010 copies of let-7c miRNA (SEQ ID NO:3). The combined miRNA resulted in ratios ranging from 1:1,000 to 10,000:1 copies of let-7c to let-7d miRNA, respectively. The combined miRNA were polyadenylated, reverse transcribed, and detected by QPCR using let-7cF3G-3 (SEQ ID NO: 80) or let-7dF3G-5 (SEQ ID NO: 97) miRNA-specific QPCR primers (FIG. 15).

The detection of a constant number of let-7d miRNA in all samples and increase in detection of let-7c indicates assay specificity. The slight increase in detection of let-7d in the sample with 10,000 copies of let-7c compared to 1 copy of let-7d may indicate a slight variability in the assay or a very small amount of detection of let-7d miRNA by the let-7c3G-3 primer. These results are consistent with <0.5% relative detection with these primers and templates in the results shown in FIG. 14.

While these results with the let-7cF3G-3 and let-7dF3G-5 primers indicate high assay specificity, it was unlikely that similar results would be obtained with the let-7aF3G-3 primer. In addition, although the let-7cF3G-3 primer had very low % relative detection with the let-7d miRNA template, it had almost 12% relative detection with the let-7b miRNA template. A method with increased specificity was therefore sought.

Example 27

Determining the Effect of Perfect Match on the Assay Specificity Determined by Detecting let-7 miRNA Templates with let-7c3FG-3 miRNA-specific QPCR Primer To determine if the presence of Perfect Match could increase assay specificity when using the let-7cF3G-5 miRNA-specific primer in discriminating between the closely related let-7 family members, each let-7 miRNA (SEQ ID NOs: 1-8, 27) were polyadenylated, converted to cDNA, and used as a template in two sets of QPCR with the let-7cF3G-3 miRNA-specific QPCR primer (SEQ ID NO:80). One set did not include Perfect Match and the second set included 0.00008 U of Perfect Match in each reaction. The copy number that corresponded to the let-7c miRNA template and let-7c3G-3 miRNA-specific primer was used as 100% relative detection. The copy number of the remaining let-7 family member miRNA templates was calculated relative to the copy number of the let-7c miRNA template and is expressed as % relative detection.

The detection of let-7 family members other than let-7c with the let-7c3G-3 miRNA-specific primer indicated the assay was unable to distinguish between all of the closely-related miRNA (FIG. 16). However, the addition of Perfect Match improved the ability to distinguish between the let-7a and let-7b miRNA templates. In particular, the % relative detection decreased from 7.3 to 0.3% with the let-7a miRNA template and from 13.5 to 1.5% with the let-7b miRNA template.

Figure 18:
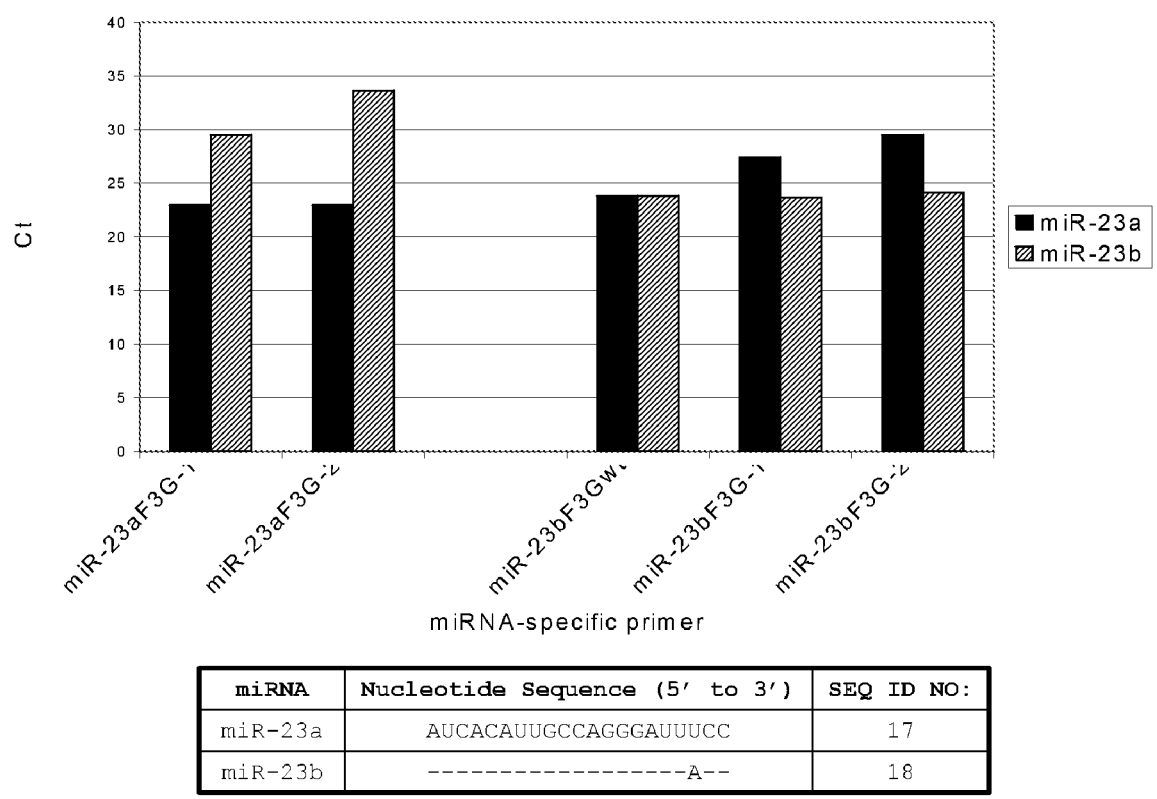
FIG. 18 depicts assay sensitivity using miR-23a and miR-23b templates in the presence of Perfect Match.

The identities of the nucleotides in the mismatches, the nucleotide positions of the mismatches, and the number of mismatches between the let-7cF3G-3 primer and the miRNA template are also given in FIG. 18. As previously discussed, G:T mismatches such as that present between the let-7a miRNA template and the let-7cF3G-3 miRNA-specific primer are particularly difficult to discriminate against. In this example, the addition of Perfect Match and termination of the let-7cF3G-3 miRNA-specific primer at this position decreased the % relative detection to 0.3%. The A:C mismatch present between the let-7b miRNA template and the let-7cF3G-3 miRNA-specific primer is generally a favorable mismatch, however, in this case it is not. The lower discrimination is likely to be because this mismatch is 3 nucleotides from the 3' end of the let-7cF3G-3 primer and therefore less likely to affect primer binding and polymerase extension. The reduction in % relative detection by the addition of Perfect Match increases the discrimination to an acceptable level. As expected, the higher the number of mismatches that are present between the primer and template, the higher the discrimination. In addition, those mismatches at the 3' end of the let-7cF3G-3 miRNA-specific primer have lower % relative detection than those at other positions.

While the addition of Perfect Match improved the results with a limited number of miRNA templates and the let-7cF3G-3 miRNA-specific primer, additional experiments with varying concentrations of Perfect Match and other templates were also tested.

Example 28

Assay Specificity with let-7 miRNAs and miRNA-specific QPCR Primers in the Presence of Perfect Match To demonstrate that the method of this invention can distinguish between closely related let-7 family members, each let-7 miRNA (SEQ ID NO: 1-8, 27) was converted to cDNA and used as a template in a QPCR with each of the let-7 miRNA-specific QPCR primers (SEQ ID NO: 68, 75, 80, 97, 101, 105, 111, 115, and 151) and with 0.0002 U Perfect Match in each QPCR. A standard curve generated with 101 to 107 copies of the Alien DNA template was used to estimate the copy number of each miRNA detected. The copy number that corresponded to the correctly paired miRNA and miRNA-specific QPCR primer was considered to be 100% detection. The copy number corresponding to the incorrectly paired miRNA and the miRNA-specific QPCR primer was calculated relative to the correctly paired miRNA and primer and is expressed as % relative detection.

Figure 17:
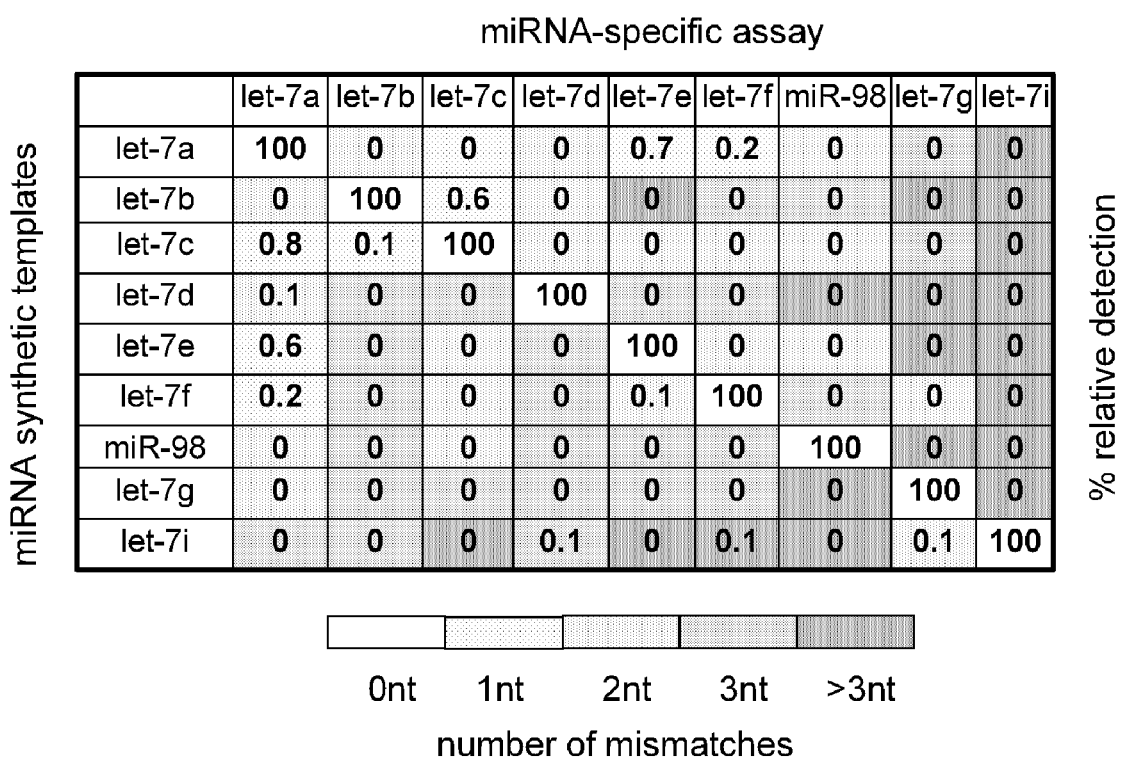
FIG. 17 depicts assay specificity of let-7 miRNAs and miRNA-specific QPCR in the presence of Perfect Match.

As can be seen in FIG. 17, the miRNA-specific assay indicates the miRNA-specific primer used in the assay with the miRNA synthetic template. The number of mismatches in the combination of miRNA-specific primer and miRNA synthetic template is indicated as shown below the table. It is can quickly be seen that increasing the number of mismatches between the miRNA-specific primer and miRNA template results in lower % relative detection. In contrast, decreasing the number of mismatches results in higher % relative detection.

In this experiment, all % relative detections were less than 1%. In order to determine how these results compare to existing technologies, they were compared to the TaqMan® MicroRNA Assays from Applied Biosystems and the miRCURY™ LNA Arrays from Exiqon. The % relative detection in this experiment are significantly less than the % relative detection reported for the TaqMan® MicroRNA Assays (Caifu, C., D. A. Ridzon, A. J. Broomer, Z. Zhou, D. H. Lee, J. T. Nguyen, M. Barbisin, N. L. Xu, V. R. Mahuvakar, M. R. Andersen, K. Q. Lao, K. J. Livak, K. J. Guegler. 2005. Real-time quantification of microRNAs by stem-loop RT-PCR. Nucleic Acids Res. 33(20): e179). In particular, 3.7 and 2.5% relative detection was observed with let-7a miRNA assay and the let-7e synthetic template and let-7c miRNA assay and the let-7b synthetic template, respectively. The % relative detection for this experiment is also significantly less than that demonstrated with the miRCURY™ LNA Arrays http:(double slash)www(dot)exiqon(dot)com(slash)SEEEMS(slash)26(dot)asp). In particular, up to 20 and 35% relative detection of let-7b and let-7e, respectively, with the let-7a capture probe was reported. Additionally, let-7a was detected at 7-18% relative detection with let-7b, let-7e, and let-7f capture probes. These comparisons clearly demonstrate that the method described herein has higher specificity than competing technologies.

Example 29

Assay Specificity with miR-23a and miR-23b miRNAs and miRNA-specific QPCR Primers in the Presence of Perfect Match The primer design described herein was used to design miR-23a and miR-23b miRNA-specific QPCR primers and the QPCR conditions described herein were used to distinguish between miR-23a and miR-23b miRNA templates. As shown in FIG. 18, there is a single nucleotide difference between miR-23a and miR-23b three nucleotides from the 3' end of the miRNA. This mismatch results in a T:T mismatch between the miR-23a miRNA-specific primer and the miR-23b miRNA template and an A:A mismatch between the miR-23b miRNA-specific primer and the miR-23a miRNA template.

In this example, 3G were added to the 5' end of all miRNA-specific primers tested. Additionally, in this example, 1 and 2 nucleotides were removed from the miR-23a miRNA-specific primers (SEQ ID NOs:133 and 134) and 0, 1, and 2 nucleotides were removed from the miR-23b miRNA-specific primers (SEQ ID NOs: 137, 135, and 136). Additional nucleotides could not be removed as the position 3 nucleotides from the 3' end of both miRNA is the only difference between the miRNA.

As can be seen in FIG. 18, little or no difference in sensitivity was detected with the miR-23a and miR-23b miRNA-specific primers with the miR-23a and miR-23b miRNA templates, respectively, as evidenced by similar Cts. In contrast, a significant difference (6.55 and 10.69 Ct) in sensitivity was detected with both miR-23a miRNA-specific primers and the miR-23b miRNA template indicating high assay specificity. Additionally, there was no difference (23.81 and 23.83 Ct) in sensitivity detected with the miR-23bF3Gwt miRNA-specific primer when detecting the miR-23a and miR-23b miRNA templates, respectively. Removal of 1-2 nucleotides from the 3' end of the miR-23b miRNA-specific primers increased the difference in Ct between the miR-23a and miR-23b miRNA templates to 3.8 and 5.4 Ct with the miR-23bF3G-1 and miR-23bF3G-2 miRNA-specific primers, respectively.

Thus, while the miR-23a primers have similar sensitivity when detecting the miR-23a miRNA template, miR-23aF3G-2 has high specificity as demonstrated by its detection of the miR-23b miRNA template. Therefore, the shorter miR-23a miRNA-specific primer (miR-23aF3G-2; SEQ ID NO:133) is the better primer as it has high sensitivity and is specific for miR-23a miRNA template.

Thus, while the longest miR-23b primer has similar sensitivity to the other miR-23b miRNA-specific primers when detecting the miR-23b miRNA template, it has the lowest specificity as demonstrated by its detection of the miR-23a miRNA template. Therefore, the shortest miR-23b miRNA-specific primer (miR-23bF3G-2; SEQ ID NO: 136) is the best primer as it has high sensitivity and is specific for miR-23b miRNA template.

The application of the primer design rules and reaction conditions identified using the let-7 family members to the use of the miR-23a and miR-23b miRNA-specific QPCR primers illustrates the utility of these rules in distinguishing between miRNA having a single nucleotide difference.

Example 30

Determining 3-step Assay Linearity and Sensitivity by Detection of miRNA of Varying Abundances in Total RNA To demonstrate the ability of the 3-step assay to detect miRNA of varying abundance in a total RNA sample, the relative amounts of miR-23a, let-7d, and miR-106 miRNA in cDNA prepared from varying amounts of human lung total RNA (Stratagene) were determined. In these assays, the amount of total RNA used as the starting template was varied in 2-fold dilutions from 0.9766 ng to 1.0 ug in separate PAP reactions. The total RNA was polyadenylated, purified, converted to cDNA, and the Ct of the three miRNA was determined using the miR-23aF3G-2 (SEQ ID NO:133), let-7dF3G-5 (SEQ ID NO:97), and miR-106aF+2 (SEQ ID NO: 154) miRNA-specific primers.

Figure 19:
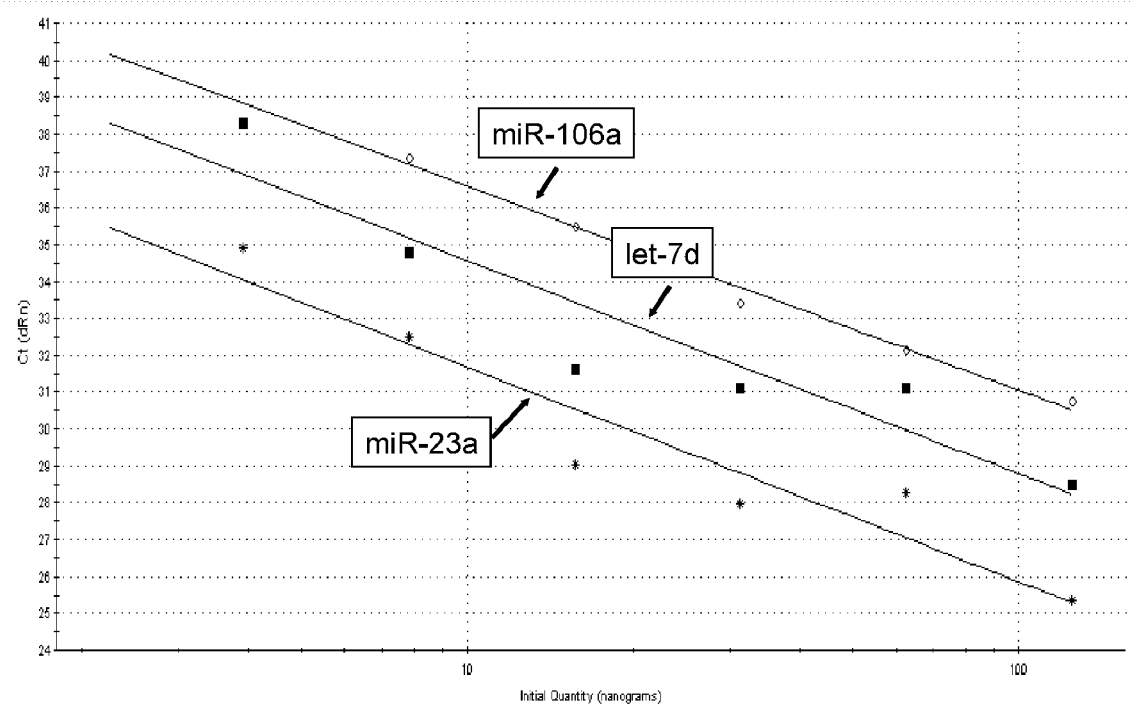
FIG. 19 depicts assay linearity and sensitivity by detection of miRNA of varying abundances in total RNA.

As shown in FIG. 19, each miRNA was present in the human lung total RNA at different abundances and the Ct of each miRNA across 15.7 to 250 ng of total RNA varies linearly. The variability seen in this assay is likely due to the purification step wherein the samples were phenol:chloforom extracted and precipitated as described herein between the polyadenylation and reverse transcription steps. There was little increase in assay sensitivity when more than 250 ng of total RNA was used as the starting template. Thus, the 3-step assay is sensitive to changes in template input and is fairly linear when the amount of total RNA template is between 15.7 and 250 ng.

Example 31

Determining Signal Linearity in QPCR by Detection of miRNA Using Varying Amounts of Starting cDNA Template In Example 30, the amount of total RNA input into the 3-step reaction was varied. In contrast, in this Example the amount of cDNA input into the QPCR was varied. The relative amounts of miR-23a, let-7d, and miR-106 miRNA in varying amounts of human lung cDNA (Stratagene) were determined. In these assays, 1 ug of human lung total RNA (Stratagene) was polyadenylated and converted to cDNA in a reverse transcription reaction. The amount of cDNA added to each QPCR varied in 2-fold dilutions and corresponded to 6.5 picograms (pg) to 3.3 ng of human lung total RNA.

Figure 20:
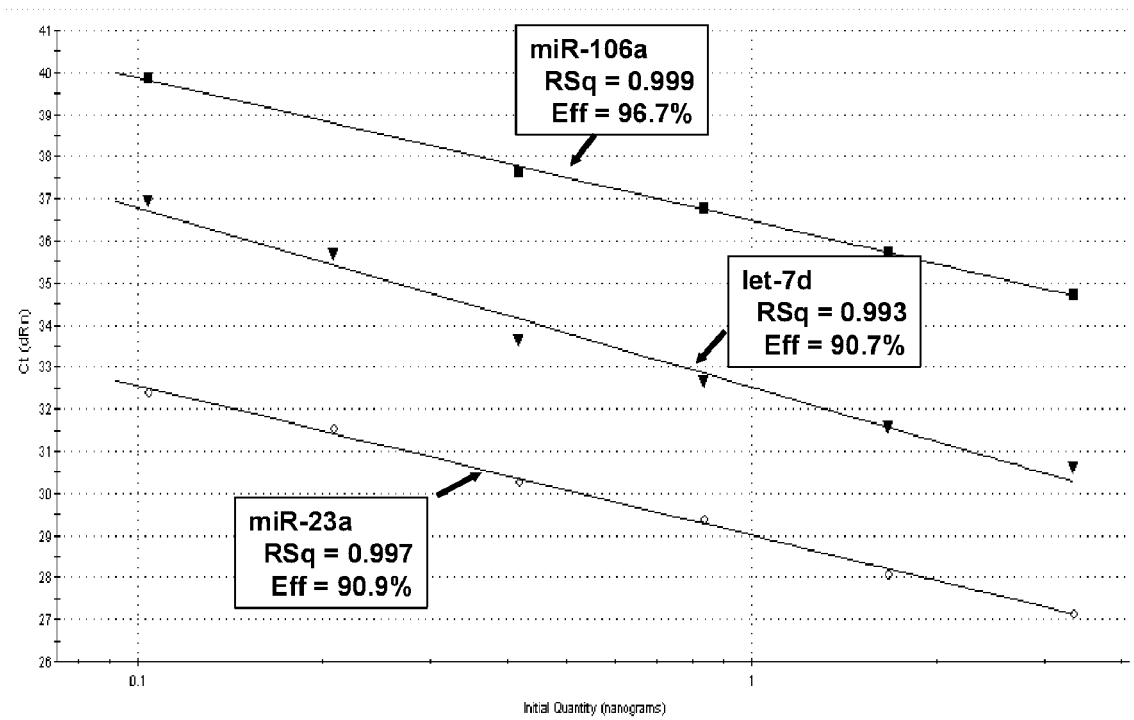
FIG. 20 depicts signal linearity of QPCR by detection of miRNA using varying amounts of starting cDNA template.

As shown in FIG. 20, each miRNA was present in the human lung total RNA at different abundances and there was high signal linearity as evidenced by the Pearsons correlation coefficients (RSq values) of 0.993 to 0.999 between 0.1 and 3.3 ng of input total RNA. In addition, the amplification efficiencies of miR-23a and let-7d were similar (90-91%). The amplification efficiency of miR-106a was slightly higher (96.7%). These results indicate that differences in the amounts of the miRNA were detected over a broad range of template input. Thus, the 3-step assay was sensitive to changes in template input and was linear when the amount of cDNA template corresponded to 0.1 to 3.3 ng of input total RNA.

The amount of RT reaction product added to the QPCR may be adjusted by using more and less product to detect miRNA of lower and higher abundance, respectively. Additionally, less RT reaction product may be added to the QPCR if assay inhibition due to the RT reaction components on the QPCR is suspected.

Example 32

Primer Design Resulting in High Assay Sensitivity and Specificity

The examples herein describe a method of primer design resulting in high assay sensitivity and specificity. The steps for designing a primer for a pre-selected miRNA are as follows: 1) obtain nucleotide sequence of mature miRNA, 2) align nucleotide sequences by homology, 3) identify miRNA having homology to the 3' end of the pre-selected miRNA, 4) identify the position of the mismatch or mismatches between the pre-selected miRNA and other miRNA having high homology to the pre-selected miRNA, 5) identify the nucleotides in the mismatch or mismatches between the pre-selected miRNA and other miRNA having high homology to the pre-selected miRNA, 6) determine if the primer would benefit by removing nucleotides from the 3' end to position the 3' end of the primer close to one or more mismatches, 7) place the 3' end at a position which avoids having a T:T or G:T mismatch at the 3' end of the primer, 8) estimate the Tm of the full-length and shortened primers, 9) add one or more G to the 5' end of the primer to increase the Tm of the primer to >48 C, 10) test the primers for assay sensitivity in the 3-step assay with pre-selected miRNA synthetic template, and 11) test primers having high assay sensitivity with miRNA synthetic templates having high homology to determine assay specificity. Use those miRNA-specific QPCR primers having the highest assay sensitivity and specificity to detect miRNA in total RNA samples.

In order for primer extension to occur, the primer must anneal to the template and be extended by a polymerase. While the method above is focused on the effect of the nucleotides at the 3' end of the primer when designing a miRNA-specific QPCR primer of high sensitivity and specificity, it should be noted that as few as a single mismatch up to 11 nucleotides from the 3' end of the primer may be sufficient to prevent or significantly reduce primer binding and extension. An example of this is shown in the specificity demonstrated between the let-7aF3G-3 miRNA-specific primer and the let-7e miRNA template. In FIG. 7, the sequence comparison of let-7a and let-7e miRNA shows a single nucleotide difference 9 nucleotides from the 5' end of both miRNA and 14 nucleotides from the 3' end of the let-7a miRNA template. Three bases were removed from the let-7a miRNA template in the design of the let-7aF3G-3 miRNA-specific primer. Thus, the position of the single nucleotide mismatch between the let-7aF3G-3 miRNA-specific primer and the let-7e miRNA template is 11 nucleotides from the 3' end of the let-7e miRNA template. As shown in FIG. 14, the relative detection of the let-7e miRNA template was ~50% in the initial experiments. In contrast, the % relative detection was reduced to 0.6% following QPCR optimization (FIG. 17). Thus, the methods described herein for primer design and QPCR optimization allow for assay specificity even when there is a single nucleotide mismatch that is more than 3 bases from the 3' end of the miRNA-specific QPCR primer.

If the miRNA nucleotide sequence has one or more naturally-occurring G at the 5' end of the miRNA, addition of one or more G to the miRNA-specific QPCR primer may decrease primer solubility or introduce secondary structure. Such limitations can be identified using the Examples described herein.

miRNA are grouped into families based upon high sequence homology at nucleotide positions 2 through 7 from the 5' end. However, it is homology at the 3' end of the miRNA-specific QPCR primer that will result in a lack of specificity. While the examples given herein are based on sequence homology between miRNA family members, it should be recognized that significant homology also exists between various miRNA at the 3' end and that it is more critical to design miRNA-specific QPCR primers based on the homology at the 3' end rather than the 5' end of miRNA.

Example 33

QPCR Conditions Resulting in High Assay Sensitivity and Specificity

It should be noted that in all of the experiments described herein, there was little or no background signal in the absence of a miRNA template. Thus, this method does not have significant background signal from primer:primer dimers as described with other methods. The lack of background results in a wider dynamic range in these assays.

While these experiments yield guidelines on the amount of Perfect Match to use with the Brilliant® SYBR® Green QPCR Core Kit (Stratagene), one of skill in the art would realize that other QPCR or PCR reagents, while yielding adequate results, might still yield different results. Thus, experiments such as those detailed herein can be performed with those reagents to optimize them for use in accordance with the present invention. Such experiments to optimize other commercially available systems is well within the level of skill of those of skill in the art, and do not require undue experimentation.

It will be apparent to those skilled in the art that various modifications and variations can be made in the practice of the present invention without departing from the scope or spirit of the invention. Other embodiments of the invention will be apparent to those skilled in the art from consideration of the specification and practice of the invention. It is intended that the specification and examples be considered as exemplary only, with a true scope and spirit of the invention being indicated by the following claims.

The invention claimed is:

1. A method of designing and making a nucleotide primer for an miRNA, said method comprising:
   comparing two or more nucleotide sequences of miRNA having a region of identity or homology;
   identifying one or more nucleotide positions with heterogeneity among the sequences compared;
   selecting a nucleotide at or within two nucleotides of the identified heterogeneous positions as the 3' end of the primer, wherein the selected nucleotide is, part of the natural sequence of an miRNA of interest among the sequences compared but is not the natural 3' terminal nucleotide of the miRNA;
   selecting some or all of the nucleotides of the remaining region of identity or homology as additional nucleotides of the primer;
   adding zero to ten nucleotides to the 5' end of the primer; and
   synthesizing the primer.

2. The method of claim 1, wherein zero to three guanine nucleotides are added to the 5' end of the primer.

3. The method of claim 1, wherein the Tm of the designed primer is from about 45 degrees to about 70 degrees Celsius.

4. The method of claim 1, wherein the nucleotide sequences are selected from noncoding RNA sequences.

5. The method of claim 1, wherein the nucleotide sequences are selected from miRNA sequences.

6. The method of claim 1, wherein the 3' end of the primer is selected to be at a heterogeneous nucleotide position.

7. A composition comprising the primer of claim 1.

8. The composition of claim 7, comprising at least one reverse transcriptase, at least one adapter primer, at least one reverse amplification primer, at least one polymerase, or a combination of two or more of these.

9. The composition of claim 7, comprising a sample containing or suspected of containing a miRNA of interest.

10. The composition of claim 7, comprising some or all of the components necessary to perform QPCR.

11. A kit comprising, in packaged combination, at least one miRNA-specific primer comprising a nucleotide at the 3' end that is heterogeneous among at least three miRNA species, and comprising at least one guanine nucleotide on the 5' end that is not found naturally in the target miRNA, wherein the nucleotide at the 3' end of the primer is part of the natural sequence of the target miRNA but is not the natural 3' terminal nucleotide of the miRNA.

12. The kit of claim 11, comprising at least one reverse transcriptase, at least one adapter primer, at least one reverse amplification primer, at least one polymerase, or a combination of two or more of these.

13. The kit of claim 11, comprising a sample containing or suspected of containing a miRNA of interest.

* * * * *

UNITED STATES PATENT AND TRADEMARK OFFICE
CERTIFICATE OF CORRECTION

| | | |
|---|---|---|
| PATENT NO. | : 8,314,220 B2 | Page 1 of 1 |
| APPLICATION NO. | : 11/627926 | |
| DATED | : November 20, 2012 | |
| INVENTOR(S) | : Rebecca L. Mullinax et al. | |

It is certified that error appears in the above-identified patent and that said Letters Patent is hereby corrected as shown below:

On the face page, in field (54), in column 1, line 1, and in column 1, line 1, "Title", delete "METHODS" and insert -- METHODS, --, therefor.

On the face page, in field (56), under "Other Publications", in column 1, line 14, delete "monphosphorylation" and insert -- monophosphorylation --, therefor.

In column 127, line 44, in Claim 1, delete "is," and insert -- is --, therefor.

Signed and Sealed this
Twenty-second Day of January, 2013

David J. Kappos
*Director of the United States Patent and Trademark Office*